(12) United States Patent
Greenhalgh et al.

(10) Patent No.: US 12,207,854 B2
(45) Date of Patent: Jan. 28, 2025

(54) EXPANDABLE ATTACHMENT DEVICE AND METHOD

(71) Applicant: Stout Medical Group, L.P., Warrington, PA (US)

(72) Inventors: E. Skott Greenhalgh, Gladwyne, PA (US); John-Paul Romano, Chalfont, PA (US); Michael P. Igoe, Windham, NH (US); Robert A. Kiefer, Quakertown, PA (US); Wade K. Trexler, Coopersburg, PA (US)

(73) Assignee: Stout Medical Group, L.P., Warrington, PA (US)

( * ) Notice: Subject to any disclaimer, the term of this patent is extended or adjusted under 35 U.S.C. 154(b) by 433 days.

(21) Appl. No.: 16/560,064

(22) Filed: Sep. 4, 2019

(65) Prior Publication Data
US 2020/0015873 A1 Jan. 16, 2020

Related U.S. Application Data

(63) Continuation of application No. 12/556,820, filed on Sep. 10, 2009, now abandoned, which is a
(Continued)

(51) Int. Cl.
*A61B 17/86* (2006.01)
*A61B 17/72* (2006.01)
(Continued)

(52) U.S. Cl.
CPC ........ *A61B 17/863* (2013.01); *A61B 17/7258* (2013.01); *A61B 17/744* (2013.01);
(Continued)

(58) Field of Classification Search
CPC .............. A61B 17/844; A61B 17/8685; A61B 17/8625; A61B 17/863; A61B 17/8858; A61B 17/7275; A61B 2017/8655
See application file for complete search history.

(56) References Cited

U.S. PATENT DOCUMENTS 1,394,925 A 10/1921 Marshall
1,438,648 A 12/1922 Jacobs
(Continued)

FOREIGN PATENT DOCUMENTS

EP 0129442 12/1984
EP 0574707 12/1993
(Continued)

OTHER PUBLICATIONS

U.S. Appl. No. 12/556,820, filed Sep. 10, 2009.
(Continued)

*Primary Examiner* — Amy R Sipp
(74) *Attorney, Agent, or Firm* — Levine Bagade Han LLP

(57) ABSTRACT

An attachment device with a radially expandable section is disclosed. The attachment device can have helical threads, for example, to facilitate screwing the attachment device into a bone. Methods of using the same are also disclosed. The attachment device can be positioned to radially expand the expandable section in cancellous bone substantially surrounded by cortical bone.

20 Claims, 73 Drawing Sheets

Related U.S. Application Data continuation of application No. PCT/US2008/003421, filed on Mar. 12, 2008.

(60) Provisional application No. 60/906,791, filed on Mar. 12, 2007.

(51) Int. Cl.
  *A61B 17/74* (2006.01)
  *A61B 17/88* (2006.01)
  *A61C 8/00* (2006.01)
  *A61B 17/00* (2006.01)
  *A61B 17/70* (2006.01)

(52) U.S. Cl.
  CPC ...... *A61B 17/8685* (2013.01); *A61B 17/8858* (2013.01); *A61B 17/8875* (2013.01); *A61C 8/0033* (2013.01); A61B 2017/00004 (2013.01); A61B 17/7098 (2013.01); A61B 17/7291 (2013.01); A61B 17/861 (2013.01); A61B 17/866 (2013.01); A61B 17/8872 (2013.01)

(56) References Cited

U.S. PATENT DOCUMENTS

| | | |
|---|---|---|
| 2,121,193 A | 6/1938 | Hanicke |
| 4,269,106 A | 5/1981 | Leibhard et al. |
| 4,456,005 A | 6/1984 | Lichty |
| 4,738,255 A | 4/1988 | Goble et al. |
| 5,037,422 A | 8/1991 | Hayhurst et al. |
| 5,046,513 A | 9/1991 | Gatturna et al. |
| 5,059,193 A | 10/1991 | Kuslich |
| 5,065,490 A | 11/1991 | Wivagg et al. |
| 5,207,679 A | 5/1993 | Li |
| 5,209,753 A * | 5/1993 | Biedermann ...... A61B 17/8685 606/314 |
| 5,221,261 A | 6/1993 | Termin et al. |
| 5,236,445 A | 8/1993 | Hayhurst et al. |
| 5,261,909 A | 11/1993 | Sutterlin et al. |
| 5,360,431 A | 11/1994 | Puno et al. |
| 5,390,683 A | 2/1995 | Pisharodi |
| 5,411,522 A | 5/1995 | Trott |
| 5,472,452 A | 12/1995 | Trott |
| 5,474,555 A | 12/1995 | Puno et al. |
| 5,480,403 A | 1/1996 | Lee et al. |
| 5,489,210 A | 2/1996 | Hanosh |
| 5,498,265 A | 3/1996 | Asnis et al. |
| 5,501,695 A | 3/1996 | Anspach et al. |
| 5,522,844 A | 6/1996 | Johnson |
| 5,643,321 A | 7/1997 | Mcdevitt |
| 5,649,950 A | 7/1997 | Bourne et al. |
| 5,662,654 A | 9/1997 | Thompson |
| 5,709,708 A | 1/1998 | Thal |
| 5,713,904 A * | 2/1998 | Errico ...... A61B 17/8685 606/327 |
| 5,749,883 A | 5/1998 | Halpern |
| 5,749,899 A | 5/1998 | Bardin |
| 5,782,866 A | 7/1998 | Wenstrom |
| 5,797,963 A | 8/1998 | Mcdevitt |
| 5,824,011 A | 10/1998 | Stone et al. |
| 5,849,004 A | 12/1998 | Bramlet |
| 5,868,708 A | 2/1999 | Hart et al. |
| 5,882,350 A | 3/1999 | Ralph et al. |
| 5,935,129 A | 8/1999 | Mcdevitt et al. |
| 6,048,343 A | 4/2000 | Mathis et al. |
| 6,146,406 A | 11/2000 | Shluzas et al. |
| 6,168,597 B1 | 1/2001 | Biedermann et al. |
| 6,200,330 B1 | 3/2001 | Benderev et al. |
| 6,210,376 B1 | 4/2001 | Grayson |
| 6,214,012 B1 | 4/2001 | Karpman et al. |
| 6,224,600 B1 | 5/2001 | Protogirou |
| 6,224,625 B1 | 5/2001 | Jayaraman |
| 6,319,255 B1 | 11/2001 | Grundei et al. |
| 6,436,142 B1 * | 8/2002 | Paes ...... A61F 2/442 623/908 |
| 6,458,100 B2 | 10/2002 | Roue et al. |
| 6,506,051 B2 | 1/2003 | Levisman |
| 6,582,453 B1 * | 6/2003 | Tran ...... A61B 17/0401 606/68 |
| 6,585,770 B1 | 7/2003 | White et al. |
| 6,602,034 B2 | 8/2003 | Wakai et al. |
| 6,626,861 B1 | 9/2003 | Hart et al. |
| 6,648,893 B2 | 11/2003 | Dudasik |
| 6,652,561 B1 | 11/2003 | Tran |
| 6,668,688 B2 | 12/2003 | Zhao et al. |
| 6,676,665 B2 | 1/2004 | Foley et al. |
| 6,719,509 B1 | 4/2004 | Huang et al. |
| 7,097,648 B1 | 8/2006 | Globerman et al. |
| 7,250,055 B1 | 7/2007 | Vanderwalle |
| 7,608,062 B2 | 10/2009 | Sweeney |
| 7,608,097 B2 | 10/2009 | Kyle |
| 8,092,504 B2 | 1/2012 | Warnick |
| 8,231,632 B1 | 7/2012 | Jordan et al. |
| 8,460,305 B2 | 6/2013 | Jordan et al. |
| 8,574,273 B2 | 11/2013 | Russell et al. |
| 8,608,802 B2 | 12/2013 | Bagga et al. |
| 8,636,784 B2 | 1/2014 | Greenhalgh et al. |
| 8,795,362 B2 | 8/2014 | Anderson et al. |
| 8,906,022 B2 | 12/2014 | Krinke et al. |
| 9,095,390 B2 | 8/2015 | Wallenstein et al. |
| 9,681,905 B2 | 6/2017 | Reimels |
| 10,888,363 B2 | 1/2021 | Greenhalgh et al. |
| 2001/0021852 A1 | 9/2001 | Chappius |
| 2002/0049447 A1 | 4/2002 | Li |
| 2002/0058947 A1 | 5/2002 | Hochschuler et al. |
| 2002/0077520 A1 | 6/2002 | Segal et al. |
| 2002/0147454 A1 * | 10/2002 | Neto ...... A61B 17/8685 606/313 |
| 2002/0165544 A1 | 11/2002 | Perren et al. |
| 2002/0198527 A1 | 12/2002 | Muckter |
| 2004/0015172 A1 | 1/2004 | Biedermann et al. |
| 2004/0116992 A1 | 6/2004 | Wardle et al. |
| 2004/0133204 A1 | 7/2004 | Davies |
| 2004/0138707 A1 | 7/2004 | Greenhalgh |
| 2004/0167625 A1 | 8/2004 | Beyar et al. |
| 2004/0181234 A1 | 9/2004 | McDevitt et al. |
| 2004/0267254 A1 | 12/2004 | Manzo et al. |
| 2004/0267265 A1 | 12/2004 | Kyle |
| 2005/0065526 A1 | 3/2005 | Drew et al. |
| 2005/0113919 A1 | 5/2005 | Cragg et al. |
| 2005/0143827 A1 | 6/2005 | Globerman et al. |
| 2005/0187555 A1 | 8/2005 | Biedermann et al. |
| 2005/0228391 A1 | 10/2005 | Levy et al. |
| 2005/0261781 A1 | 11/2005 | Sennett et al. |
| 2005/0277966 A1 | 12/2005 | Ewers et al. |
| 2006/0015104 A1 | 1/2006 | Dalton |
| 2006/0052788 A1 | 3/2006 | Thelen et al. |
| 2006/0072979 A1 * | 4/2006 | McDuff ...... F16B 13/061 411/30 |
| 2006/0084987 A1 | 4/2006 | Kim |
| 2006/0190090 A1 | 8/2006 | Plaskon |
| 2006/0206208 A1 | 9/2006 | Michelson |
| 2006/0224241 A1 | 10/2006 | Butler et al. |
| 2006/0235391 A1 | 10/2006 | Sutterlin |
| 2006/0264950 A1 | 11/2006 | Nelson et al. |
| 2006/0271061 A1 | 11/2006 | Beyar et al. |
| 2007/0032791 A1 | 2/2007 | Greenhalgh |
| 2007/0093899 A1 | 4/2007 | Dutoit et al. |
| 2007/0106383 A1 | 5/2007 | Abdou |
| 2007/0161985 A1 | 7/2007 | Demakas et al. |
| 2007/0173939 A1 | 7/2007 | Kim et al. |
| 2007/0198018 A1 | 8/2007 | Biedermann et al. |
| 2007/0213732 A1 | 9/2007 | Khanna et al. |
| 2007/0270627 A1 | 11/2007 | Cutrer et al. |
| 2007/0282443 A1 | 12/2007 | Globerman et al. |
| 2008/0269749 A1 | 10/2008 | Shalaby et al. |
| 2008/0288003 A1 | 11/2008 | Mckinley |
| 2009/0062868 A1 * | 3/2009 | Casutt ...... A61B 17/7001 606/301 |
| 2009/0125028 A1 | 5/2009 | Teisen et al. |
| 2009/0131992 A1 | 5/2009 | Greenhalgh et al. |
| 2009/0204158 A1 | 8/2009 | Sweeney |

(56) References Cited

U.S. PATENT DOCUMENTS

| | | |
|---|---|---|
| 2010/0016905 A1 | 1/2010 | Greenhalgh et al. |
| 2010/0030135 A1 | 2/2010 | Mitchell |
| 2010/0042215 A1 | 2/2010 | Stalcup et al. |
| 2010/0100135 A1 | 4/2010 | Phan |
| 2010/0106199 A1 | 4/2010 | Sawa et al. |
| 2011/0015641 A1 | 1/2011 | Matsumoto |
| 2011/0060373 A1 | 3/2011 | Russell et al. |
| 2012/0029578 A1 | 2/2012 | Suh |
| 2014/0046379 A1 | 2/2014 | Sweeney |
| 2014/0046381 A1 | 2/2014 | Asfora |
| 2014/0288651 A1 | 9/2014 | Biedermann et al. |
| 2015/0012051 A1 | 1/2015 | Warren et al. |
| 2015/0250513 A1 | 9/2015 | De Lavigne Sainte Suzanne |
| 2016/0213413 A1 | 7/2016 | Hientzsch et al. |
| 2018/0071000 A1 | 3/2018 | Pham et al. |
| 2018/0368986 A1 | 12/2018 | Greenhalgh et al. |
| 2019/0167326 A1 | 6/2019 | Greenhalgh et al. |
| 2019/0374269 A1 | 12/2019 | Kiefer et al. |
| 2020/0330142 A1 | 10/2020 | Greenhalgh et al. |

FOREIGN PATENT DOCUMENTS

| | | |
|---|---|---|
| JP | 4-502567 | 5/1992 |
| JP | 11-504550 | 4/1999 |
| JP | 2003-513698 | 5/2001 |
| JP | 2002-514935 | 5/2002 |
| WO | WO 1995/025469 | 9/1995 |
| WO | WO 2000/044319 | 8/2000 |
| WO | WO 2000/044321 | 8/2000 |
| WO | WO 2000/044946 | 8/2000 |
| WO | WO 2001/034045 | 5/2001 |
| WO | WO 2001/054598 | 8/2001 |
| WO | WO 2003/003951 | 1/2003 |
| WO | WO 2003/047440 | 6/2003 |
| WO | WO 2004/004596 | 1/2004 |
| WO | WO 2005/034764 | 4/2005 |
| WO | WO 2005/096975 | 10/2005 |
| WO | WO 2006/034396 | 3/2006 |
| WO | WO 2006/034436 | 3/2006 |
| WO | WO 2006/037013 | 4/2006 |
| WO | WO 2006/068682 | 6/2006 |
| WO | WO 2006/116760 | 11/2006 |
| WO | WO 2006/116761 | 11/2006 |
| WO | WO 2006/126979 | 11/2006 |
| WO | WO 2007/041665 | 4/2007 |
| WO | WO 2007/065137 | 6/2007 |
| WO | WO 2007/073488 | 6/2007 |
| WO | WO 2007/076374 | 7/2007 |
| WO | WO 2007/076377 | 7/2007 |
| WO | WO 2007/131002 | 11/2007 |
| WO | WO 2008/112308 | 9/2008 |
| WO | WO 2009/059227 | 5/2009 |
| WO | WO 2017/147537 | 8/2017 |
| WO | WO 2019/113095 | 6/2019 |
| WO | WO 2021/011313 | 1/2021 |

OTHER PUBLICATIONS

U.S. Appl. No. 10/342,008, filed Jan. 14, 2003.
U.S. Appl. No. 12/264,181, filed Nov. 3, 2008.
Franklin, I.J. et al., "Uptake of Tetracycline by Aortic Aneurysm Wall and Its Effect on Inflammation and Proteolysis," *Brit. J. Surger*, 86(6):771-775, Jun. 1999.
Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, Jun. 2000.
Tambiah, J. et al., "Provocation of Experimental Aortic Inflammation Mediators and Chlamydia Pneumoniae," *Brit., J. Surgery*, 88(7):935-940, Feb. 2001.
Walton, L.J. et al., "Inhibition of Prostoglandin E2 Synthesis in Abdominal Aortic Aneurysms," *Circulation*, 48-54, Jul. 6, 1999.
Xu, Q. et al., "Sp1 Increases Expression of Cyclooxygenase-2 in Hypoxic Vascular Endothelium," *J. Biological Chemistry*, 275(32):24583-24589, Aug. 2000.

\* cited by examiner

NOT INVENTION

NOT INVENTION

NOT INVENTION

NOT INVENTION

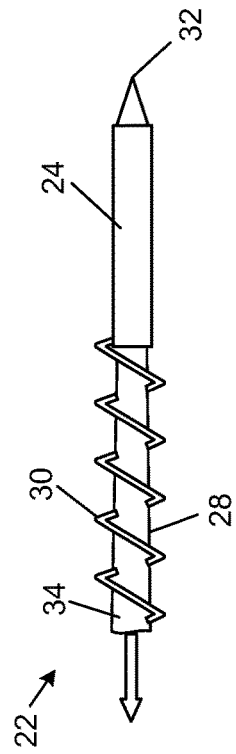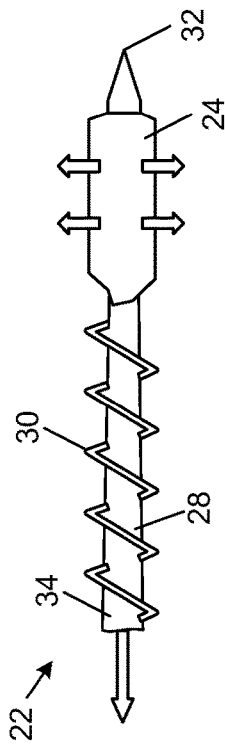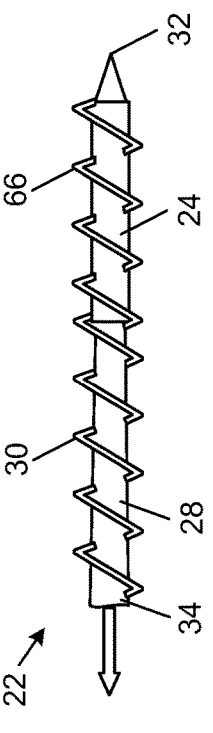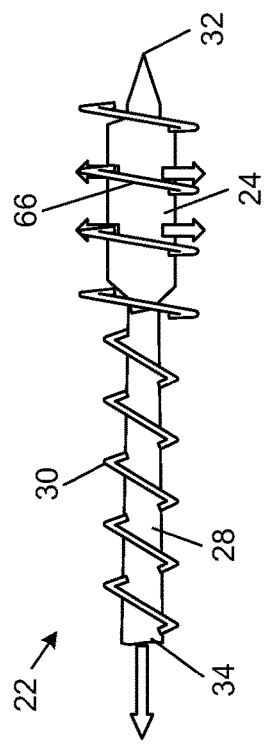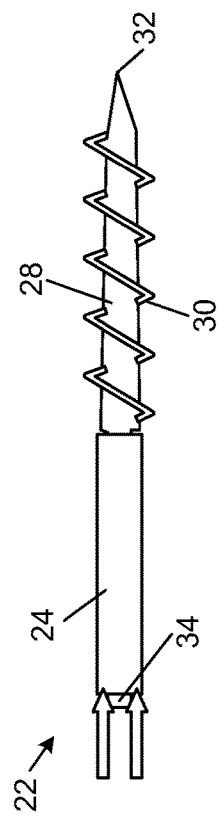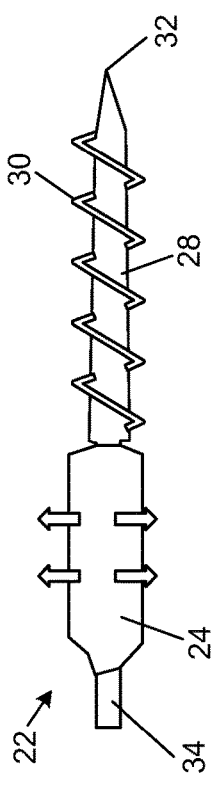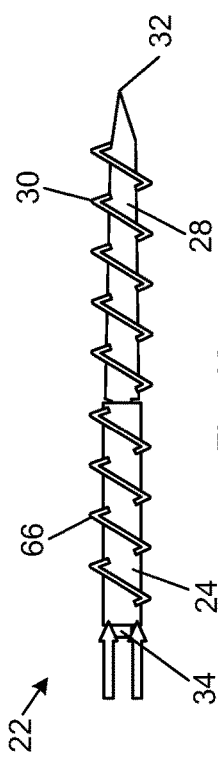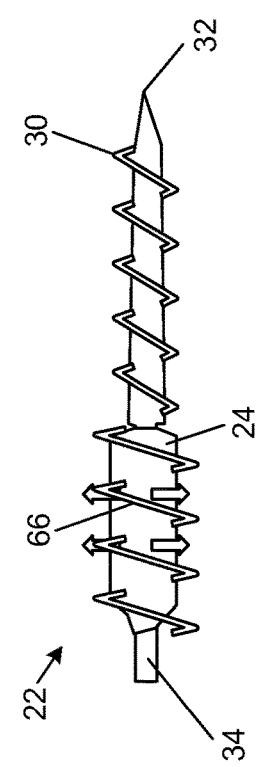

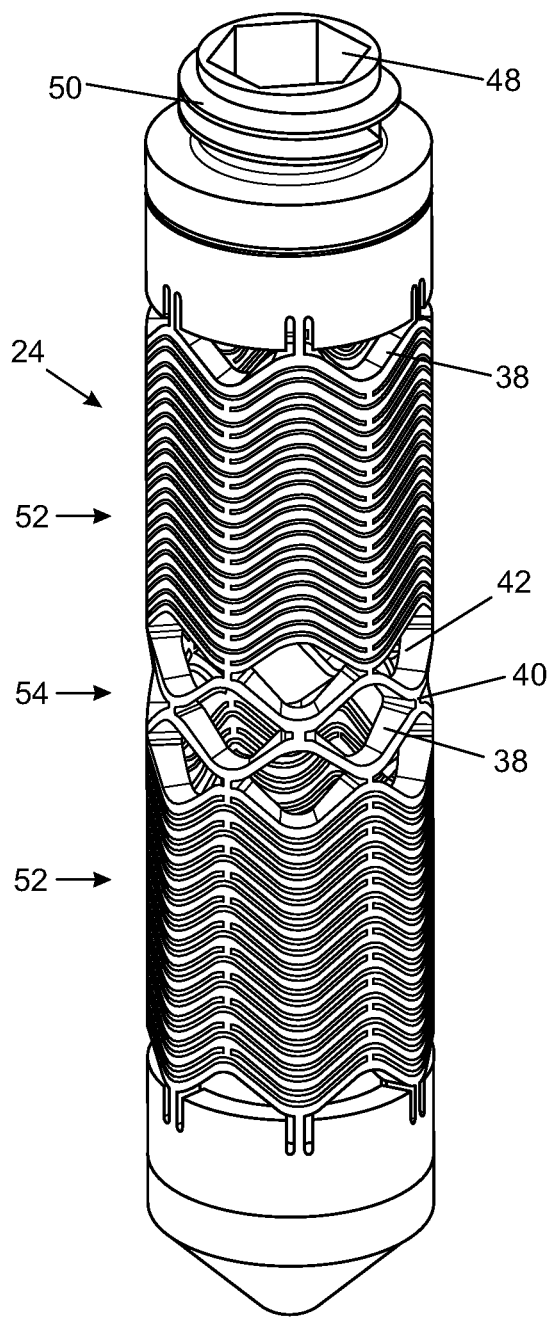
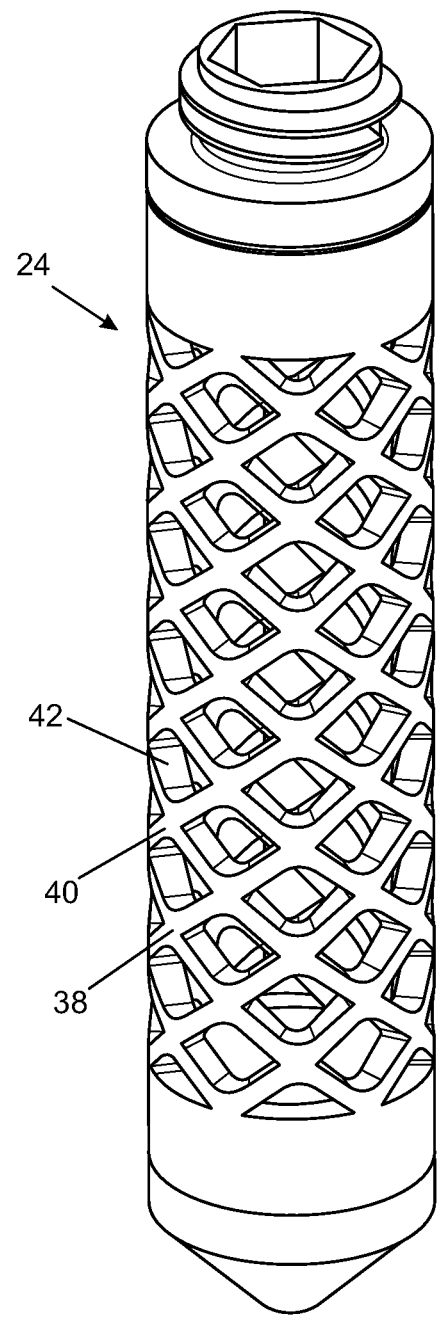
Fig. 25a
Fig. 25b

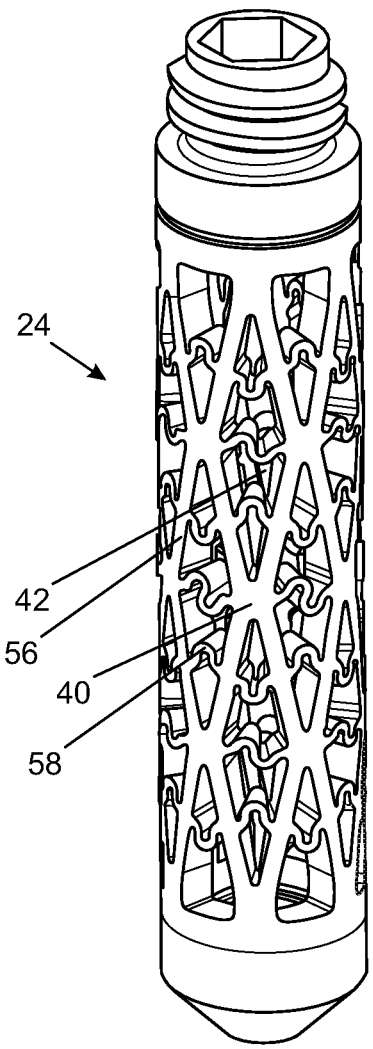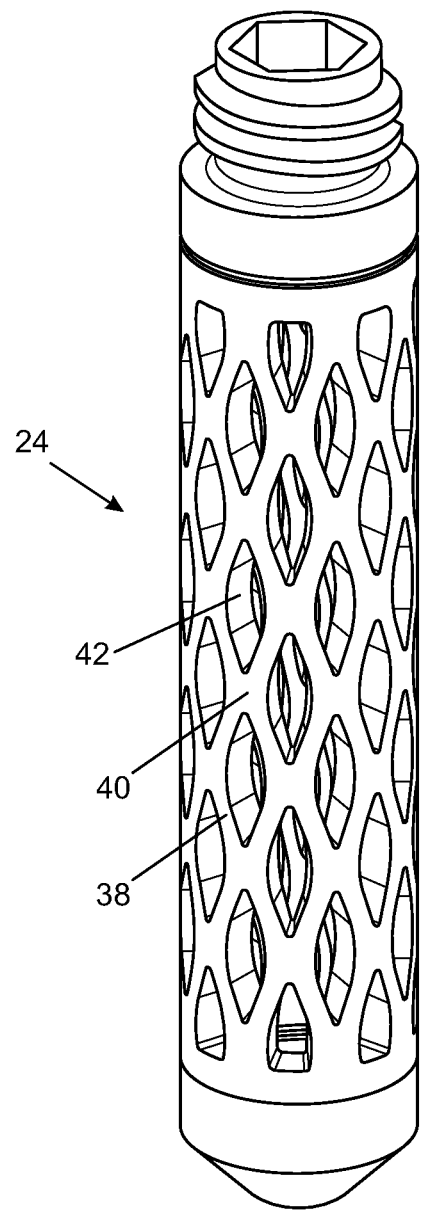
Fig. 25c
Fig. 25d

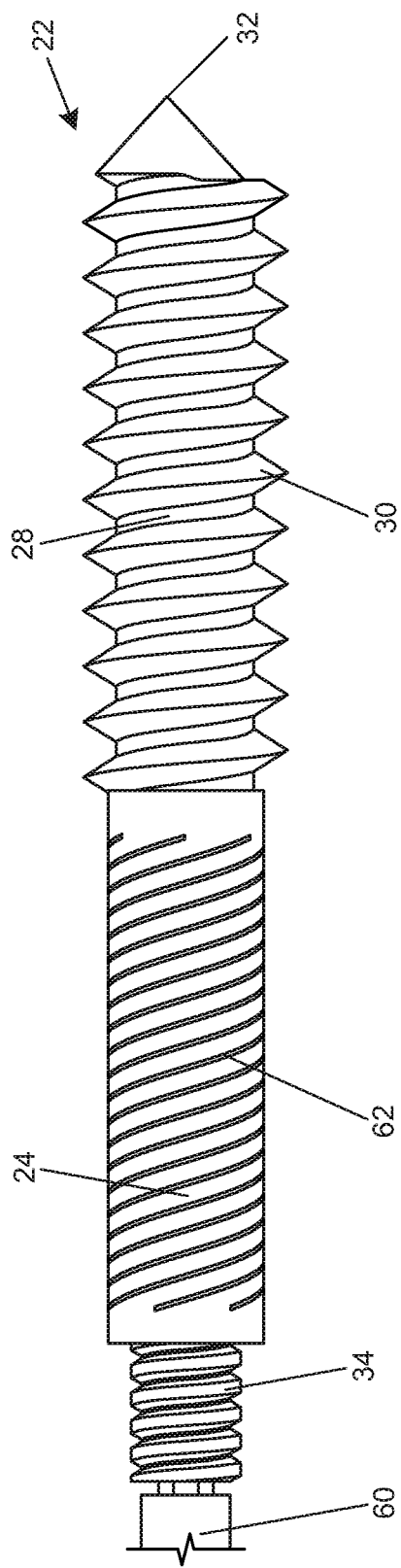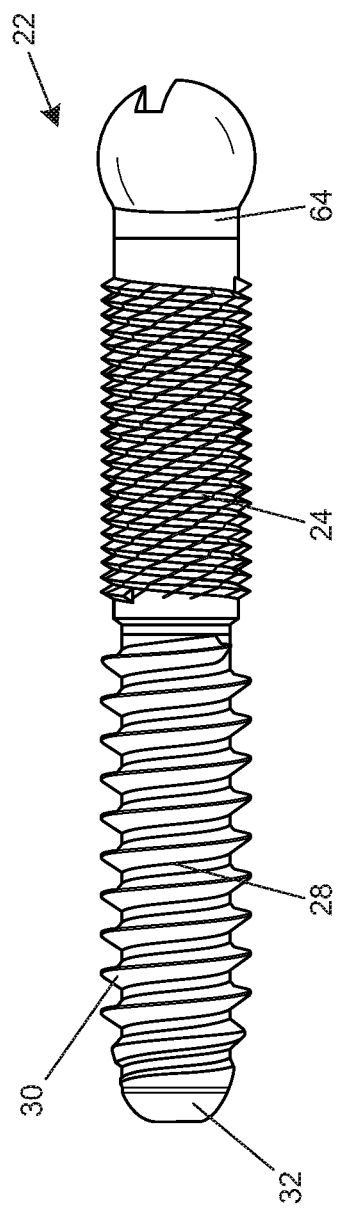
Fig. 30
Fig. 31

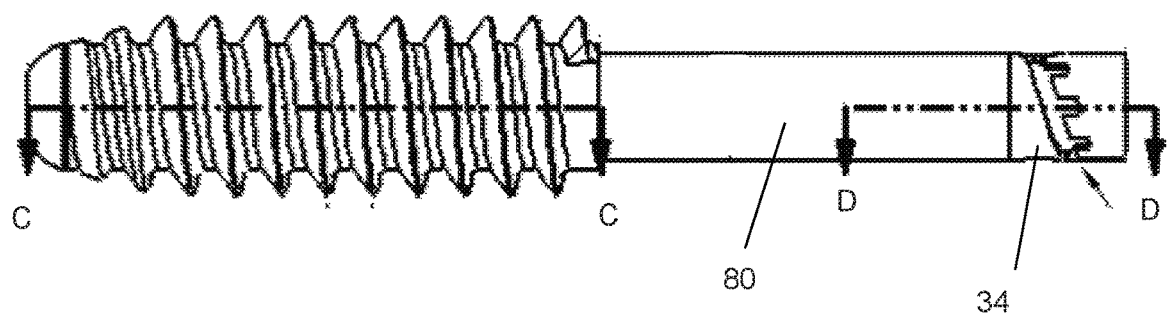
Fig. 41
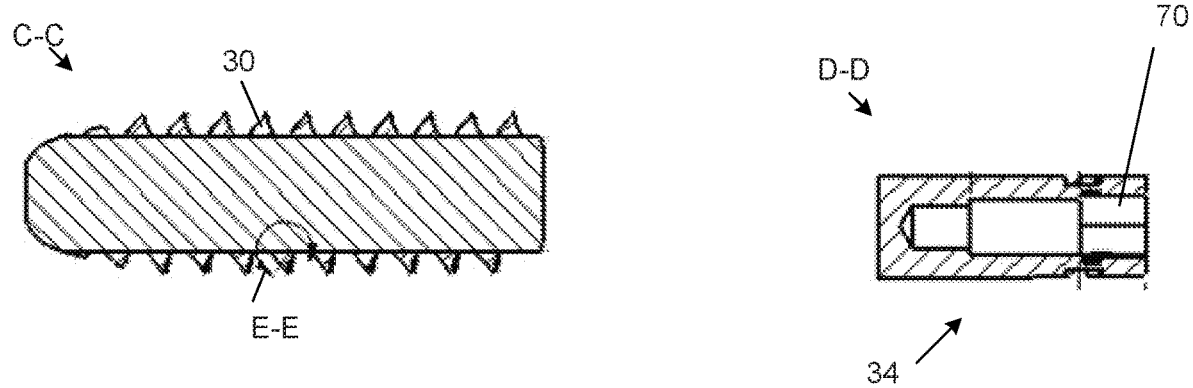
Fig. 42
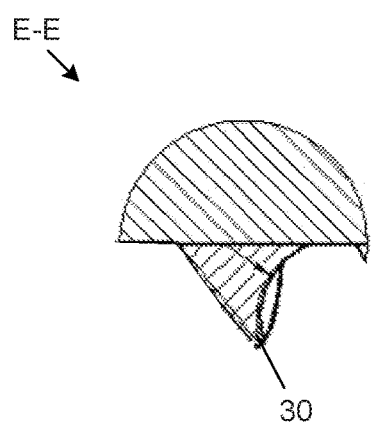
Fig. 44
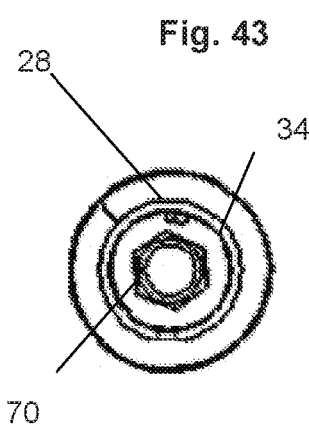
Fig. 43
Fig. 45

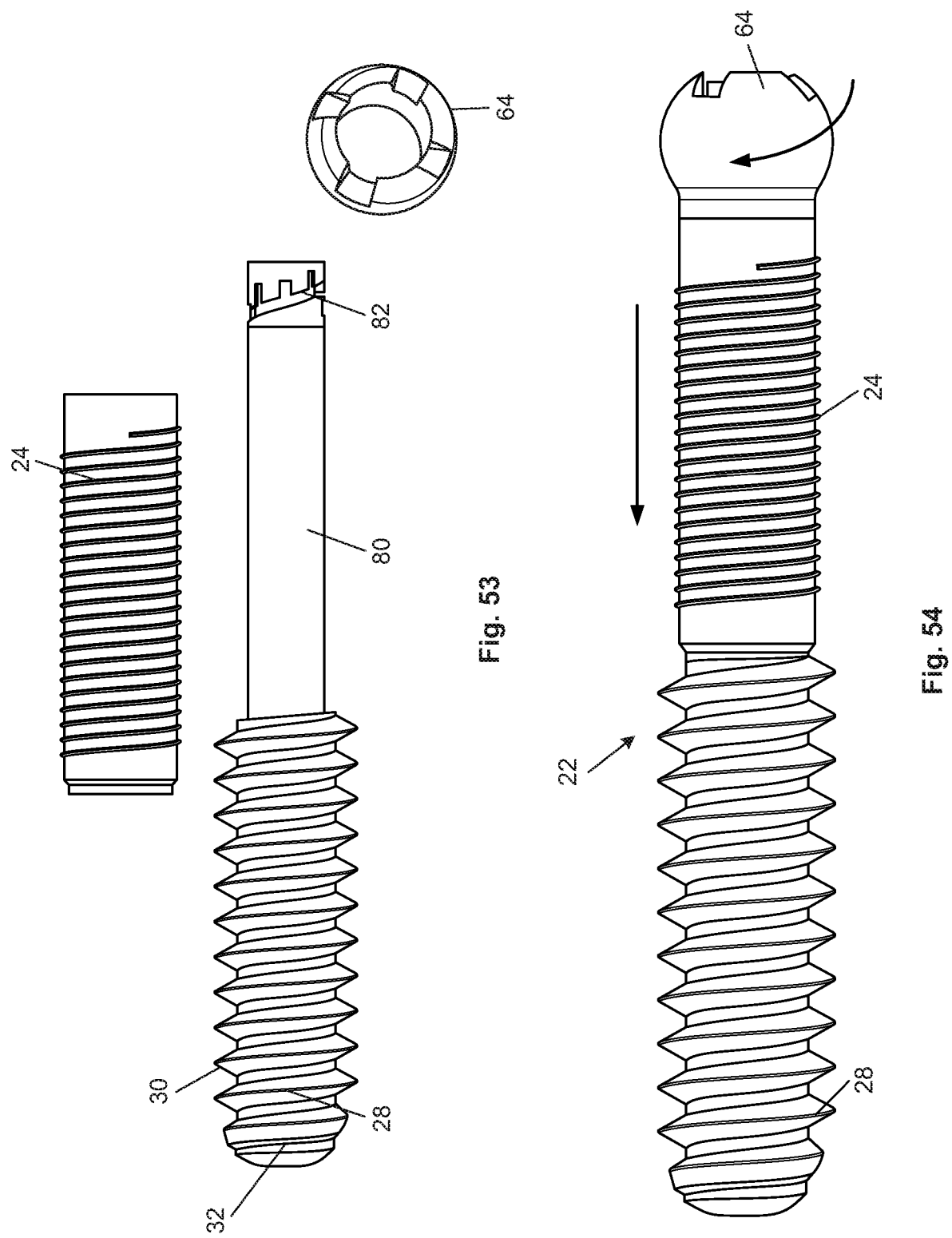

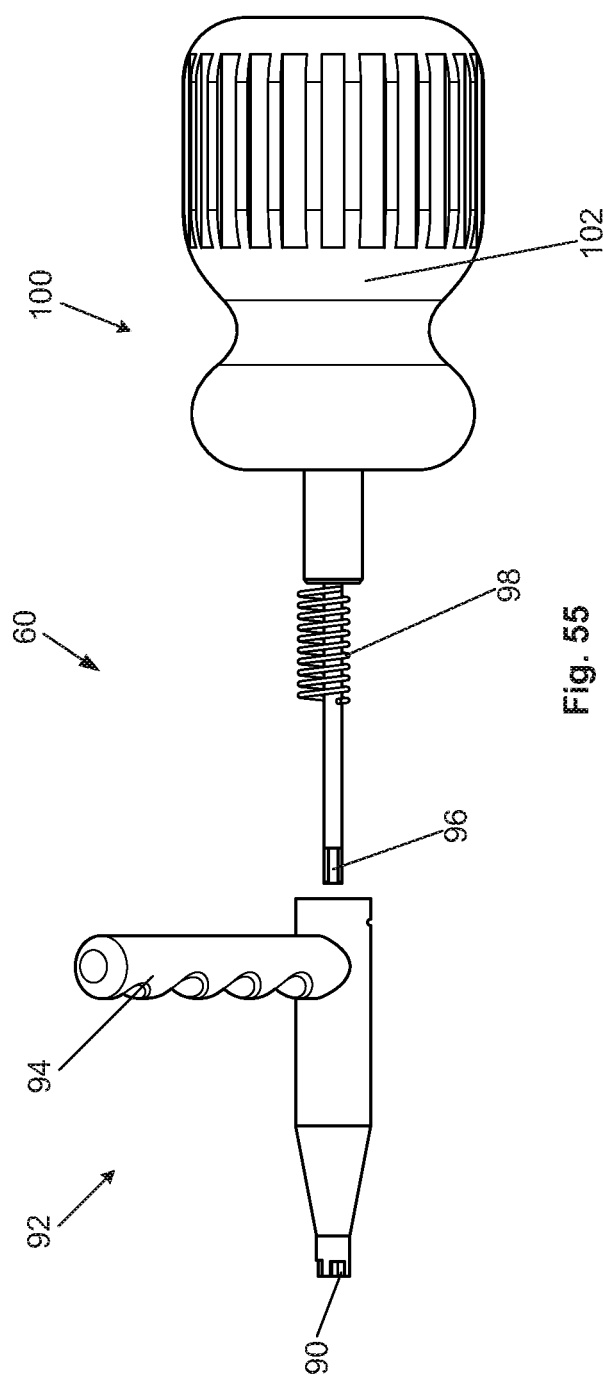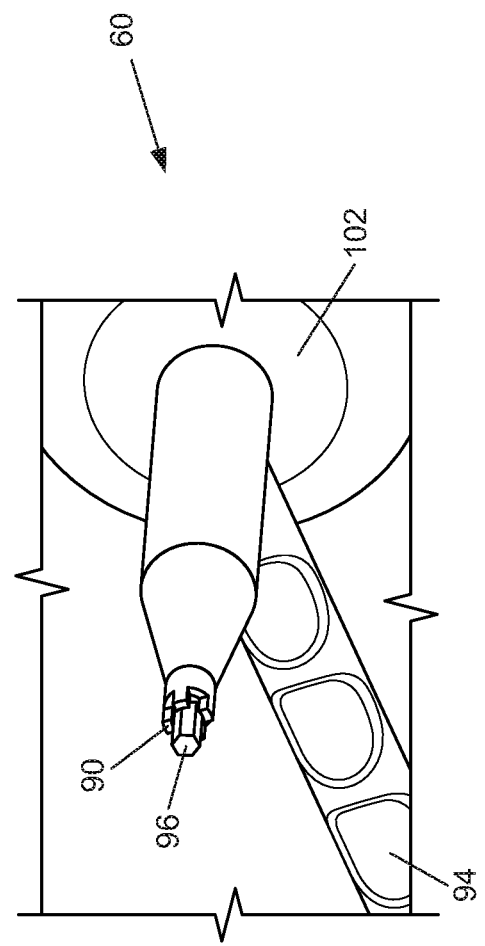
Fig. 55
Fig. 56

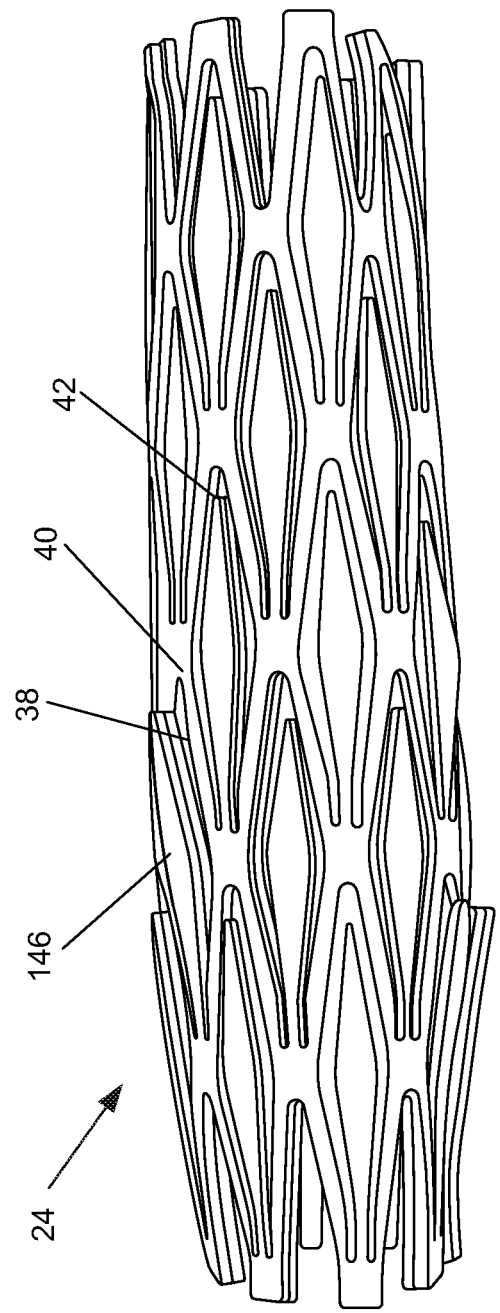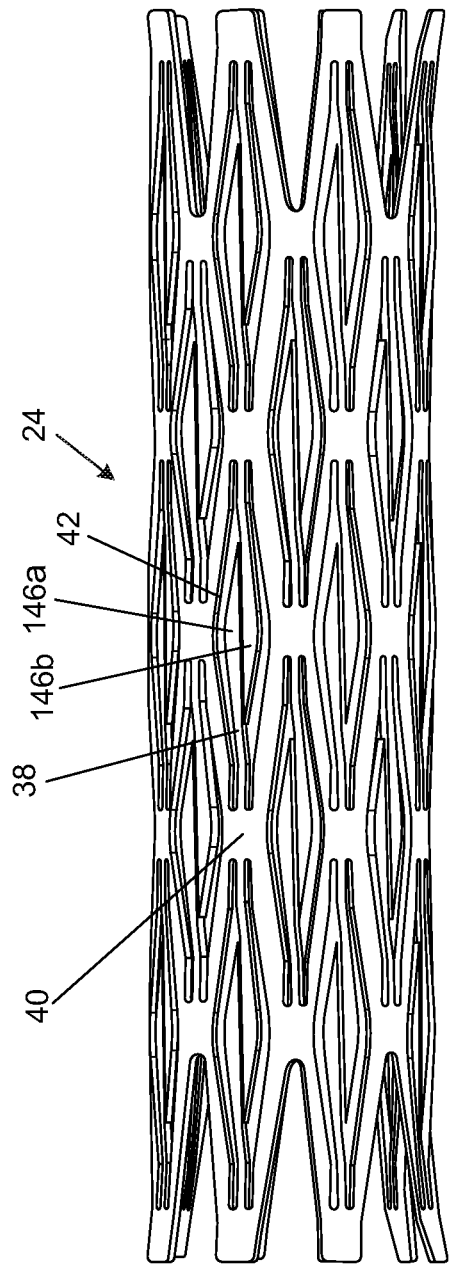
Fig. 83
Fig. 84

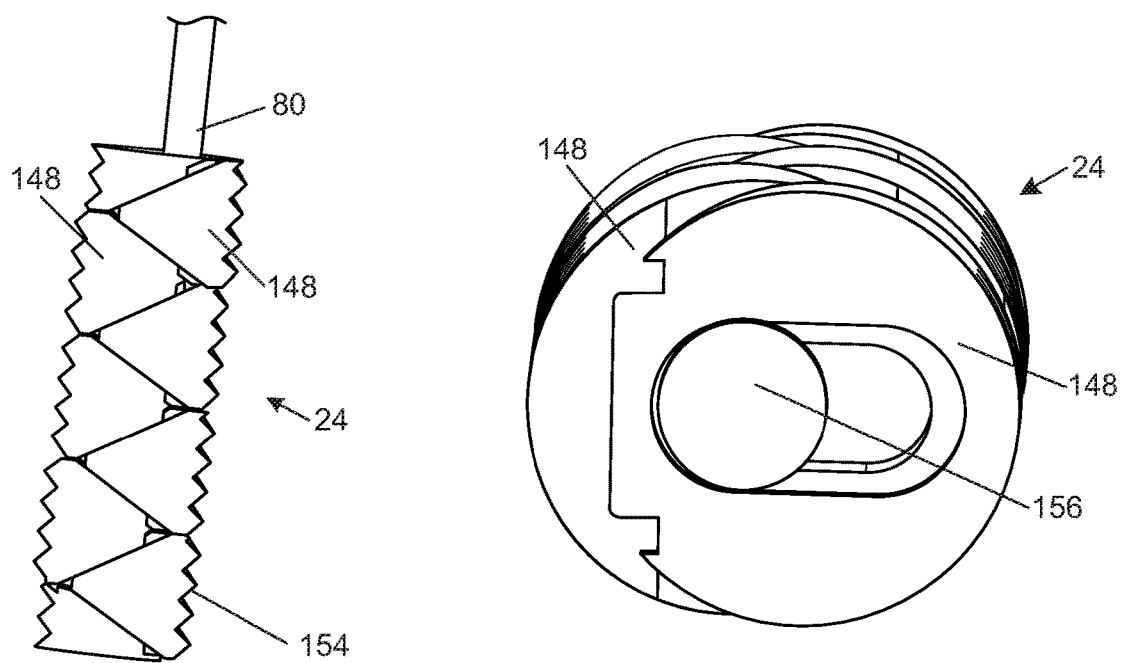
Fig. 99
Fig. 100
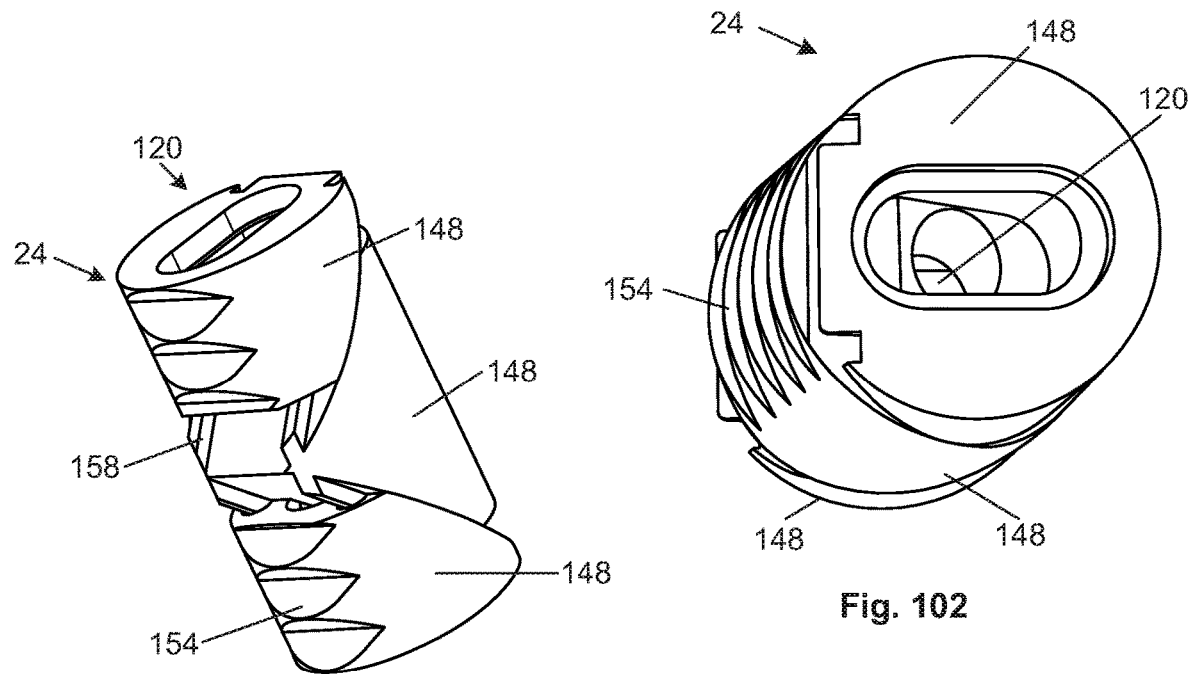
Fig. 101
Fig. 102

EXPANDABLE ATTACHMENT DEVICE AND METHOD

CROSS-REFERENCE TO RELATED APPLICATIONS

This application is a continuation of U.S. patent application Ser. No. 12/556,820, filed Sep. 10, 2009, which is a continuation of PCT Application No. PCT/US2008/003421, filed Mar. 12, 2008, which claims priority to U.S. Provisional Application No. 60/906,791, filed Mar. 12, 2007, each of which is incorporated by reference herein in their entireties.

BACKGROUND OF THE INVENTION

1. Field of the Invention

The present invention relates generally to a device and method for attaching to bones.

2. Description of Related Art

Broken bones, such as compression fractures of one or more vertebrae in the spine, may be treated with internal fixation. Any indication needed spinal stability can also be treated by internal fixation. Examples include scoliosis, kyphosis, spondylothisthesis and rotation, segmental instability, such as disc degeneration and fracture caused by disease and trauma and congenital defects, and degeneration caused by tumors.

As shown by FIG. 1, internal fixation in the spine is often accomplished by first screwing fixation screws into the pedicles and vertebral bodies of the vertebrae 10. FIG. 2 shows that the fixation screws are then typically attached to a rigid fixation rod or plate that provide support between one or more weakened vertebra 10. This support often immobilizes the vertebra 10 to which the fixation screws have been inserted.

FIG. 3 illustrates that existing fixation systems often have the fixation rod 14 or plate 220, through which a number of fixation screws 12 are deployed. The screw head 18 prevents the fixation rod 14 from separating from the fixation screw 12. The fixation screw 12 also has a screw body 16 which has a screw longitudinal axis 20 often static relative to the fixation rod 14.

FIG. 4 illustrates that in some existing fixation systems, the fixation screws 12 can be polyaxial screws: attached to the fixation rod 14 or plate 220 in a manner so that the screw longitudinal axis 20 can rotate, as shown by arrows, with respect to the fixation rod 14.

Backing out or loosening of the fixation screws 12 can cause a reduction of the fixation, up to complete failure or even resulting in additional complications.

Furthermore, the bones are often weak and under heavy loads, the bones can fail and the fixation screws 12 can be ripped from the bone resulting in complete failure and additional damage to the bone.

Therefore, a fixation screw that can substantially eliminate the risk of backout, and can provide a higher anchoring force is desired. A fixation screw that can also minimize bone failure is desired.

SUMMARY OF THE INVENTION

An expandable attachment device and methods for using the same are disclosed. The expandable attachment device can have a radially expandable section and a distal end. The distal end can be configured to be attached to a separate device, such as a fixation rod or plate. The device can have an unexpandable section.

Also disclosed is an expandable attachment device that can have a radially expandable section and an unexpandable section. The unexpandable section and/or the radially expandable section can have external threads.

The devices described herein can be used as substitutes for fixation screws in existing fixation systems. The devices can be used to treat broken bones, scoliosis, kyphosis, spondylothisthesis and rotation, segmental instability, such as disc degeneration and fracture caused by disease and trauma and congenital defects, and degeneration caused by tumors.

The devices can be configured to be used in systems with fixed screw longitudinal axis or polyaxial configurations.

BRIEF DESCRIPTION OF THE DRAWINGS

FIGS. 8 and 9 illustrate a variation of the expandable attachment device and a method for radially expanding the device.

FIGS. 10 and 11 illustrate a variation of the expandable attachment device and a method for radially expanding the device.

FIGS. 12 and 13 illustrate a variation of the expandable attachment device and a method for radially expanding the device.

FIGS. 14 and 15 illustrate a variation of the expandable attachment device and a method for radially expanding the device.

FIG. 25a through FIG. 25e illustrate variations of the expandable section.

FIGS. 30 and 31 illustrate variations of the expandable attachment device.

FIG. 41 illustrates a variation of the unexpandable section integral with the central shaft and distal end of the expandable attachment device.

FIG. 42 illustrates a variation of cross-section C-C of FIG. 41.

FIG. 43 illustrates a variation of cross-section D-D of FIG. 41.

FIG. 44 is a variation of a close-up E-E of FIG. 42.

FIG. 45 is a distal end view of a variation of the unexpandable section integral with the central shaft and distal end of the expandable attachment device of FIG. 41.

FIG. 50 illustrates a variation of cross-section Z-Z of FIG. 47a.

FIGS. 53 and 54 illustrate a variation of the expandable attachment device in unassembled and assemble configurations, respectively, and a method for assembling the expandable attachment device.

FIG. 55 illustrates a variation of the deployment tool in an unassembled configuration.

FIG. 56 is a close-up perspective view of the end of the deployment tool in an assembled configuration.

FIGS. 83 and 84 illustrate variations of the expandable section.

FIGS. 99 and 100 are side and proximal end views, respectively, of a variation of the expandable section with the center shaft.

FIGS. 101 and 102 are side and proximal end views, respectively, of a variation of the expandable section.

FIG. 181 illustrates a variation of the expandable attachment device.

FIG. 182 is a close-up view of the expandable attachment device of FIG. 181.

FIG. 183 illustrates cross-section S-S of the expandable attachment device of FIG. 181.

FIG. 184 illustrates a variation of close-up section T-T of the expandable attachment device of FIG. 183

FIG. 185 is a close-up view of a variation of the expandable attachment device.

FIG. 186 is an expanded view of the expandable attachment device of FIG. 185.

FIG. 187 illustrates a variation of cross-section U-U of FIG. 186.

DETAILED DESCRIPTION OF THE INVENTION

Figure 1:
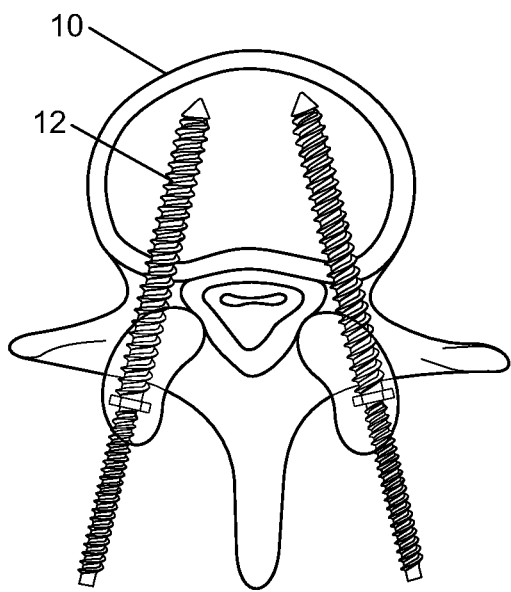
FIG. 1 is a partially see-through top view of a vertebra with fixation screws therethrough.
Figure 2:
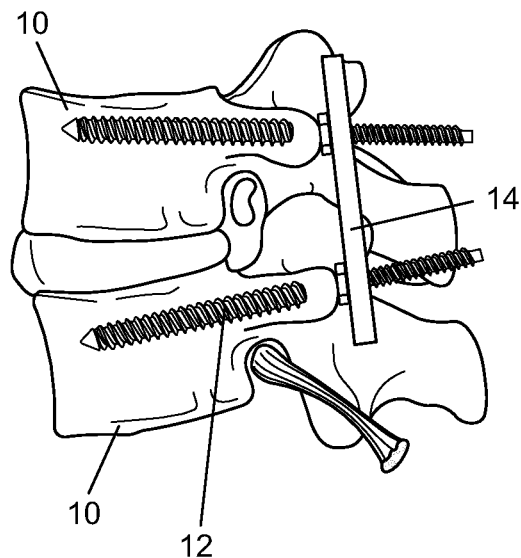
FIG. 2 is a partially see-through lateral view of a section of the spine with fixation screws and a fixation rod.
Figure 3:
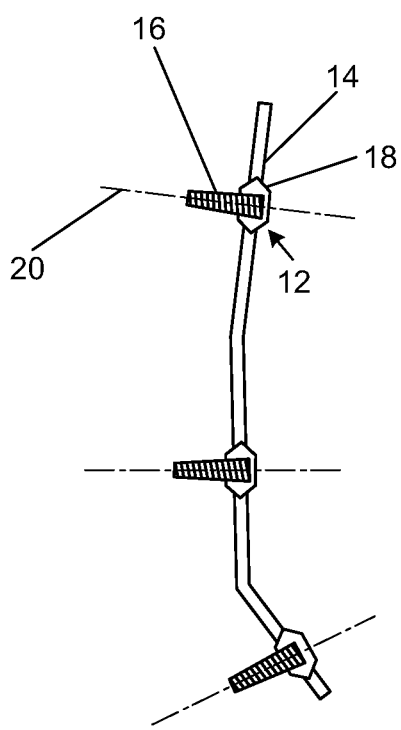
FIGS. 3 and 4 illustrate simplified variations of existing fixation systems.
Figure 4:
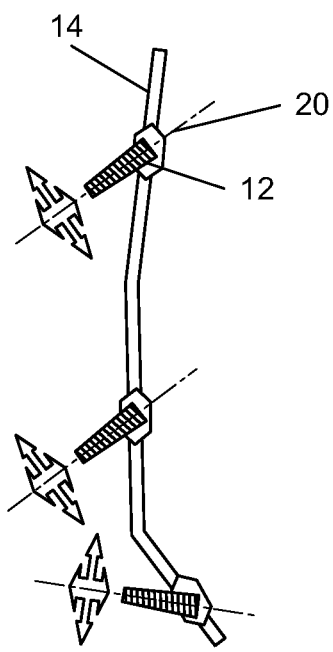
Figure 5:
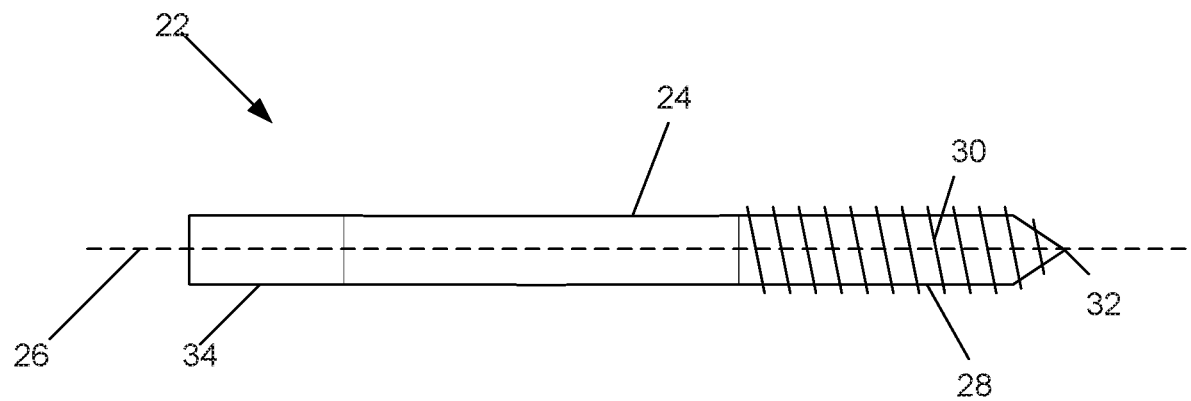
FIG. 5 illustrates a variation of the expandable attachment device in a radially contracted configuration.

FIG. 5 illustrates that the expandable attachment device 22 can have an unexpandable section 28 at a proximal end, an expandable section 24 at a medial length along the expandable attachment device 22, and a distal end 34. In other variations of the expandable attachment device, the unexpandable section 28 can be distal to the expandable section 24, and/or the expandable attachment device 22 can have more than one expandable section 24 and/or unexpandable section 28 that can be interspersed with each other.

The expandable attachment device 22 can have an expandable attachment device axis 26. The expandable device axis 26 can be substantially straight or curved.

The proximal end of the expandable attachment device can have a tip 32. The tip 32 can be sharpened or otherwise configured to seat the expandable attachment device in bone (e.g., having cutting teeth). The unexpandable section 28 can have unexpandable thread 30, for example, configured to screw the expandable attachment device 22 into bone.

Figure 6:
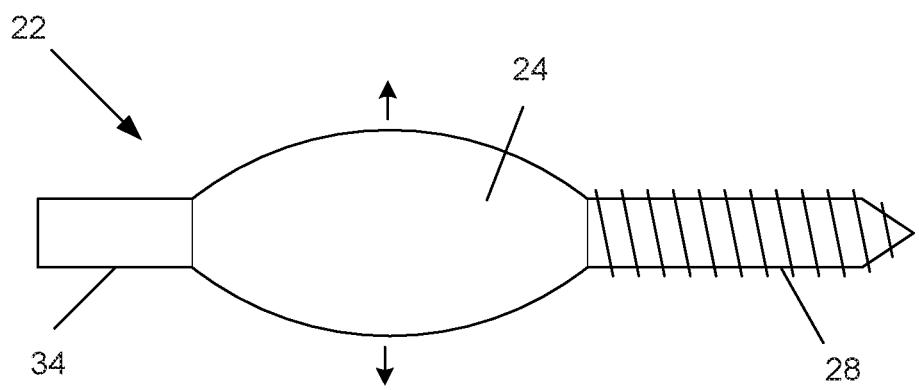
FIG. 6 illustrates the variation of the expandable attachment device in a radially expanded configuration.

FIG. 5 shows that the expandable attachment device 22 can have a radially contracted configuration. FIG. 6 illustrates that the expandable attachment device 22 can have a radially expanded configuration. For example, the expandable section can be radially expanded, as shown by arrows.

The expandable section 24 can be resiliently and/or deformably expandable. The expandable sections 24 can be radially expanded by axial compression (e.g., see FIGS. 8-11), rotation (e.g., see FIGS. 26-29), use of a lever such as a wedge, ramp or jack (e.g., see FIGS. 58-64), or combinations thereof.

The expandable section 24 can be biased to resiliently radially expand. For example, the expandable section 24 can be self-expandable or releasable spring. The expandable section 24 can be resiliently radially expandable and can be additionally deformably radially expandable to a larger radius than achieved by resilient expansion alone.

The expandable section 24 can have one or more anchors extending radially therefrom when the expandable section is in the radially expanded configuration. The anchors can be brads, hooks, pins, teeth, fasteners, pegs, screws, skewers, spikes, stakes, or combinations thereof.

Figure 7:
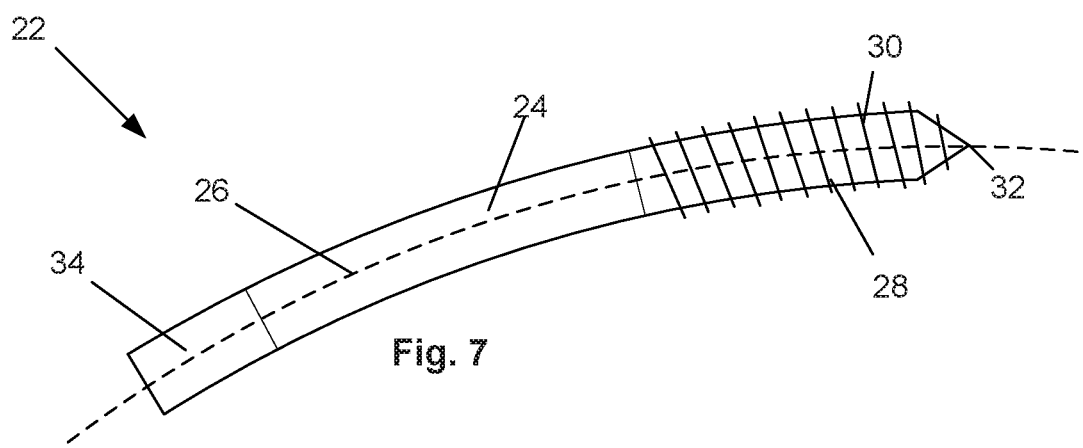
FIG. 7 illustrates a variation of the expandable attachment device in a radially contracted configuration.

FIG. 7 illustrates that the expandable attachment device axis 26 can be curved. The expandable attachment device axis 26 can have curved and straight lengths. For example, the expandable attachment device axis 26 can have a substantially straight length along the unexpandable section 28 and the distal end 34, and a curved length along the expandable section 24.

FIGS. 8 and 9 illustrates that the expandable attachment device 22 can be radially expanded by applying a proximally-directed force to the distal end 34 as shown by arrows of FIG. 8. The proximally-directed force can be substantially parallel to the expandable attachment device axis 26. The proximal force can be opposed by a distal force applied, for example, by the bone and/or a deployment tool. The expandable section can then radially expand, as shown by arrows in FIG. 9.

FIGS. 10 and 11 illustrate that the expandable attachment device 22 can have expandable thread 66 on the expandable section and unexpandable thread 30 on the unexpandable section. The expandable thread can radially expand with the remainder of the expandable section. The expandable attachment device shown in FIGS. 10 and 11 can be radially expanded by the method as shown in FIGS. 8 and 9.

FIGS. 12 and 13 illustrate that the expandable attachment device can be radially expanded by applying a distally-directed force to the distal end as shown by arrow. The distally-directed force can be substantially parallel to the expandable attachment device axis. The distal force can be opposed by a proximal force applied, for example, by the bone and/or a deployment tool. The expandable section can then radially expand, as shown by arrows in FIG. 13.

FIGS. 14 and 15 illustrate that the expandable attachment device can have expandable thread on the expandable section and unexpandable thread on the unexpandable section. The expandable thread can radially expand with the remainder of the expandable section. The expandable attachment device shown in FIGS. 14 and 15 can be radially expanded by the method as shown in FIGS. 12 and 13.

Figure 16:
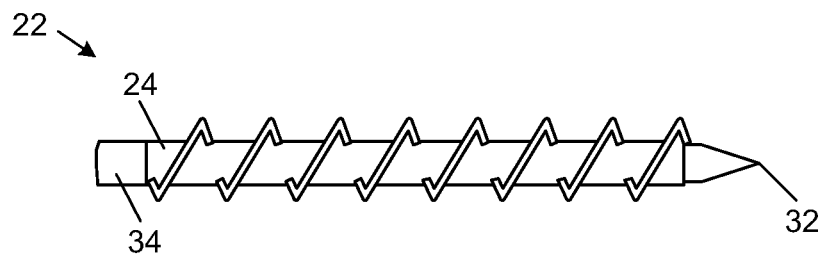
FIGS. 16 and 17 illustrate a variation of the expandable attachment device and a method for radially expanding the device.
Figure 17:
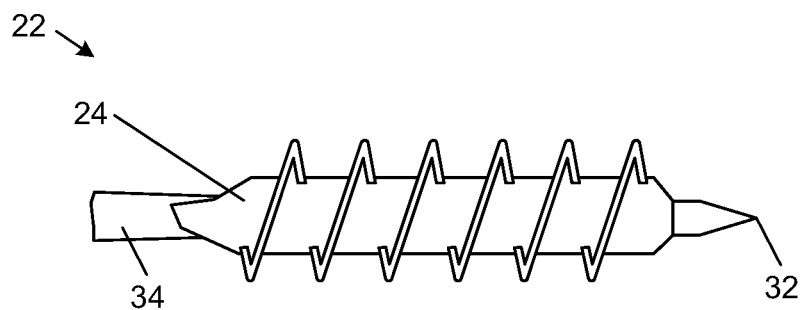
Figure 18:
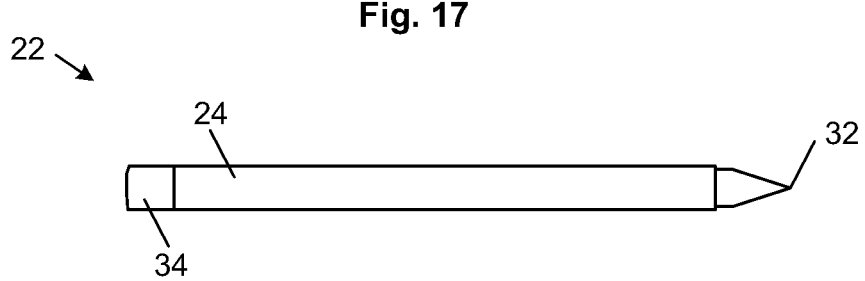
FIG. 18 illustrates a variation of the expandable attachment device in a contracted configuration.
Figure 19:
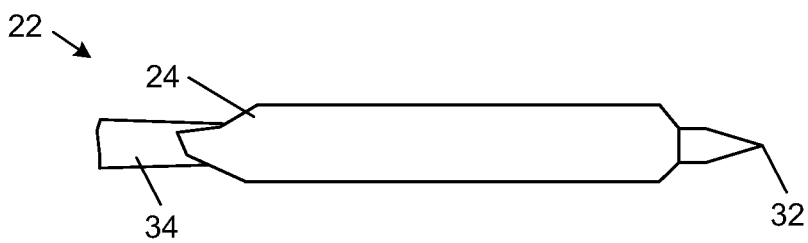
FIGS. 19 and 20 illustrate variations of the expandable attachment device of FIG. 18 and methods for radially expanding the device.

FIG. 16 illustrate that substantially the entire length of the expandable attachment device can be the expandable section. The distal end can extend distally from the expandable section. FIG. 17 illustrates that the entire expandable section can radially expand. FIGS. 16 and 17 illustrate that the expandable section can have expandable thread. FIGS. 18 and 19 illustrate the variation of the expandable attachment device of FIGS. 16 and 17, respectively, without expandable thread.

Figure 20:
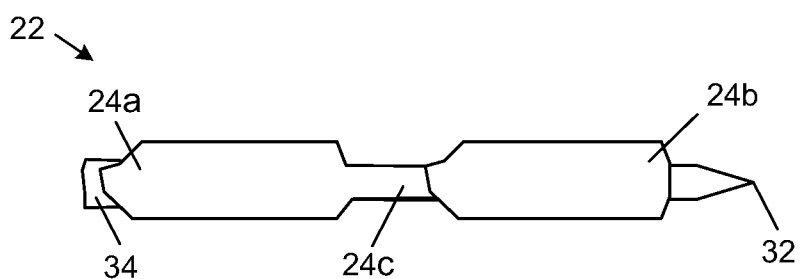

FIG. 20 illustrates that the expandable attachment device can have, from distal to proximal, a first expandable section, a third expandable section, and a second expandable section. The first, second and third expandable sections can radially expand at different rates (e.g., under different deployment loads, for example one or more are resiliently and one or more are deformably expandable). For example, the first and second expandable sections can radially expand at the same rate, and the third expandable section can radially expand at a lesser rate.

Figure 21:
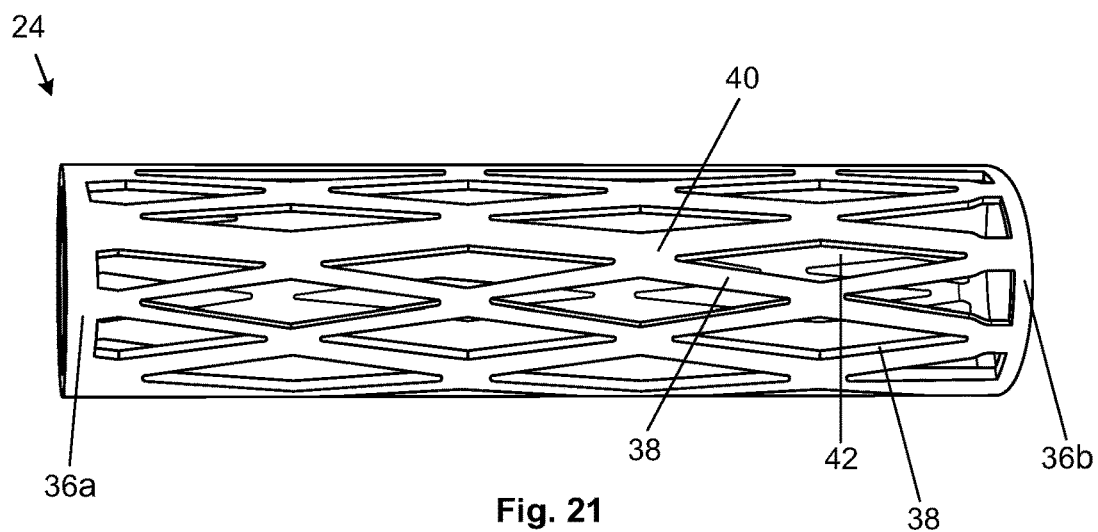
FIG. 21 illustrates a variation of the expandable section in a radially contracted configuration.

FIG. 21 illustrates that the expandable section 24 can have a number of struts 38 attached to each other at joints 40. When the expandable section 24 is in a radially contracted configuration, the struts 38 can be configured to form diamond-shaped ports 42. The expandable section 24 can have a distal hoop 36b at the distal end and/or a proximal hoop 36a at the proximal end. The hoops 36 can attach to all of the struts 38 at the respective end. The hoops 36 and struts 38 can all be integral with and/or attached to each other.

Figure 22:
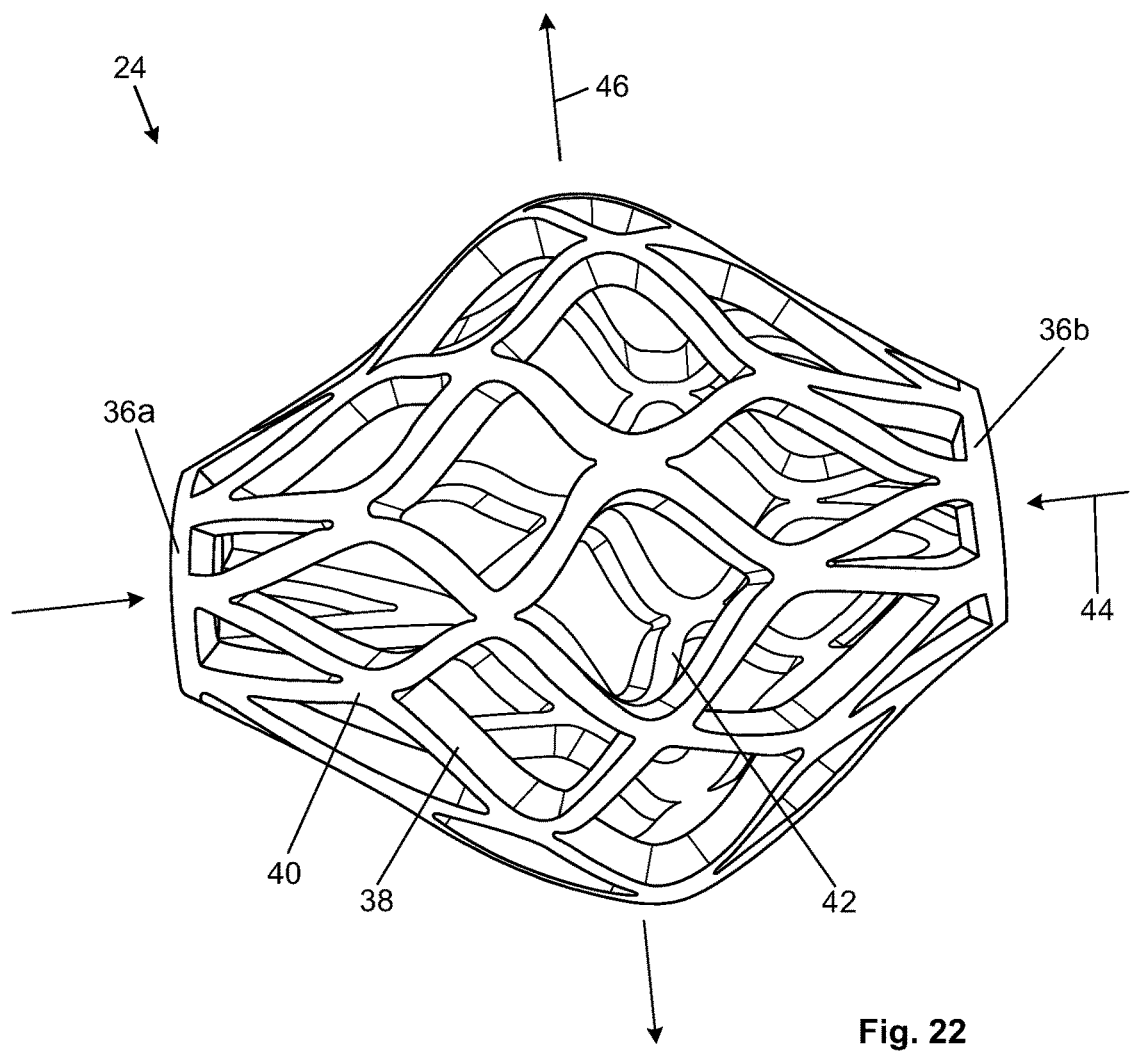
FIG. 22 illustrates the expandable section of FIG. 21 in a radially expanded configuration.

FIG. 22 illustrates that longitudinal compressive force 44 can be applied to the expandable section, for example resulting in radial expansion 46. In a radially expanded configuration, the struts can deform near the joints. The hoops can remain substantially static.

Figure 23:
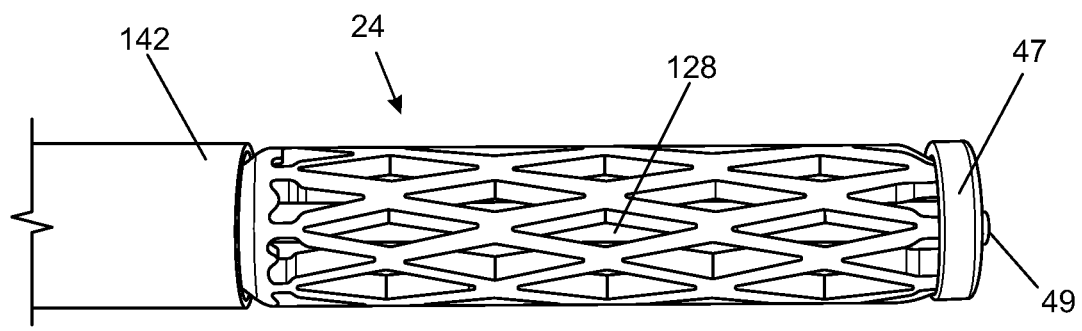
FIG. 23 illustrates a variation of the expandable section in a radially contracted configuration on the expandable attachment device.
Figure 24:
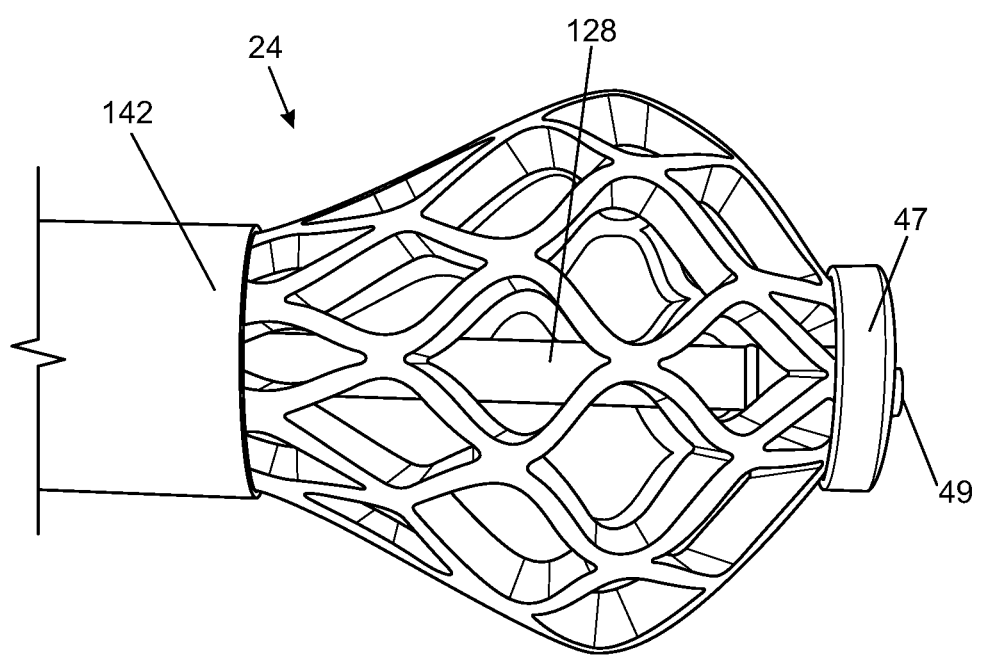
FIG. 24 illustrates a variation of the expandable section in a radially expanded configuration on the expandable attachment device.

FIGS. 23 and 24 illustrates that the expandable section can be radially expanded by longitudinally compressing the expandable section. For example, the deployment tool 60 (or expandable attachment device 22) can have an anvil 142 and a deployment cap 47. The anvil 142 can be the distal end and/or the unexpandable section. The deployment cap 47 can be part of or attached to the unexpandable section and/or the distal end, for example, the opposite of the anvil 142. The expandable section can be compressed between the anvil 142 and the deployment cap 47.

The deployment tool 60 (or expandable attachment device 22) can have a deployment rod 128, for example to transmit the compressive force to the deployment cap 47. The deployment rod 128 can be releasably attached to the deployment cap 47, for example via a releasable deployment anchor 49. The releasable deployment anchor can be released and the deployment rod can be removed after the expandable section is radially expanded.

Figure 25E:
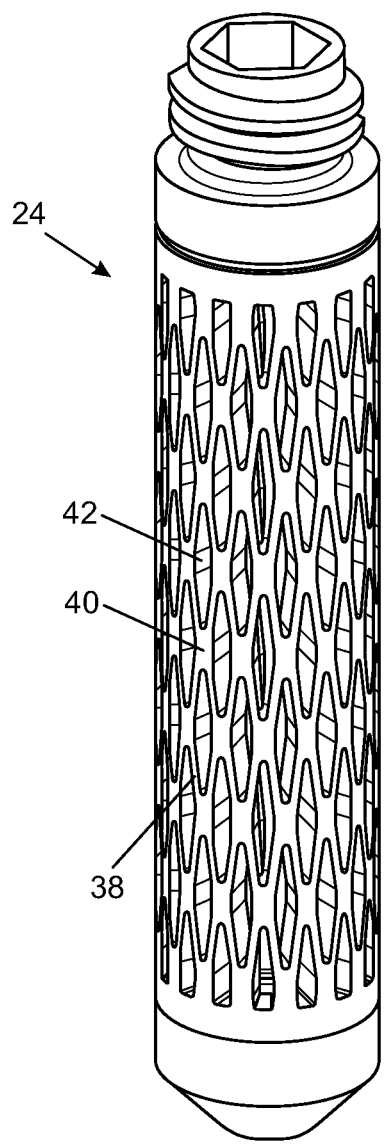

FIGS. 25a-e illustrate variations of the expandable section's strut, port and joint configuration. FIG. 25a illustrates that the ports can be larger near a central region 54 near the longitudinal median of the expandable section than in end regions 52. The lengths of the expandable section with larger ports can radially expand during longitudinal compression before the lengths of the expandable section with smaller ports. The expandable section can have thread 50 and/or another releasable attachment configuration at one or both ends. The expandable section can have a tool port 48 configured to receive a deployment tool (e.g., a deployment rod) through the proximal end of the expandable section.

FIG. 25b illustrates that the struts and ports can be substantially identical along the entire length of the expandable section. FIG. 25c can have main struts 56 and smaller folded cross-struts 58 that attach to multiple main struts 56. FIG. 25d illustrates that the struts and ports can be substantially identical along the entire length of the expandable section and that the ports can be longer in the longitudinal direction that in the angular direction, with respect to the expandable section. FIG. 25e that the struts and ports can be substantially identical along the entire length of the expandable section and that the ports can be longer in the longitudinal direction that in the angular direction, with respect to the expandable section, and smaller and more numerous than as shown in FIG. 25d.

Figure 26:
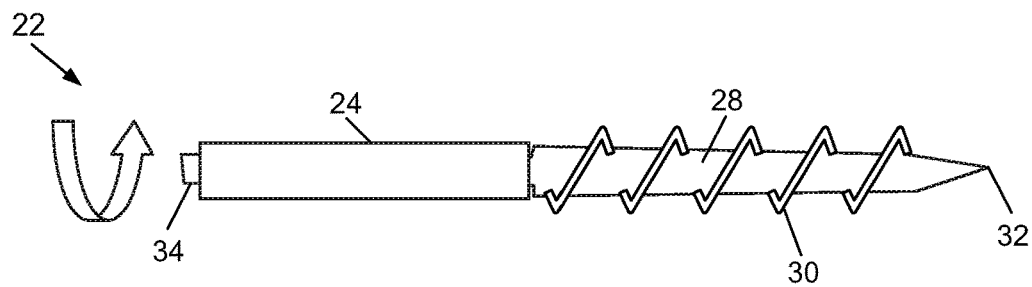
FIGS. 26 and 27 illustrate a variation of the expandable attachment device and a method for radially expanding the device.
Figure 27:
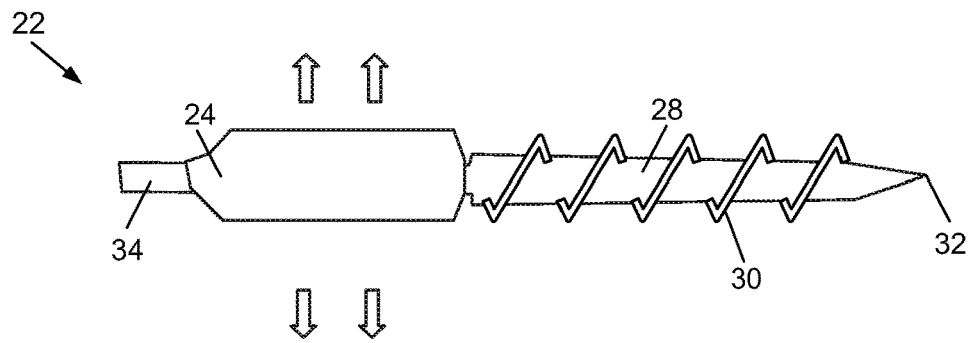

FIGS. 26 and 27 illustrate that when the distal end and/or expandable section is rotated, as shown by arrow in FIG. 26, that the expandable section can radially expand, as shown by arrows in FIG. 27. FIGS. 26 and 27 illustrate that the expandable section can be distal to the unexpandable section.

Figure 28:
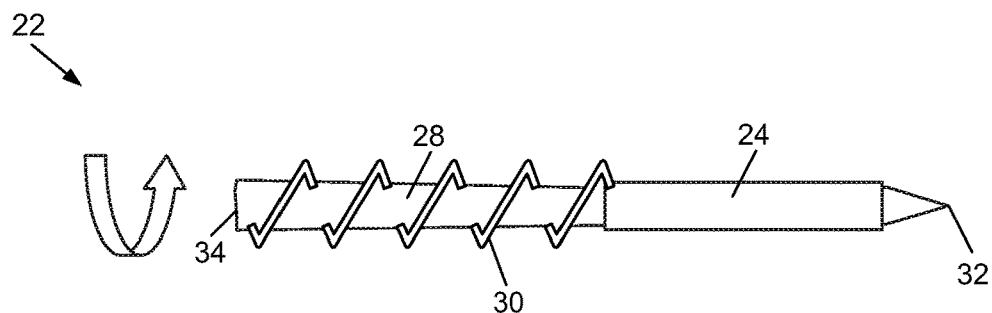
FIGS. 28 and 29 illustrate a variation of the expandable attachment device and a method for radially expanding the device.
Figure 29:
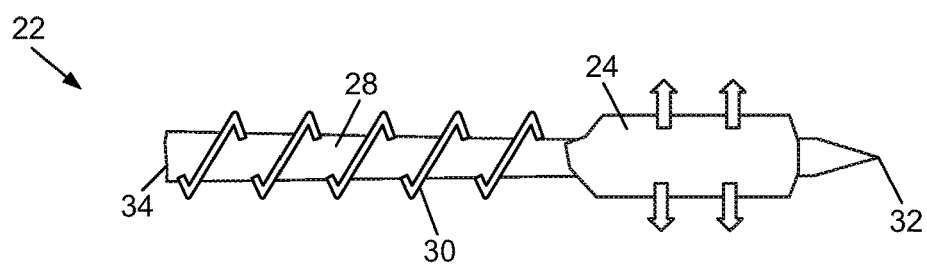

FIGS. 28 and 29 illustrate that when the distal end and/or expandable section is rotated, as shown by arrow in FIG. 28, that the expandable section can radially expand, as shown by arrows in FIG. 29. FIGS. 28 and 29 illustrate that the unexpandable section can be distal to the expandable section.

FIG. 30 illustrates that the expandable section can have a slot 62 radially through the expandable section. The slot 62 can have a helical configuration along the expandable section. The distal end can be threaded. The expandable attachment device can be detachably attached to a deployment tool 60.

FIG. 31 illustrates that the expandable section can have a textured surface. The expandable attachment device can have a distal end cap 64 at the distal end. The distal end cap can have a substantially spherical configuration.

Figure 32:
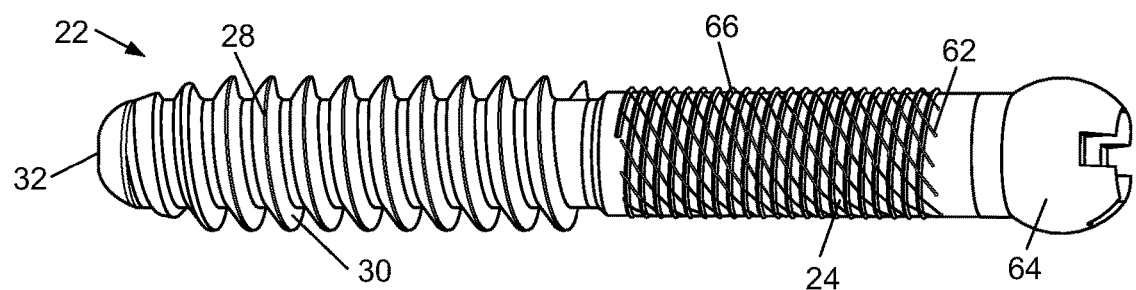
FIGS. 32 and 33 are side and end perspective views, respectively, of a variation of the expandable attachment device.
Figure 33:
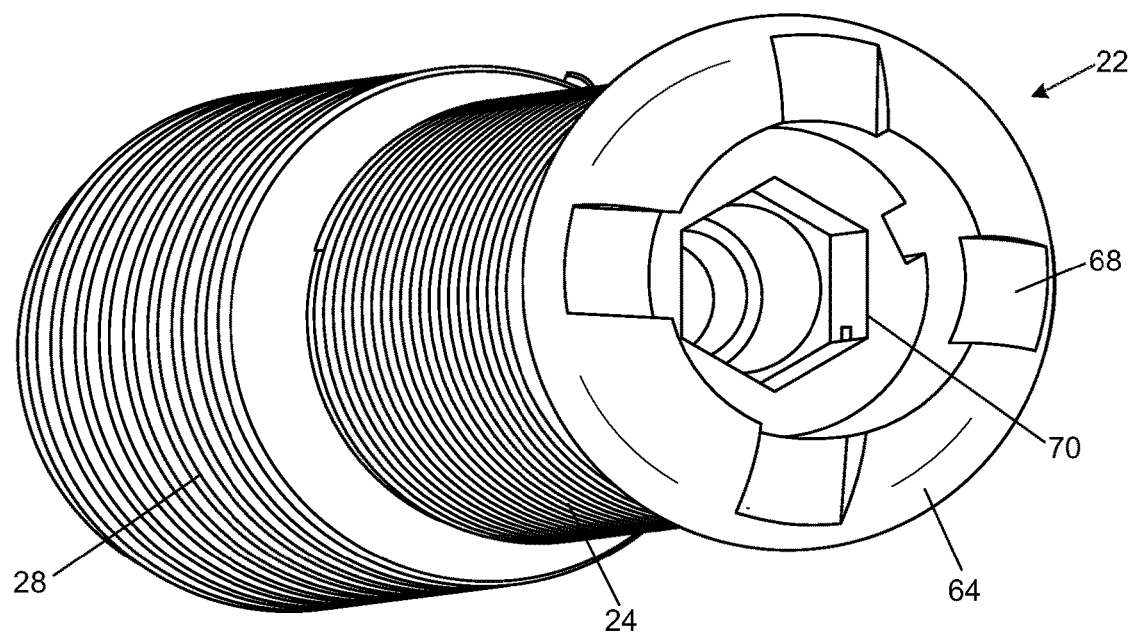

FIG. 32 illustrates that the expandable section can have a helical slot 62 and an expandable thread 66. The expandable thread 66 can be helical at substantially the opposite angle of the helical slot 62. The expandable thread can be helical at a positive or negative angle with respect to a plane perpendicular to the expandable attachment device axis. The helical slot can be helical at the opposite-signed (i.e., positive or negative) angle to the expandable thread.

FIG. 32 illustrates that the distal end of the distal end cap can have cap deployment tool attachments 68, for example cross-notches on the head of the cap 64. The cross-notches can be utilized to engage the distal end cap 64 with an engagement tool.

The distal end of the center shaft can have a shaft deployment tool attachment 70, for example, an allen or hexagonal or septagonal socket.

Figure 34:
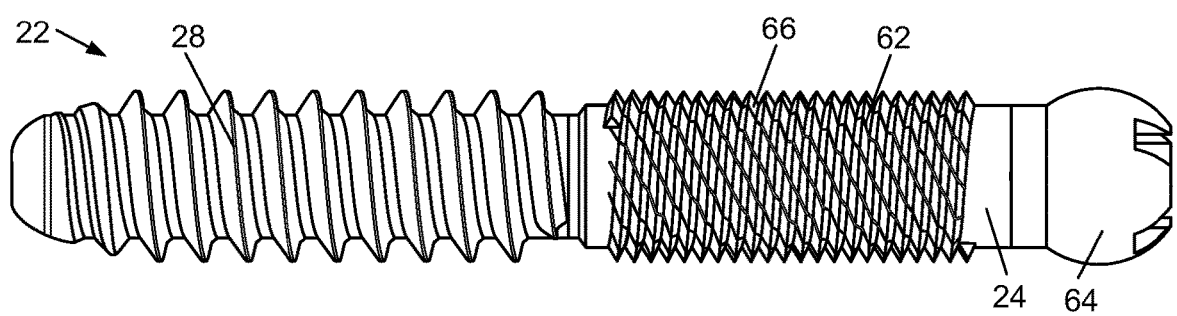
FIG. 34 is a side view of a variation of the expandable attachment device.

FIG. 34 illustrates that when the expandable section is in a radially contracted configuration, the expandable thread 66 can protrude to about the same radius at the unexpandable thread with respect to the expandable attachment device axis.

Figure 35A:
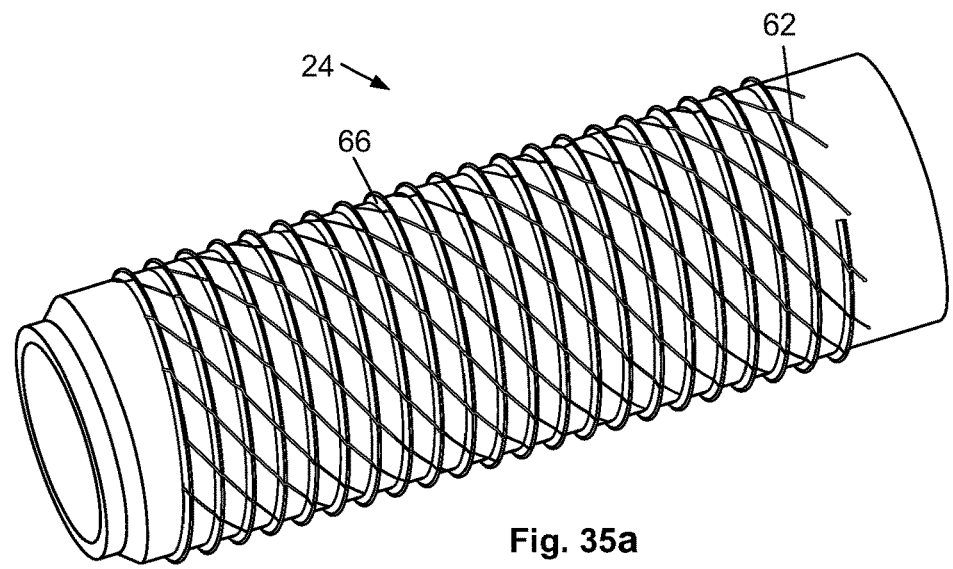
FIGS. 35a and 35b illustrate a variation of the expandable section.
Figure 35B:
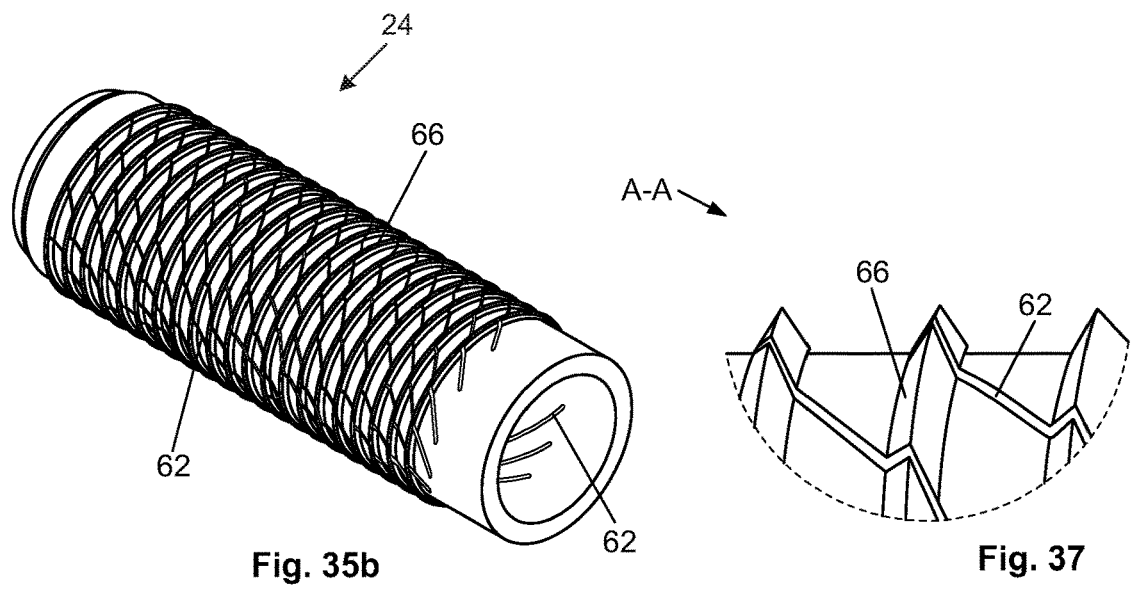
Figure 37:
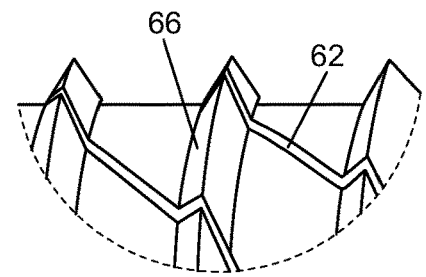
FIG. 37 is a variation of a close-up view of section A-A of FIG. 36.
Figure 36:
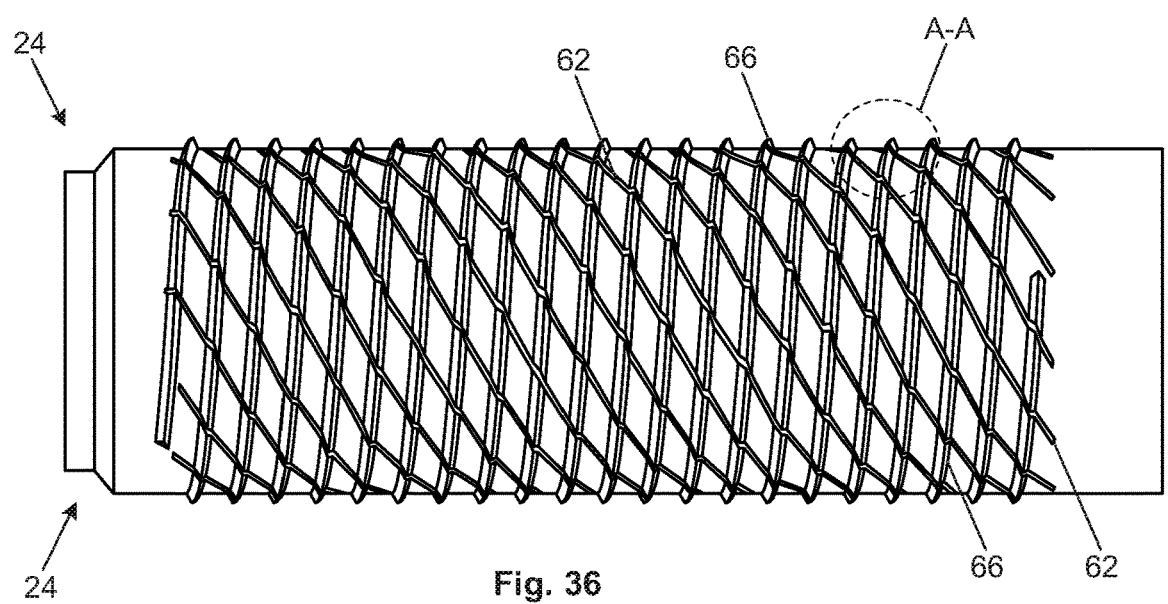
FIG. 36 is a side view of the expandable section of FIGS. 35a and 35b.

FIGS. 35a and 35 illustrate that the expandable section can be separate to the remainder of the expandable attachment device. FIG. 35b illustrates that the helical slot can extend through the thickness of the wall of the expandable section. FIGS. 36 through 39 illustrate additional details of the expandable section.

Figure 38:
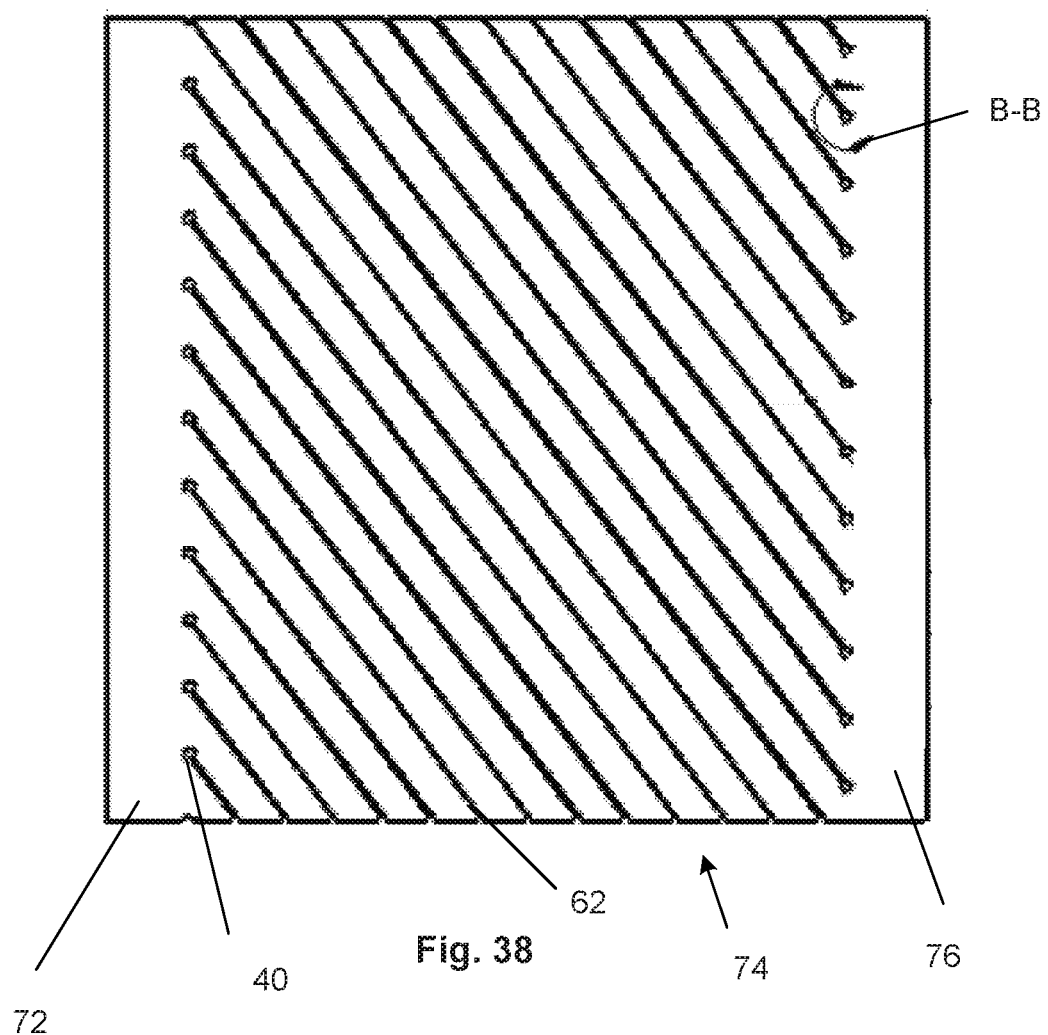
FIG. 38 is a flattened view of a variation of the expandable section.

FIG. 38 illustrates that the expandable section can have an expandable section wall 72 can have numerous helical slots in a slotted wall section 74. The expandable section wall can have one or more unslotted wall sections 76, for example at the distal and proximal ends of the expandable section. The slots can have joints at one both ends of the slots.

Figure 39:
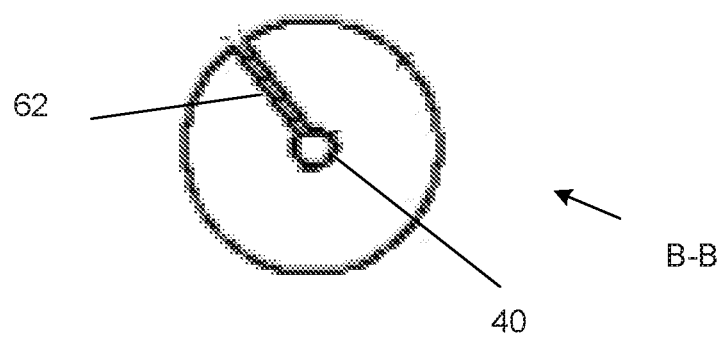
FIG. 39 is a variation of a close-up view of section B-B of FIG. 38.

FIG. 39 illustrates that the joints can be circular. The joints can have a larger, smaller or equal diameter to the width of the slot.

Figure 40A:
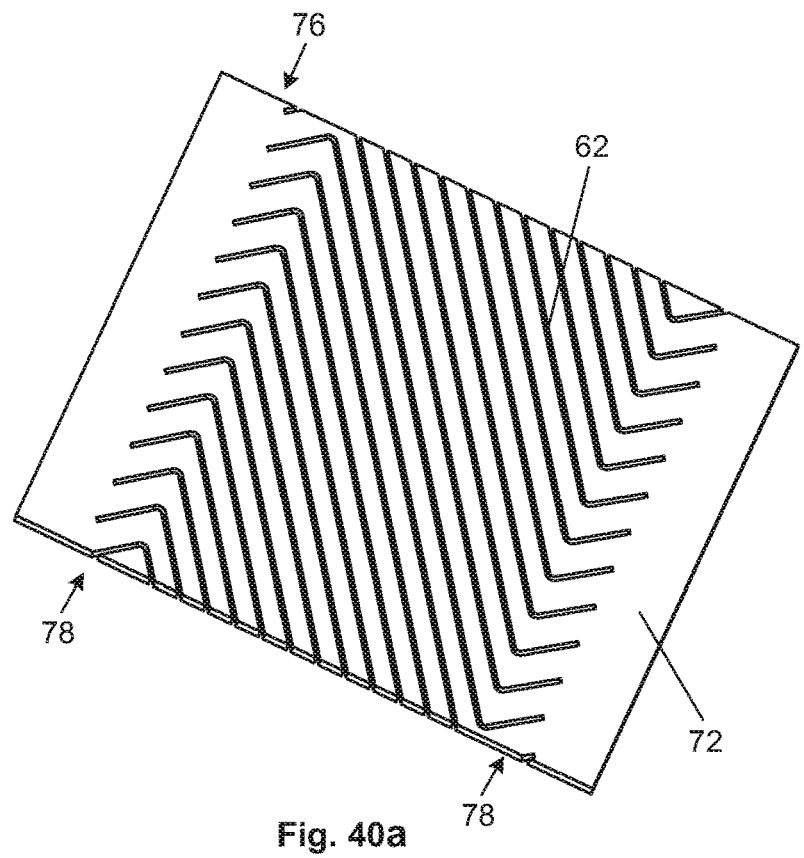
FIGS. 40a and 40b are flattened views of variations of the expandable section.

FIG. 40 illustrates that the expandable section wall can have one or more retrograde slot sections 76, for example at each end of the slotted wall section 74. The retrograde slot section 76 can have slots 62 in the substantially opposite direction of the slots 62 in the remainder of the slotted wall section 74. The primary (i.e., non-retrograde) slots can be helical at a positive or negative angle with respect to a plane perpendicular to the expandable attachment device axis. The retrograde slots can be helical at the opposite-signed (i.e., positive or negative) angle to the primary slots.

The retrograde slot section 76 can, for example, act as a shock absorber. The retrograde slot section 76 can increase maximum radial expansion of the expandable section. The slots 62 can be sinusoidal along the length of the expandable section.

Figure 40B:
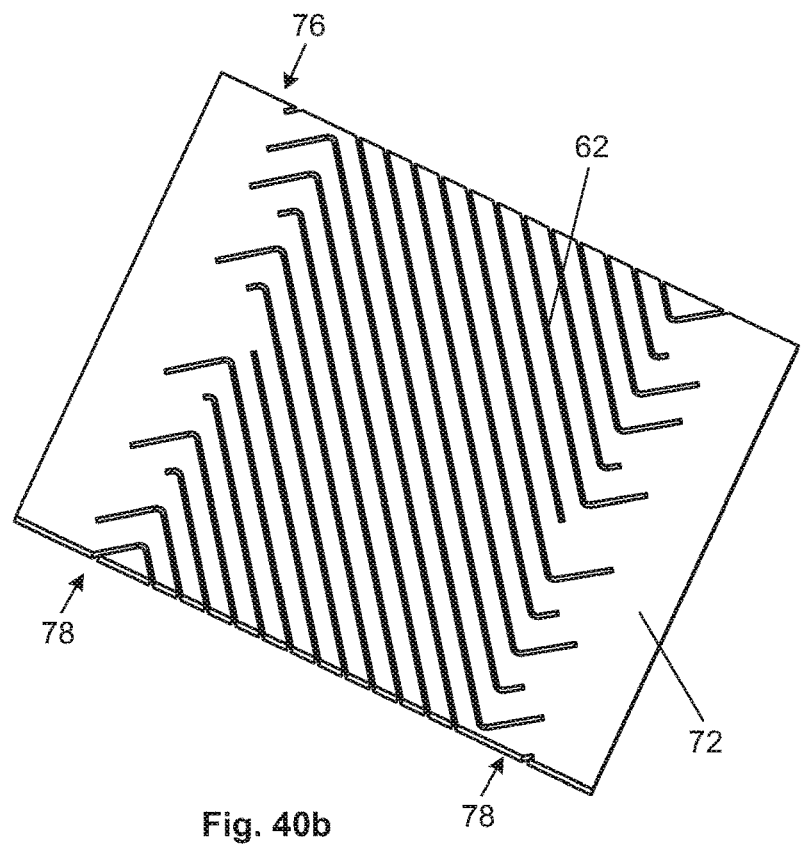

FIG. 40b illustrates that the ends of the slots 62 can be placed at different lengths from the ends of the expandable section. For example, varying the lengths of adjacent slots can diffuse strain on the expandable section.

FIGS. 41 through 45 illustrate dimensions of the expandable section (dimensions are shown on attachment B).

FIG. 41 illustrates that the unexpandable section can be integral with a center shaft and the distal end.

FIG. 43 illustrates that the distal end can have the shaft deployment tool attachment therethrough.

Figure 46:
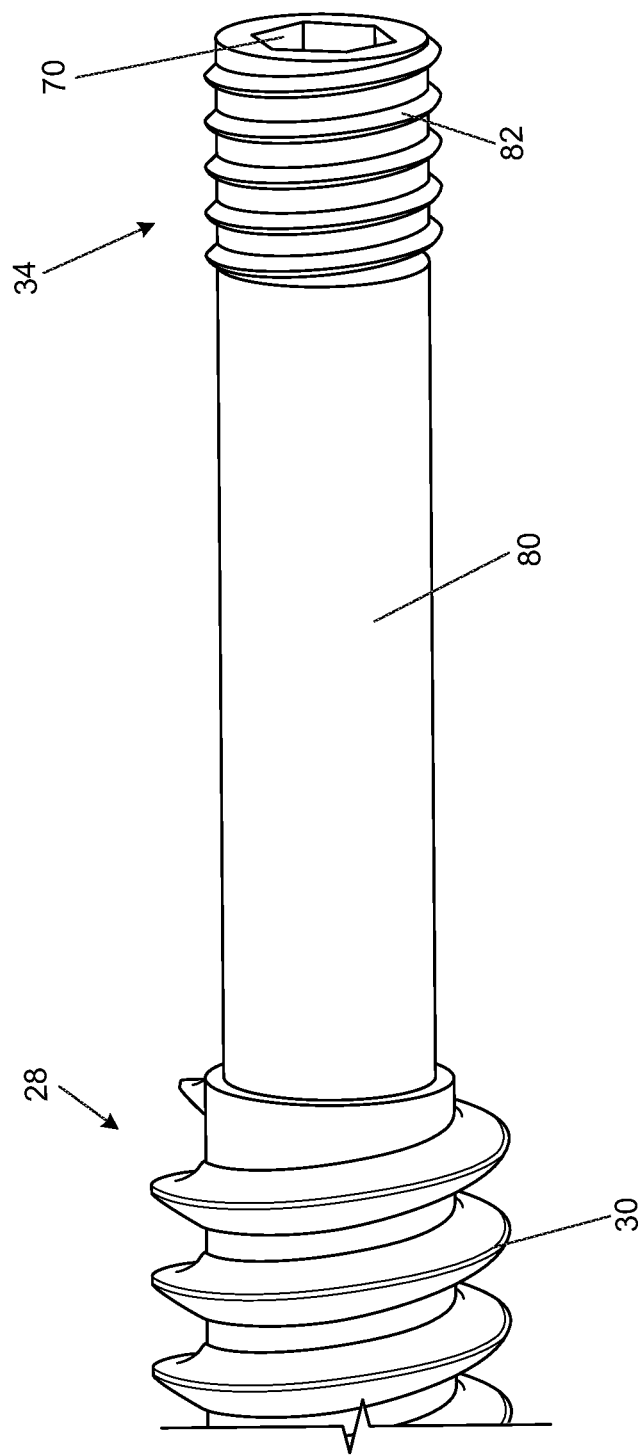
FIG. 46 illustrates a variation of the center shaft integral with the unexpandable section and the distal end.

FIG. 46 illustrates a close up of the distal end of the unexpandable section, center shaft and distal end.

Figure 47A:
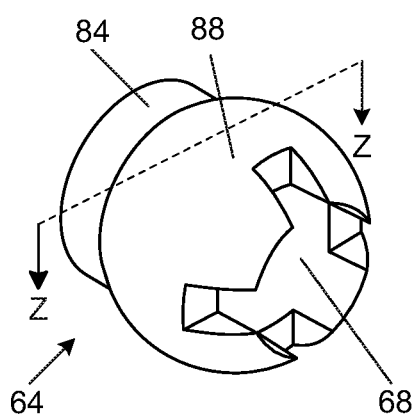
FIGS. 47a and 47b are various perspective views of a variation of the distal end cap.
Figure 47B:
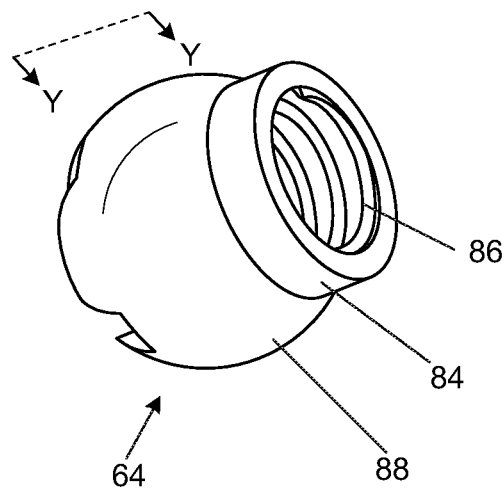
Figure 48:
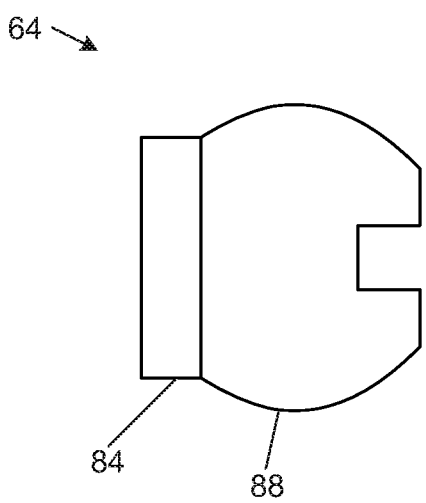
FIG. 48 is a side view of a variation of the distal end cap.
Figure 49:
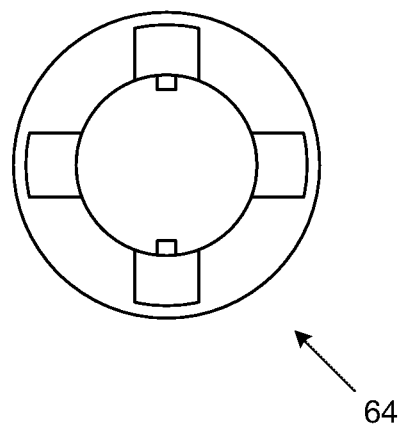
FIG. 49 is a distal end view of a variation of the distal end cap.
Figure 50:
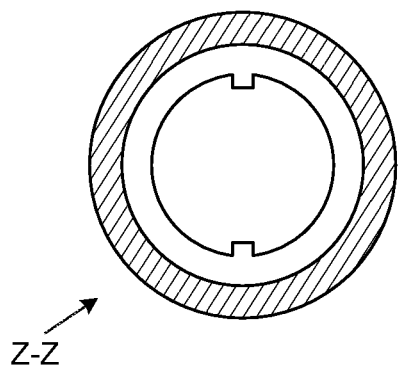
Figure 51:
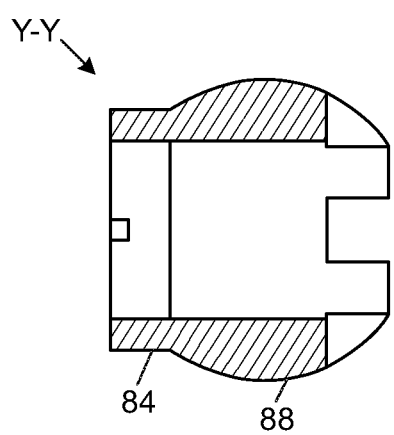
FIG. 51 illustrates a variation of cross-section Y-Y of FIG. 47b.

FIGS. 47a and 47b illustrate that the distal cap end can have a cap ball and a cap sleeve. The cap ball and/or cap sleeve can have internal cap thread along all or part of the length.

FIGS. 48 through 51 illustrate dimensions of the expandable section (dimensions are shown on attachment C).

Figure 52:
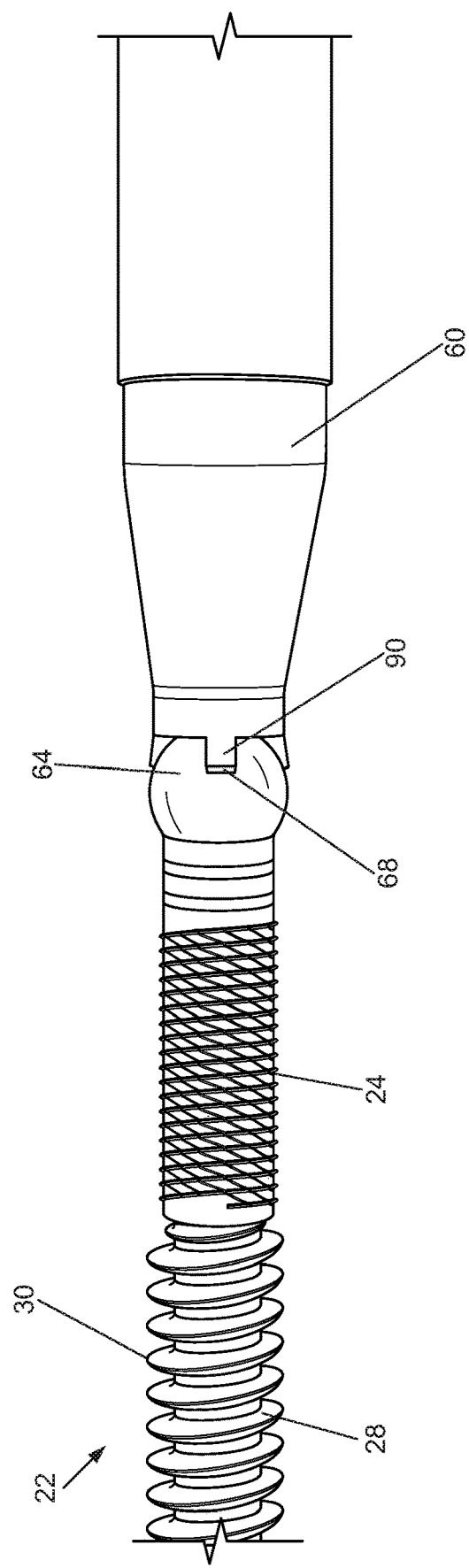
FIG. 52 illustrates a variation of the expandable attachment device attached to a variation of the deployment tool.

FIG. 52 illustrates that the expandable attachment device can be releasably attached to the deployment tool. The deployment tool can have deployment engagement teeth that can align and intersect with the distal end cap, for example at the cap deployment tool attachments.

FIG. 53 illustrates that the expandable attachment device can be dissembled in separate elements. For example, the unexpandable section can be integral with the center shaft. The center shaft, for example at the distal end, can have shaft cap attachments that can attach to the distal end cap.

FIG. 54 illustrates that the expandable attachment device can be assembled by translating the expandable section over the center shaft, as shown by arrow. The distal end cap can then be rotated, as shown by arrow, onto the shaft cap attachments.

FIGS. 55 and 56 illustrate that the deployment tool can have a post tool and a tooth tool. The tooth tool can be separate, attached, or integral with the post tool.

The post tool can have a post tool hand. The post tool handle can be attached to or integral with a deployment engagement post. The post tool can have a deployment tool suspension. The deployment engagement post can be configured to attach to the shaft deployment tool attachment.

The tooth tool can have deployment engagement teeth. The deployment engagement teeth can be configured to attach to the cap deployment tool attachment. The tooth tool can have a tooth tool handle, for example extending radially from the remainder of the tooth tool.

The deployment tool suspension can resiliently separate the tooth tool and the post tool. The deployment tool suspension can suspend the deployment engagement post from the post tool handle.

Figure 57:
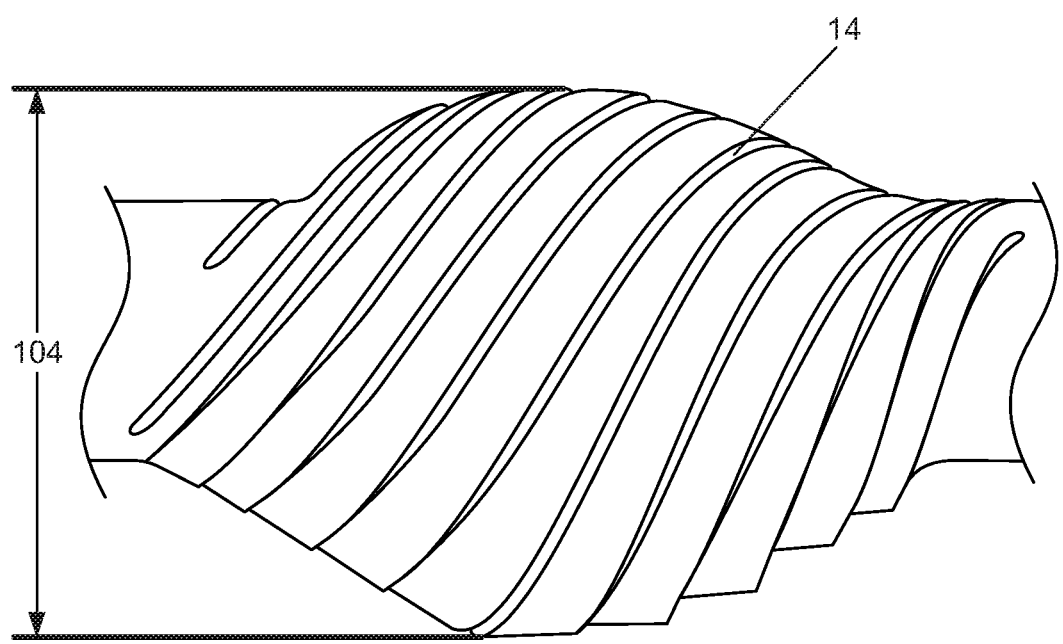
FIG. 57 illustrate variations of the expandable attachment device in radially expanded configurations, and measurements thereof.

FIG. 57 illustrates the expandable section in a radially expanded configuration can have an outer diameter 104 from about 7 mm (0.3 in.) to about 15 mm (0.59 in.), for example about 9.99 mm (0.393 in.) or about 9.31 mm (0.367 in.).

Figure 58:
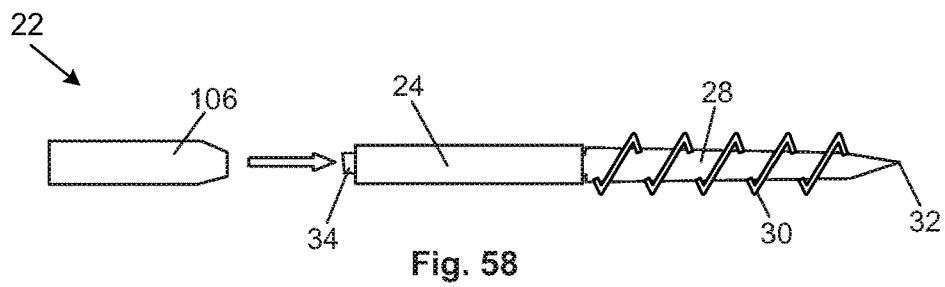
FIGS. 58 and 59 illustrate a variation of the expandable attachment device and a method for radially expanding the device.
Figure 59:
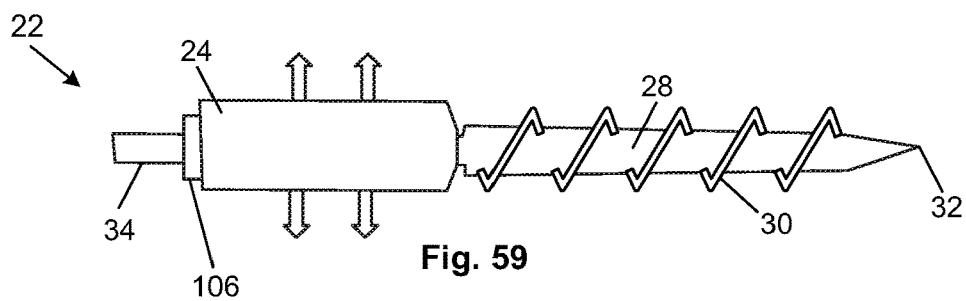

FIGS. 58 and 59 illustrate that an external wedge can be inserted, as shown by arrow in FIG. 58, into the expandable section. The expandable section can then radially expand, as shown by arrows in FIG. 59. The external wedge can be left in the expandable section or removed from the expandable section. The wedge can have a transverse cross section that is square, round (e.g., a conical wedge), rectangular, oval, or combinations thereof.

Figure 60:
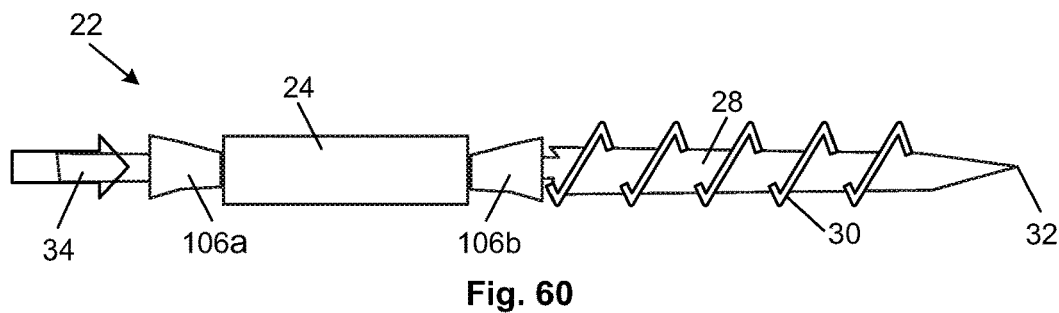
FIGS. 60 and 61 illustrate a variation of the expandable attachment device and a method for radially expanding the device.
Figure 61:
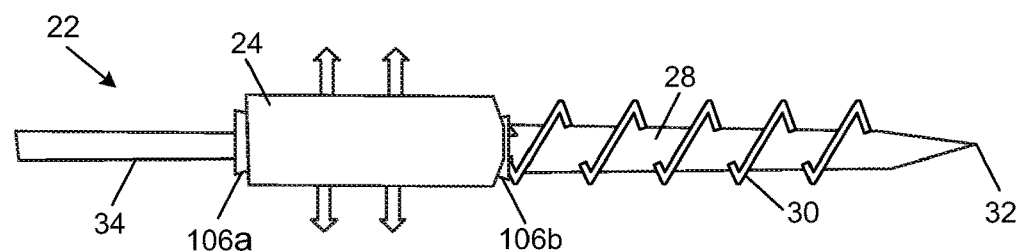

FIG. 60 illustrates that the expandable attachment device can have a first external wedge and a second external wedge. The second external wedge can be attached to or integral with the unexpanded section and/or otherwise positioned between the expandable section and the unexpanded section when the expandable section is in a radially contracted configuration. The second external wedge can be pointing narrow end-first toward the distal end of the expandable attachment device.

A proximally-directed force can be applied, as shown by arrow, to the first external wedge and/or the distal end. The expandable section can then radially expand, as shown by arrows in FIG. 61, as the wedges are pushed into a channel in the expandable section.

Figure 62:
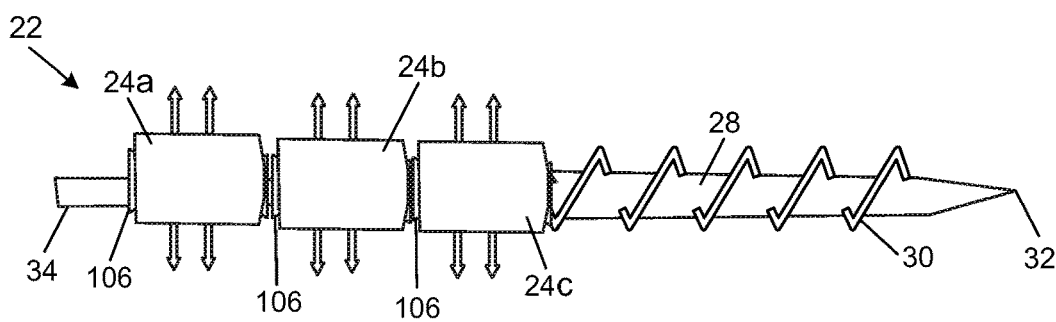
FIG. 62 illustrates a variation of the expandable attachment device and a method for radially expanding the device.

FIG. 62 illustrates that the expandable attachment device can have a first expandable section, second expandable section, and third expandable section. The expandable sections can each have one or two external wedges entering into an inner hollow or channel, as shown in FIGS. 58 through 61.

Figure 63:
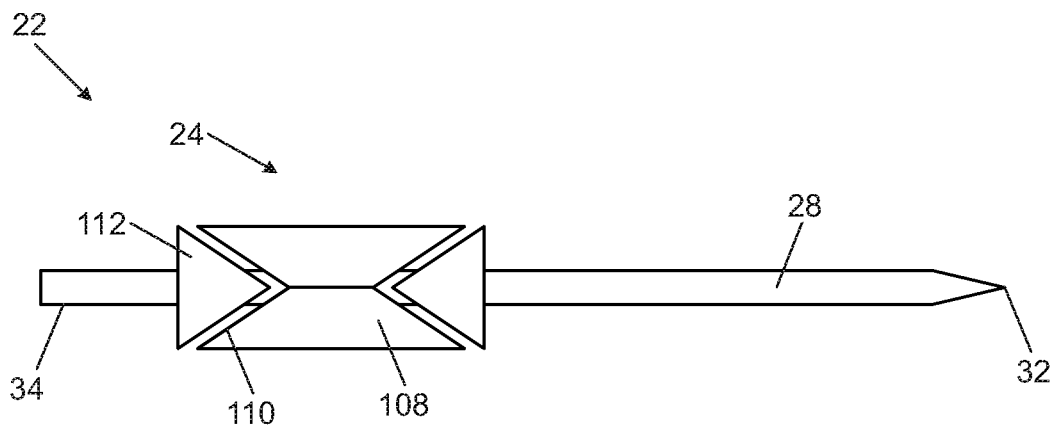
FIGS. 63 and 64 illustrate a variation of the expandable attachment device and a method for radially expanding the device.

FIG. 63 illustrates that the expandable section can have one or more expansion elements configured to radially expand. The expandable section can have one, two or more internal wedges. The expansion elements can have ramps configured to slidably engage the internal wedge when the internal wedge is compressed into the expansion elements.

Figure 64:
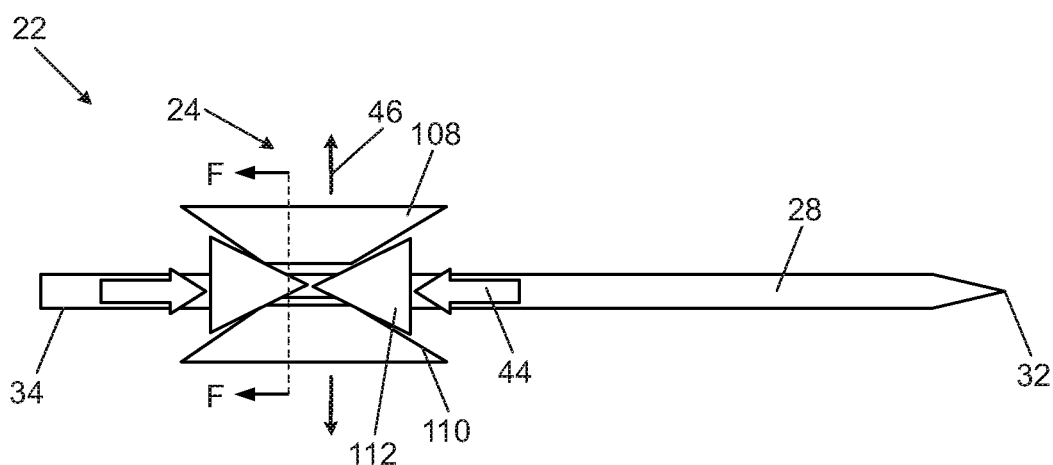

FIG. 64 illustrates that the internal wedges can be compressed, as shown by arrows, into the expansion elements. The expansion elements can then radially expand, as shown by arrows.

Figure 65:
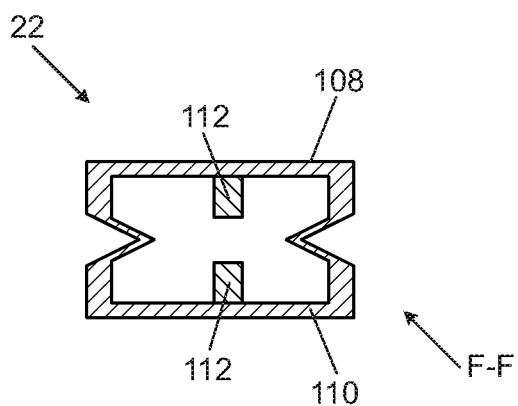
FIG. 65 illustrates a variation of cross-section F-F of FIG. 64.

FIG. 65 illustrates that the internal wedges can interference fit with the ramps. As the internal wedges are further compressed, the internal wedges can cause a deformation or other translation of the expansion elements.

Figure 66:
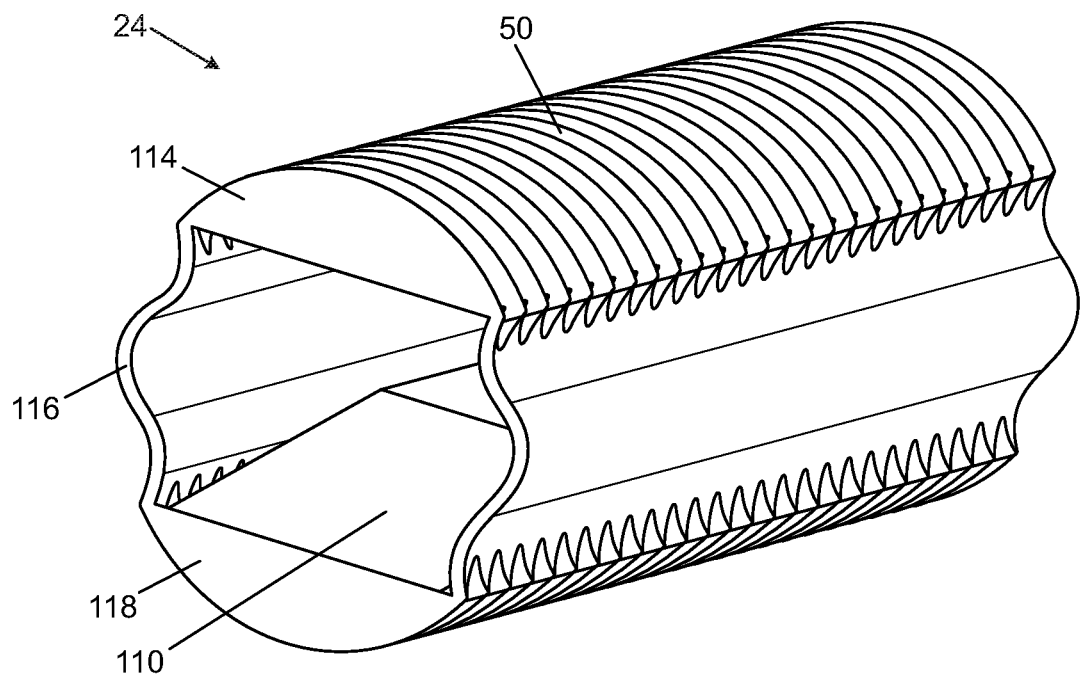
FIG. 66 is a perspective view of a variation of the expandable section in a radially contracted configuration.
Figure 67:
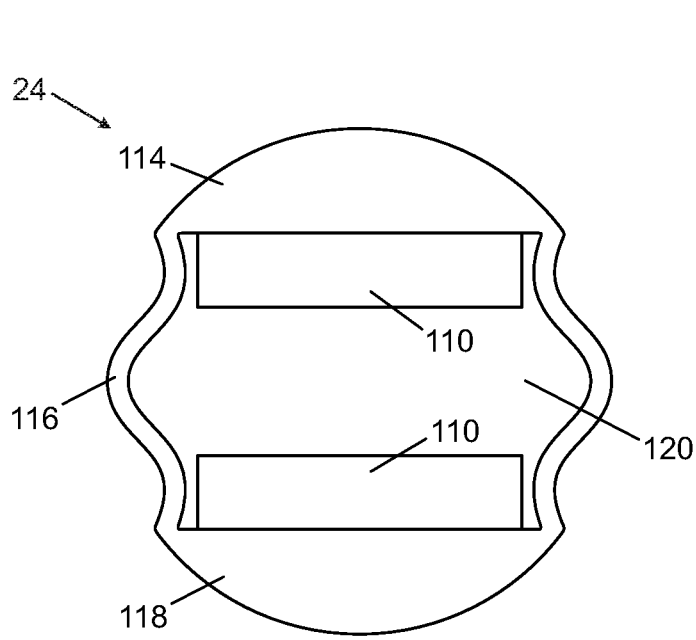
FIG. 67 is an end view of the variation of the expandable section of FIG. 66 in a radially contracted configuration.

FIGS. 66 and 67 illustrates that the expandable section can have a top wall and a bottom wall connected by two side walls. The top wall and bottom wall can have expandable thread. The side wall can have expandable thread. The top wall and/or bottom wall can have one or more ramps extending inwardly into the longitudinal channel of the expandable section.

Figure 68:
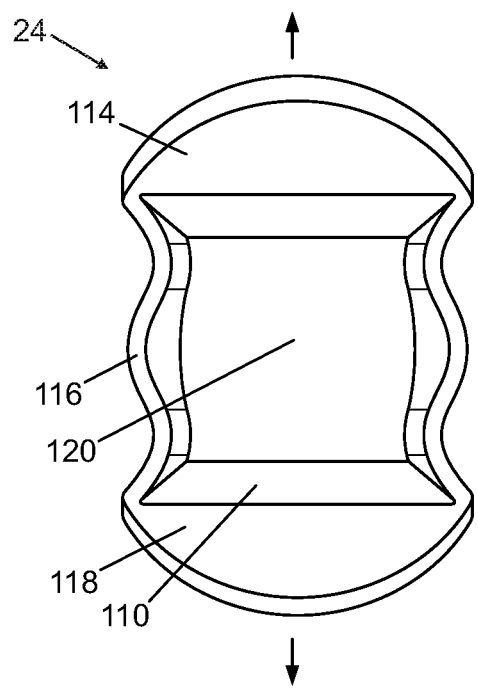
FIG. 68 is an end view of the variation of the expandable section of FIG. 66 in a radially expanded configuration.

FIG. 68 illustrates that in a radially expanded configuration, the top wall and bottom wall can translate radially outward, as shown by arrows. The side walls can deform and/or translate radially inward.

Figure 69:
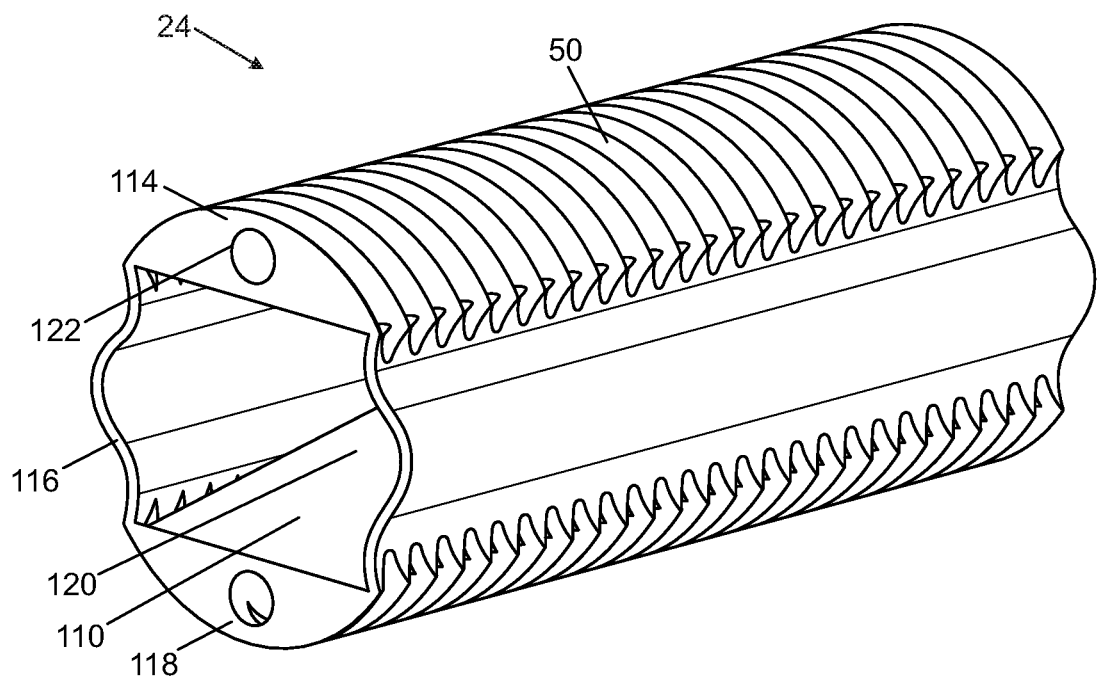
FIGS. 69 and 70 are perspective views of variations of the expandable section.

FIG. 69 illustrates that the top wall and/or bottom wall can have a manipulation channel passing completely or partially therethrough in a substantially longitudinal direction. The manipulation channels can be, for example, cylindrical.

Figure 70:
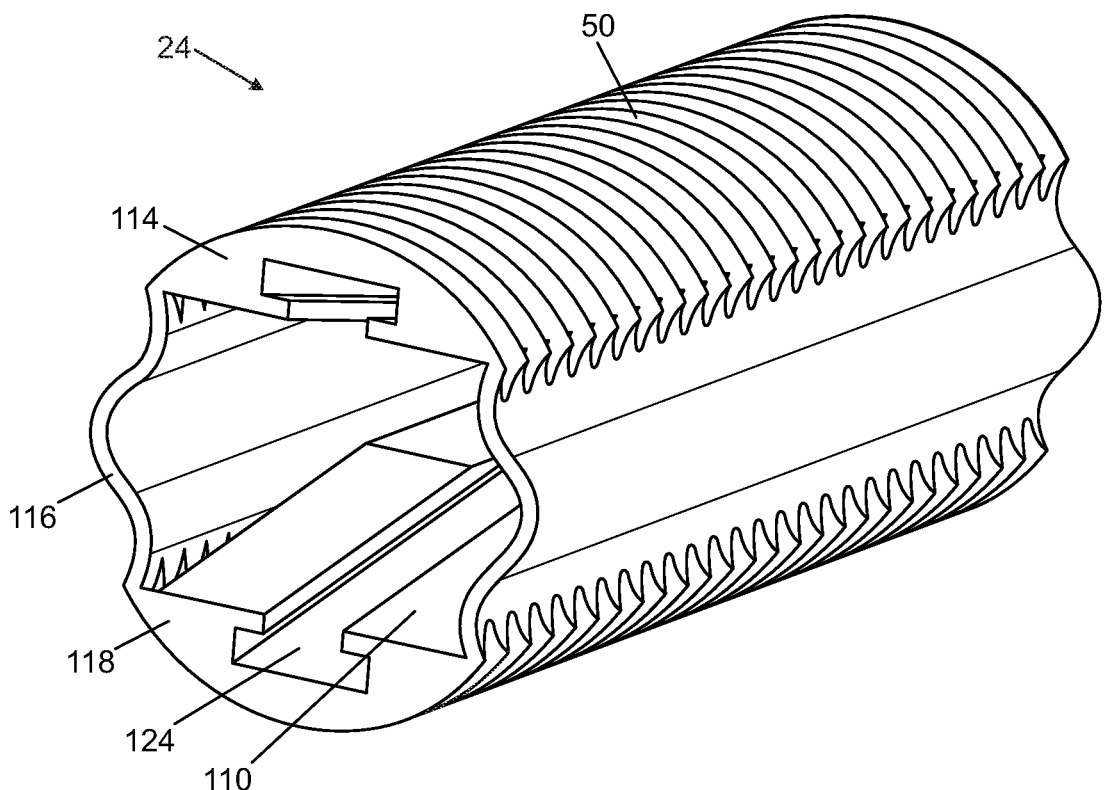

FIG. 70 illustrates that the top wall and/or the bottom wall can have longitudinal guide slots 124. The guide slots 124 can be in fluid communication with the longitudinal channel. The guide slots 124 can be parallel with the ramps.

Figure 71:
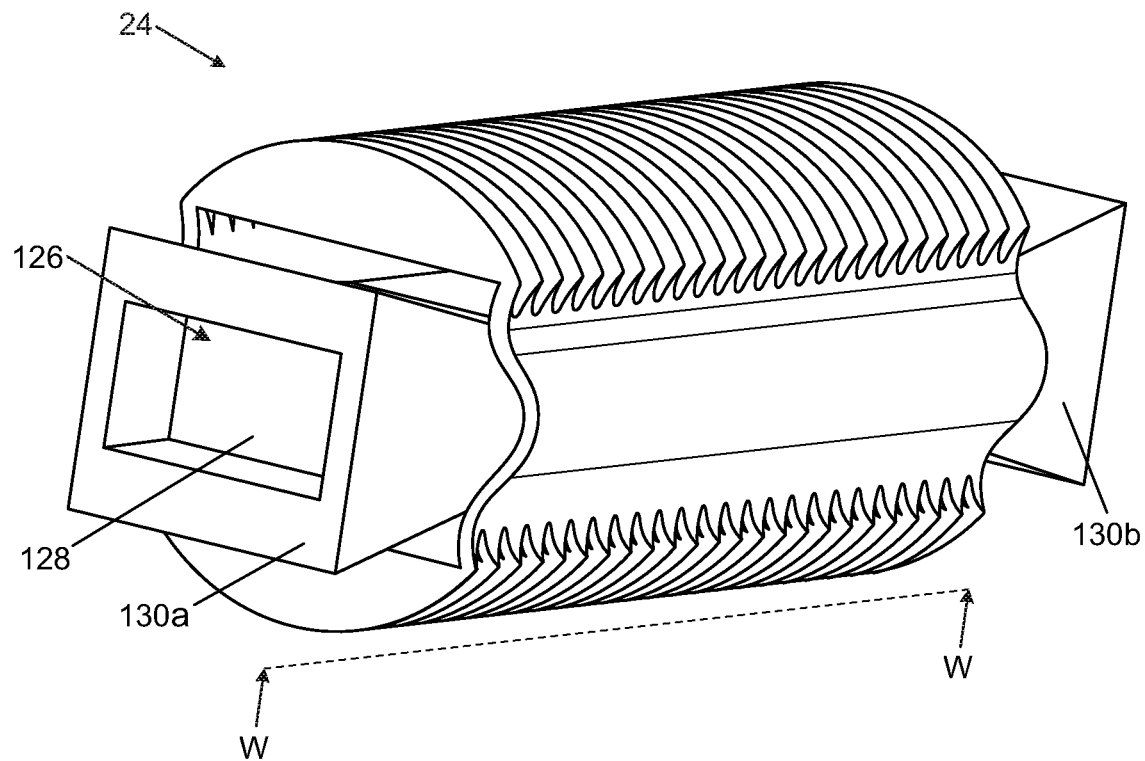
FIG. 71 illustrates a variation of the expandable section with the deployment rod.
Figure 72:
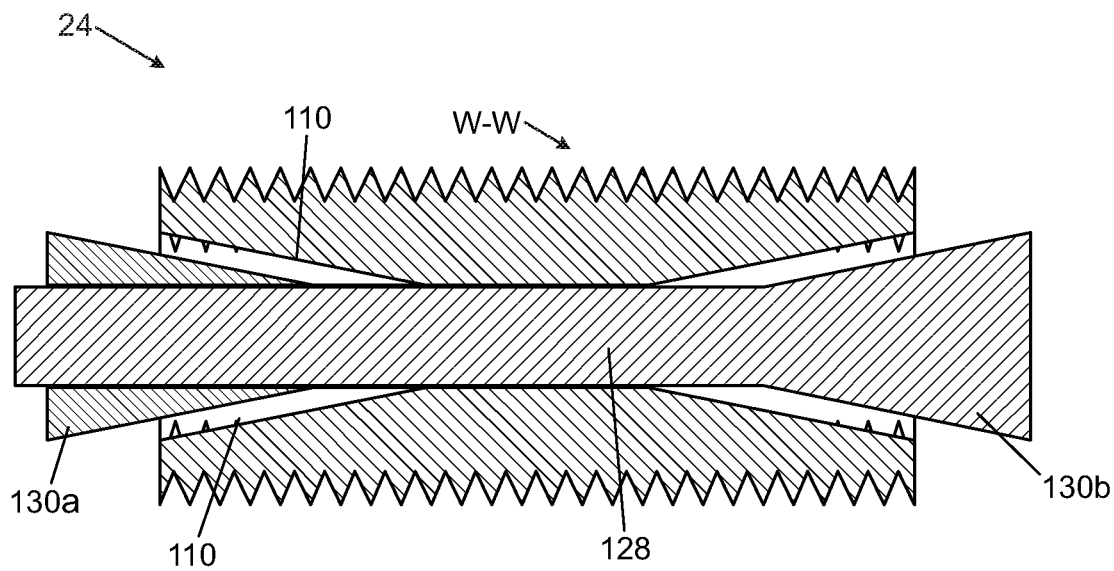
FIGS. 72 and 73 illustrate variations of cross-section W-W of FIG. 71.

FIGS. 71 and 72 illustrate that a first wedge and a second wedge can be inserted into the longitudinal channel of the expandable section. The second wedge and/or first wedge can be integral with the deployment rod. The first wedge can have a longitudinal wedge channel. The deployment rod can slidably attach to the first wedge through the wedge channel. The first wedge and second wedge can have configurations that substantially match the respective ramps.

Figure 73:
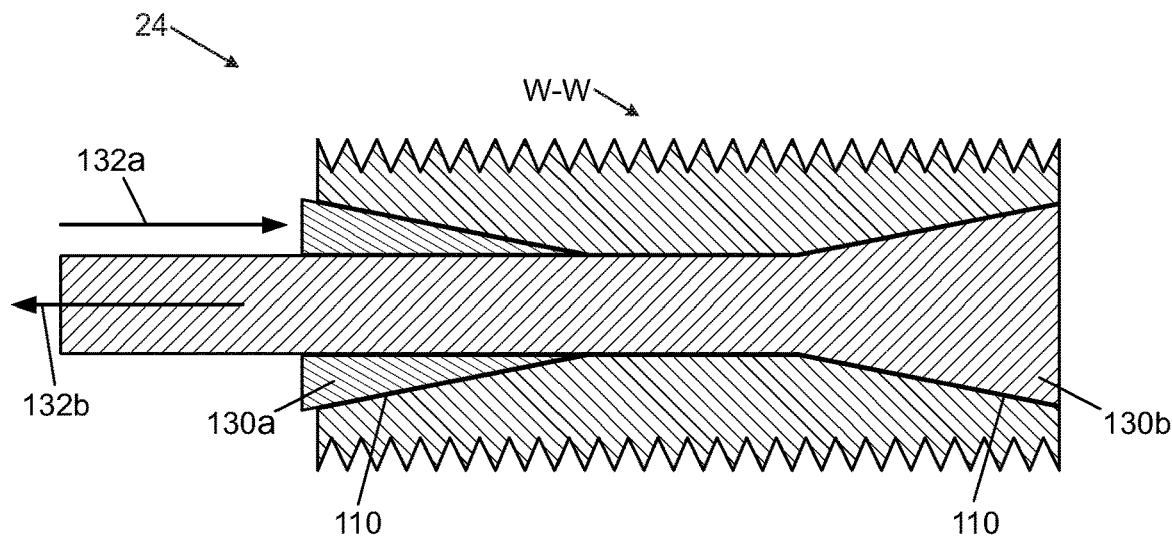

FIG. 73 illustrates that the opposing compressive first and second translational forces can be applied to the first wedge and the deployment rod, respectively. The first and second wedges can be deformably translated into the expandable section.

Figure 74:
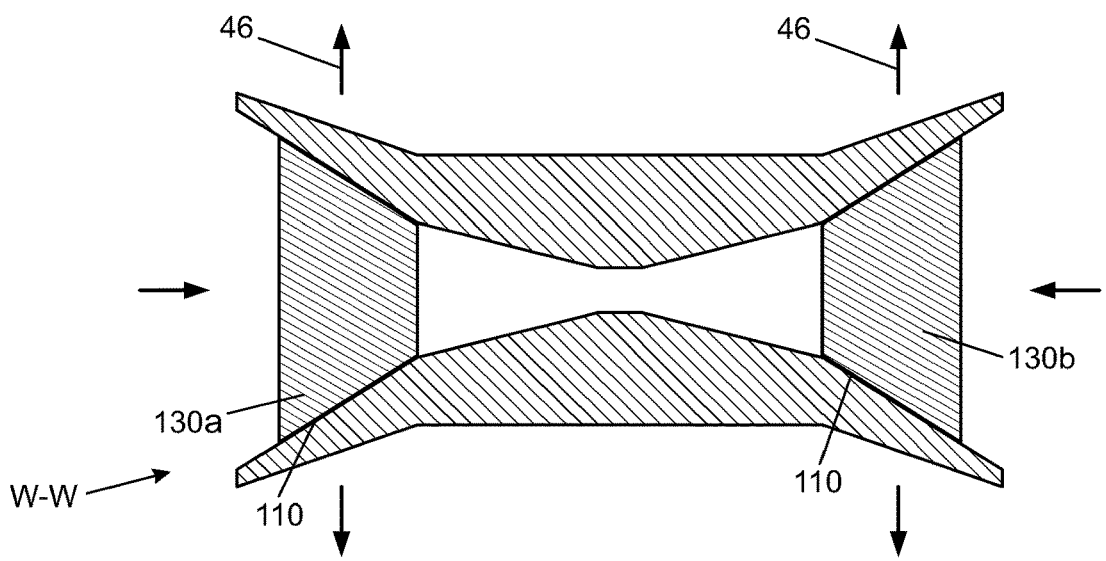
FIGS. 74 and 75 illustrate variations of cross-section W-W of FIG. 72.

FIG. 74 illustrates that the expandable section can radially expand, for example near the ends of the expandable section and/or to the length the wedges are inserted.

Figure 75:
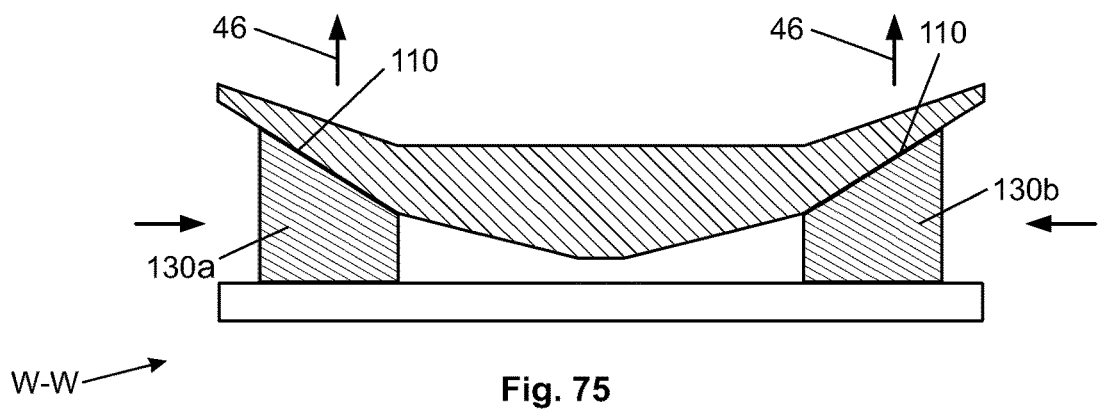

FIG. 75 illustrates that the expandable section and wedges can be configured to radially expand on only one side. For example, the wedges can have angled slopes on one side of the wedge and flat sides on the opposing side of the angled slopes. The expandable section can have a wall with tapered thickness on the side to be radially expanded, and a constant thickness wall, and/or a thicker wall than the tapered wall, on the side opposite the tapered wall.

Figure 76:
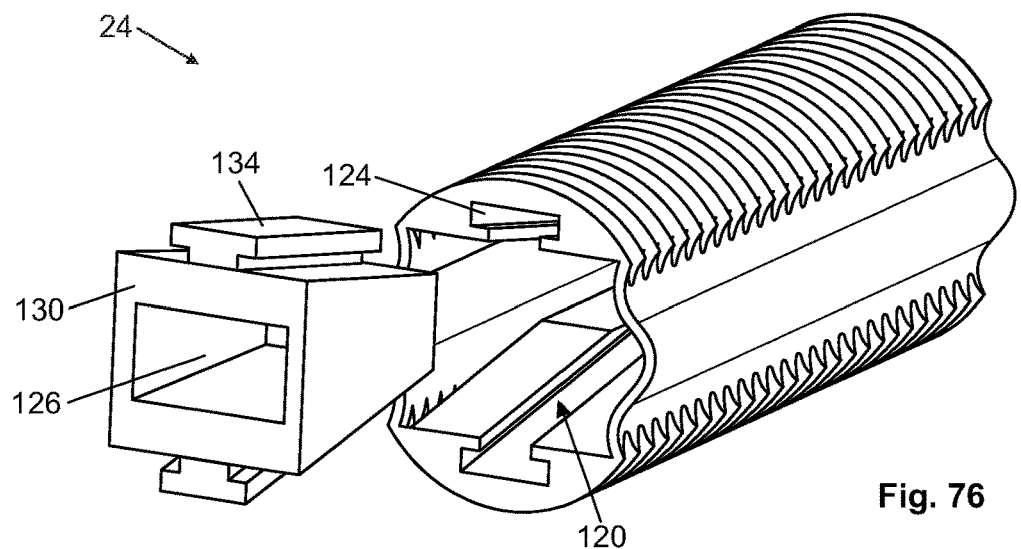
FIGS. 76 and 77 illustrate a variation of the expandable section of FIG. 70 with a wedge, and a method for using the same.
Figure 77:
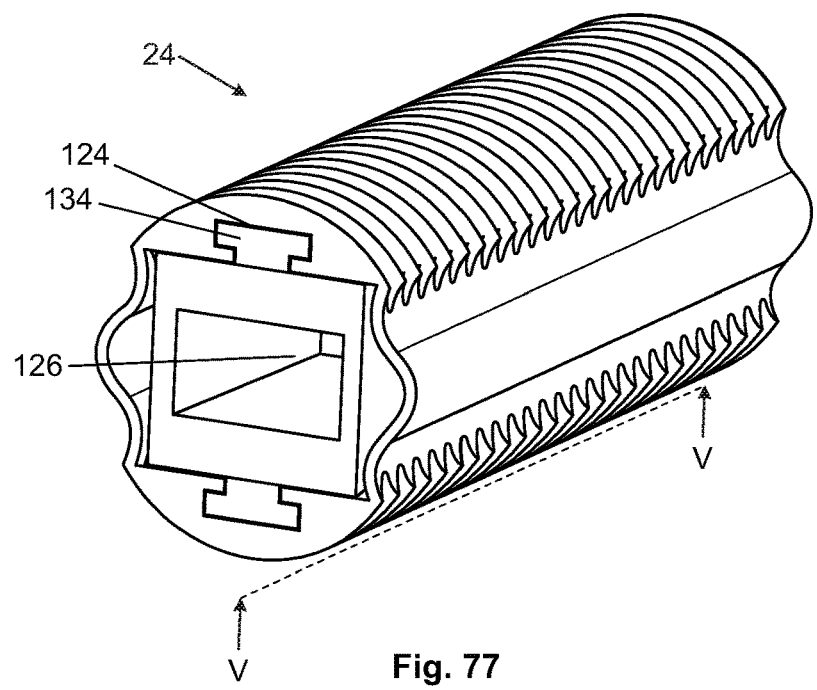
Figure 78:
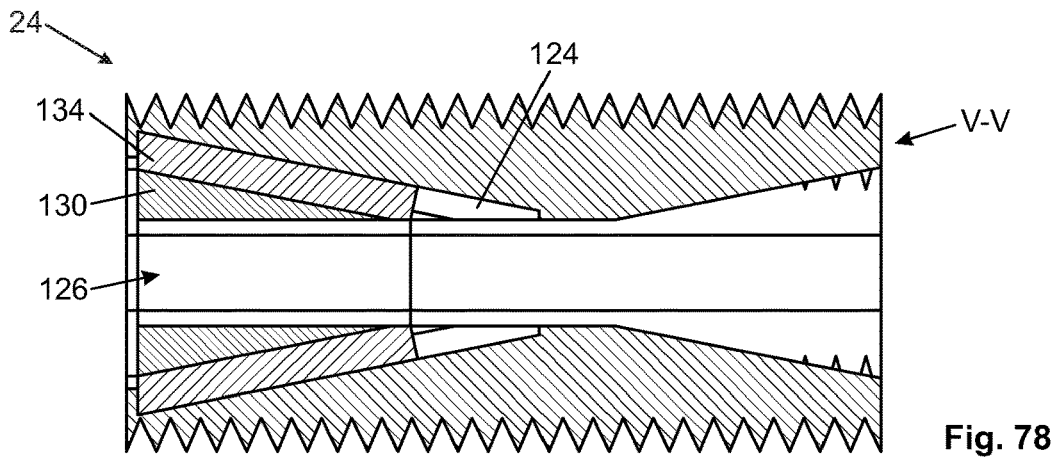
FIG. 78 illustrates a variation of cross-section V-V of FIG. 77.
Figure 79A:
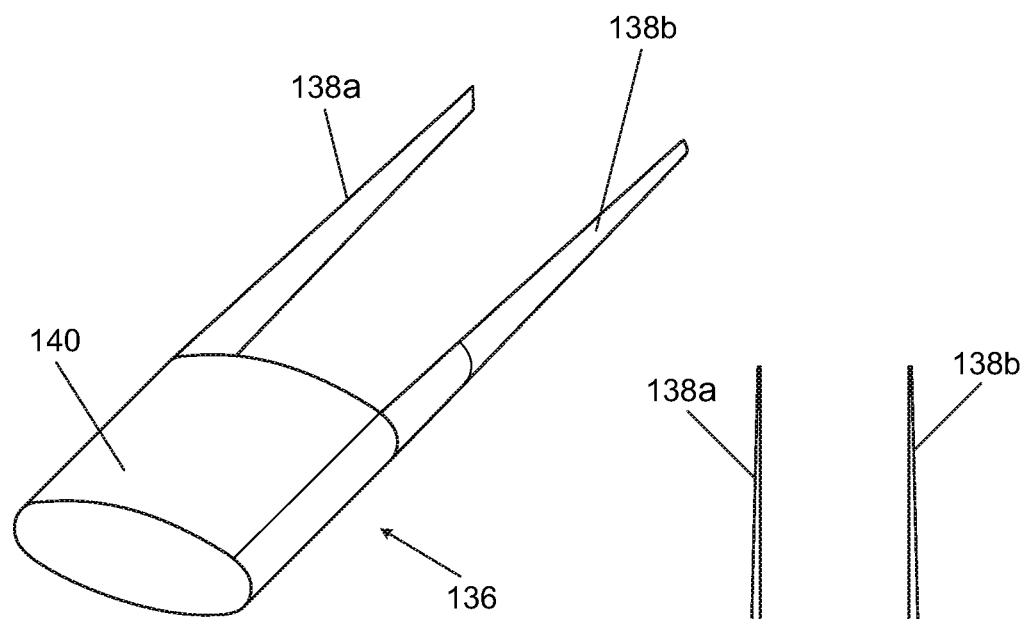
FIGS. 79a, 79b, 79c, and 79d illustrate perspective, top, side, and rear views of a variation of the manipulation tool.
Figure 79B:
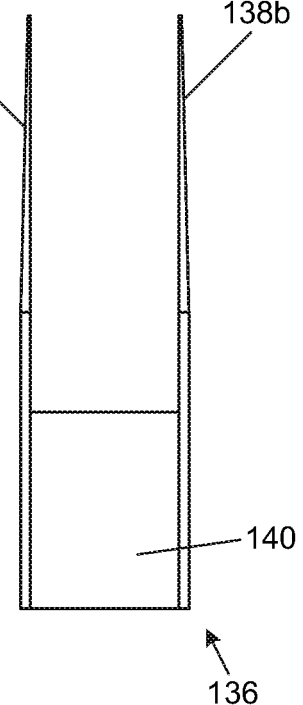
Figure 79C:
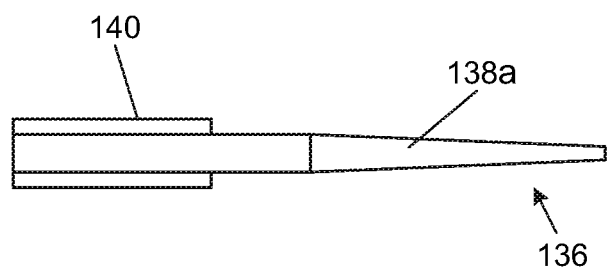
Figure 79D:
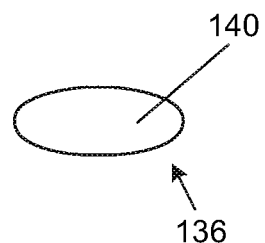

FIG. 76 illustrates that the wedge can have a wedge rail. The wedge rail can align with and insert into the guide slot 124. FIGS. 77 and 78 illustrate that the wedge rail can slidably attach to the guide slot 124.

FIGS. 79a through 79d illustrate that a manipulation tool can have a base, a first leg extending from the base, and a second leg extending from the base. The legs can be configured to fit into the manipulation channels of the expandable section. The legs can be used to insert into the manipulation channels and manipulate (e.g., translation, rotation, deformation) the expandable section. Legs can articulate with respect to the base. The leg articulation can be controlled by controls (not shown) on the base, such as a handle or trigger.

Figure 80:
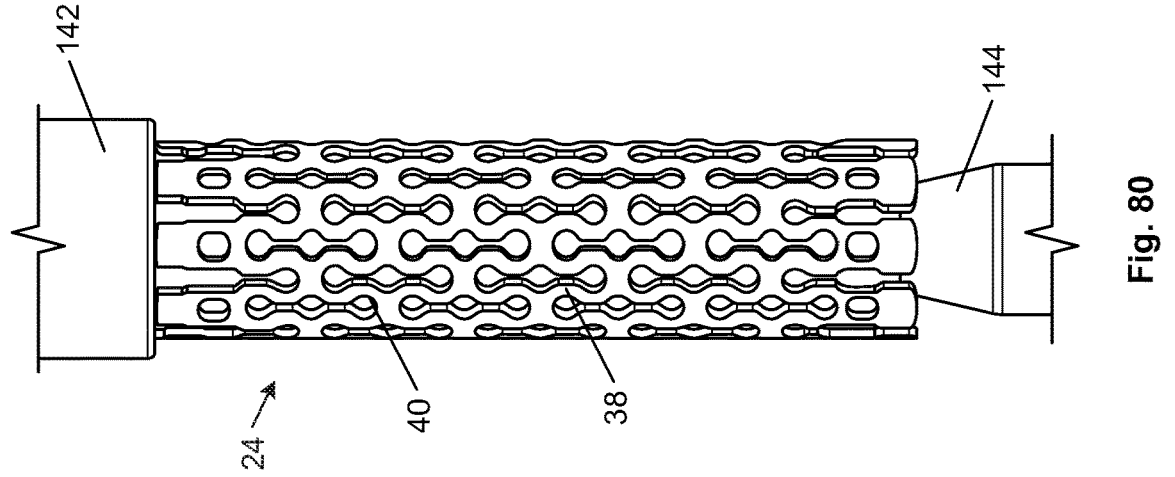

FIG. 80 illustrates that a cone or mandrel can be translated into the longitudinal channel of an expandable section having struts and joints. The expandable section can have no hoops. The expandable section can have an anvil at the opposite end of the cone.

Figure 81:
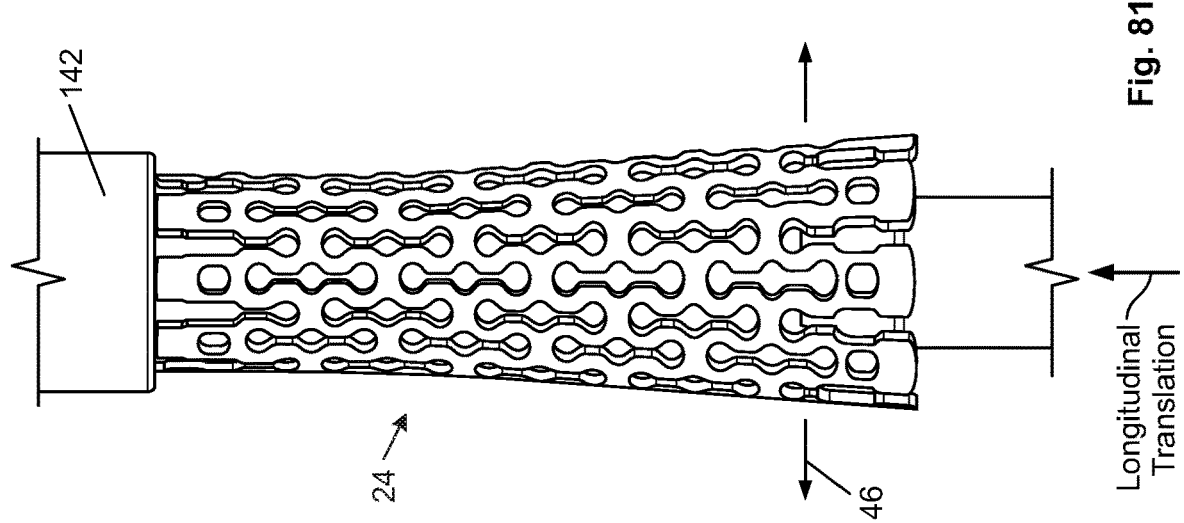

FIG. 81 illustrates that the cone can be forced toward the anvil, and/or the anvil can be forced toward the cone, resulting in longitudinal translation of the cone towards the anvil, through the longitudinal channel. The expandable section over the cone, for example at the distal end, can radially expand, as shown by arrows.

Figure 82:
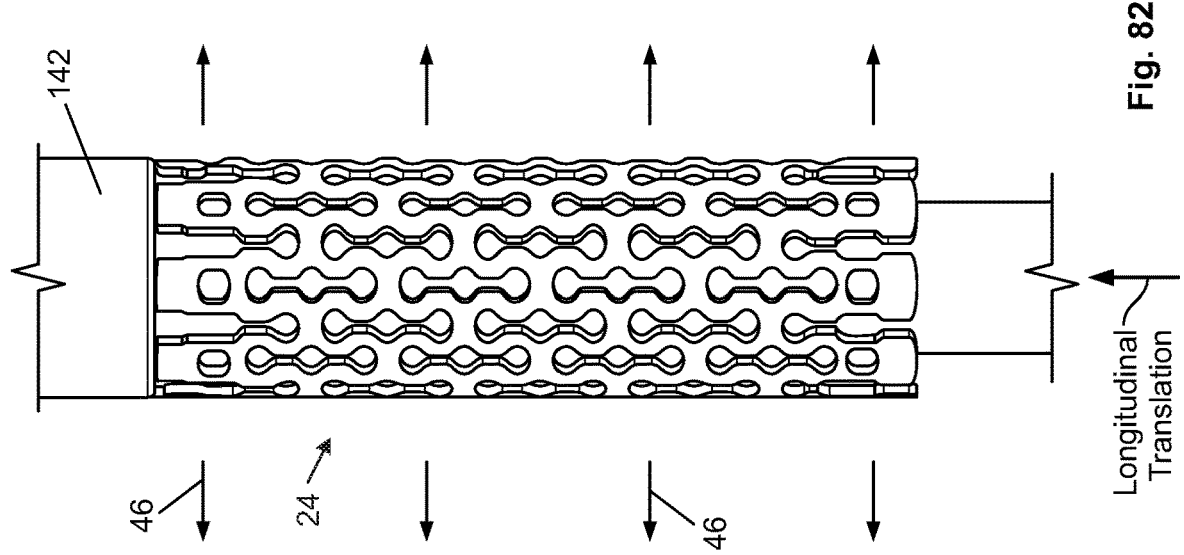
FIGS. 80 through 82 illustrate a variation of the expandable section and a method for radially expanding the same.

FIG. 82 illustrates that the cone can be longitudinally translated along the entire length of the expandable section. The cone can be received in the anvil. The entire length of the expandable section can radially expand, as shown by arrows. The expansion can be resilient and/or deformable. The cone can be removed or left in place.

FIG. 83 illustrates that the expandable section can have plates that can be integral with or attached to the joints and/or struts. The plates can be configured to be flexibly attached to or integral with the remainder of the expandable section. Each plate can be configured to substantially cover each port.

FIG. 84 illustrates that a first plate and a second plate can cover a port. The first plate can extend from a first joint adjacent to the port. The second plate can extend from a joint opposite to the first plate.

Figure 85:
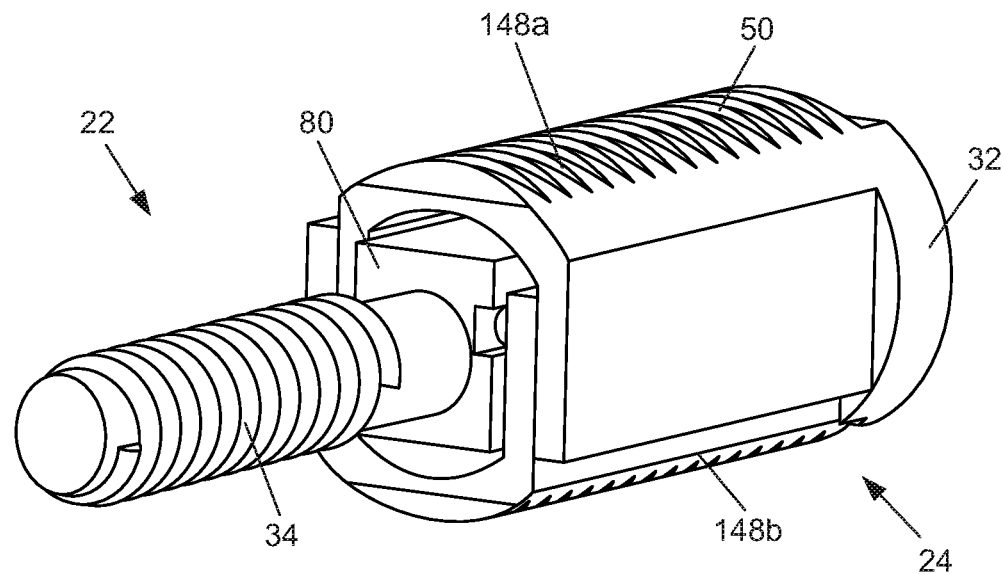
FIGS. 85 and 86 illustrate various perspective views of a variation of the expandable attachment device in a radially contracted configuration.
Figure 86:
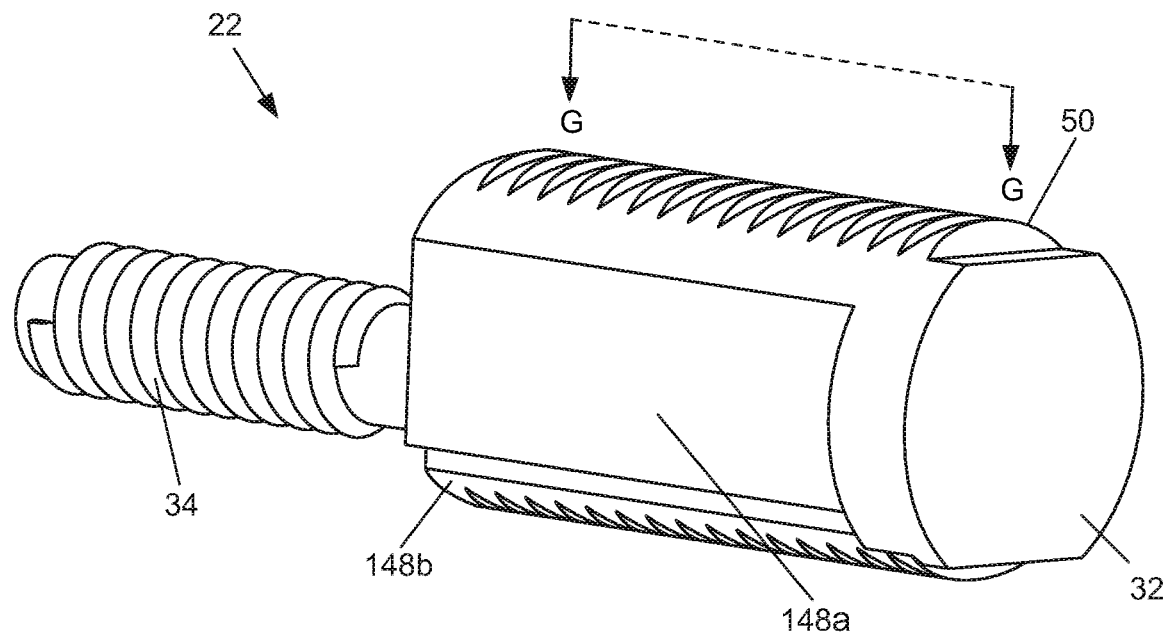
Figure 87:
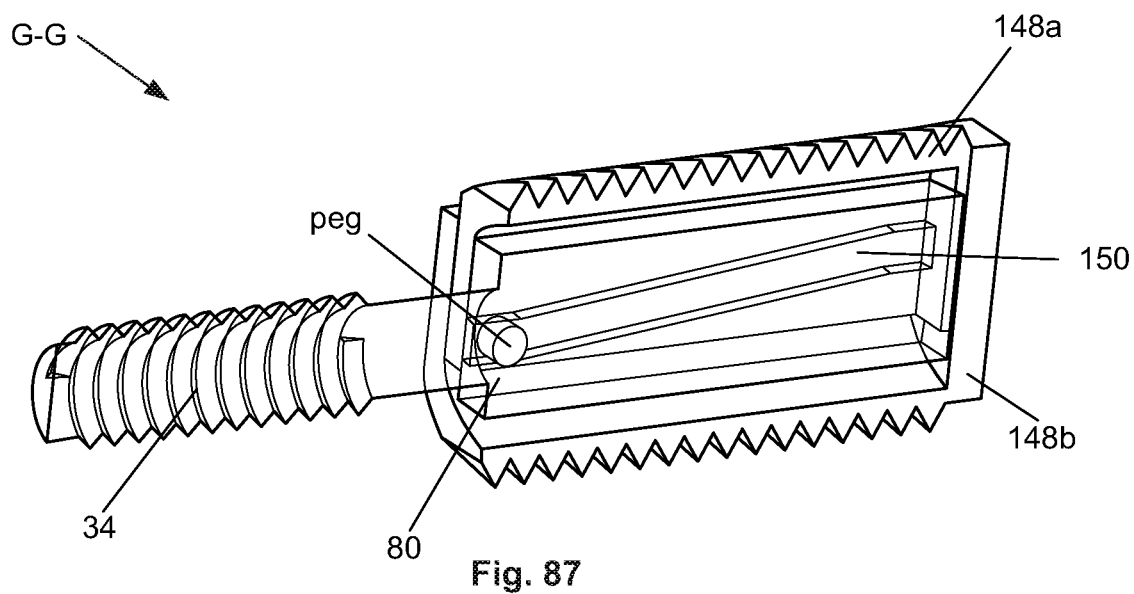
FIG. 87 illustrates a variation of cross-section G-G of FIG. 86.

FIGS. 85 through 87 illustrate an expandable attachment device that can have an expandable section that can have a first expandable element directly or indirectly slidably attached to a second expandable element. For example, the first expandable element can be slidably attached to the center shaft to translate up when the center shaft is translated distally, and the second expandable element can be slidably attached to the center shaft to translate down when the center shaft is translated distally. When the expandable attachment device is in a radially contracted configuration, the center shaft can be substantially inside the expandable element. When the expandable attachment device is in a radially expanded configuration, the center shaft can be substantially outside the expandable element.

The first expandable element can have the tip. The tip can be pointed and/or flat. The first expandable element can have thread on a top side. The first expandable element can have a peg (shown in FIG. 87) that can extend radially inward. The peg can be configured to slide in a first track on the side of the central shaft. The first track can extend from being low distally to high proximally.

The second expandable element can have thread on a bottom side. The first expandable element can have a peg that can extend radially inward similar to that of the first expandable element. The peg can be configured to slide in a second track on the side of the central shaft opposite the side of the first track. The first track can extend from being high distally to low proximally.

Figure 88:
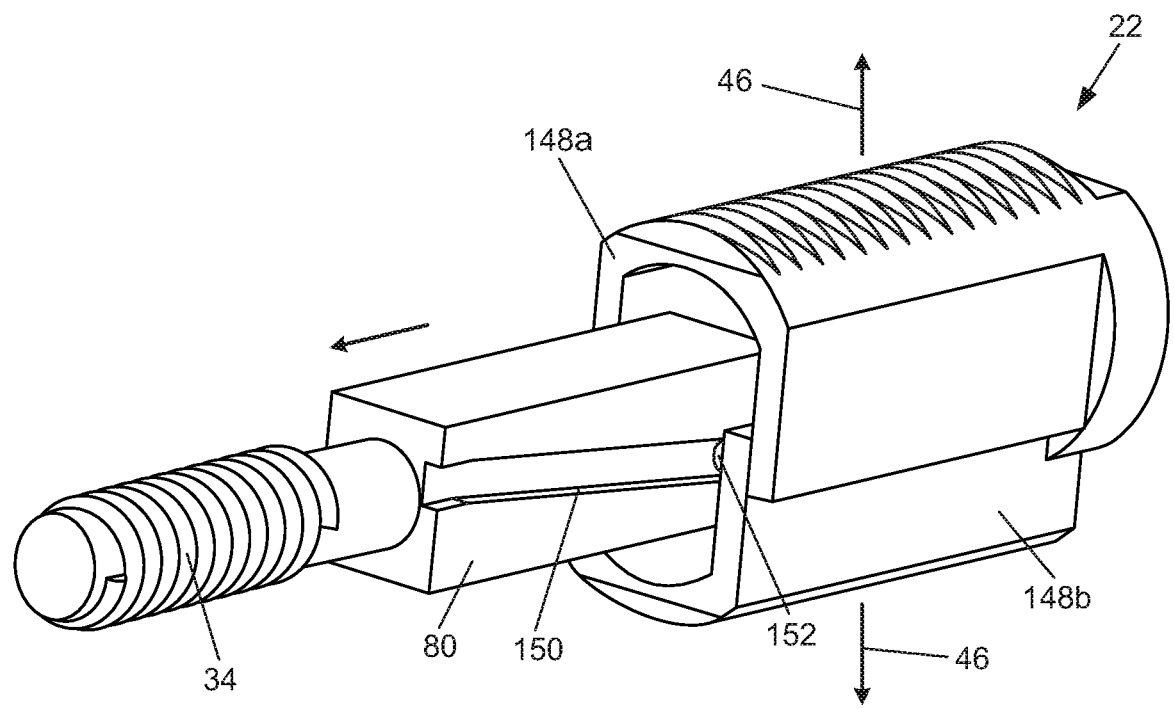
FIGS. 88 and 89 illustrate various perspective views of the variation of the expandable attachment device of FIGS. 85 through 87 in a radially expanded configuration.
Figure 89:
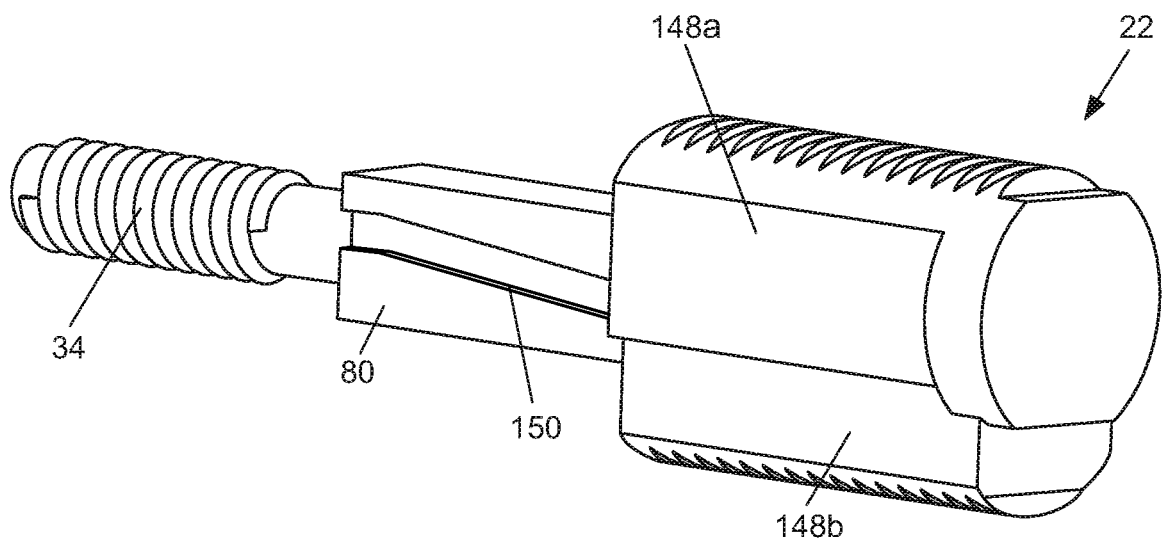
Figure 90:
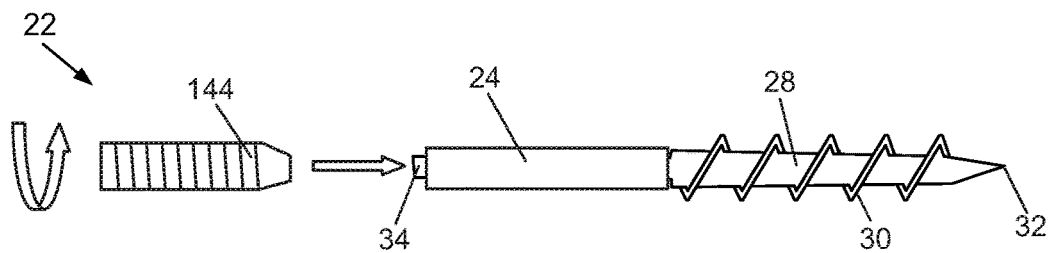
FIGS. 90 and 91 illustrate a variation of the expandable attachment device and a method for radially expanding the device.
Figure 91:
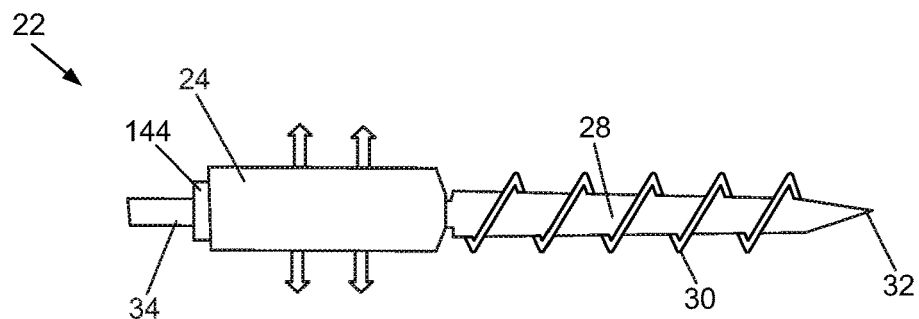
Figure 92:
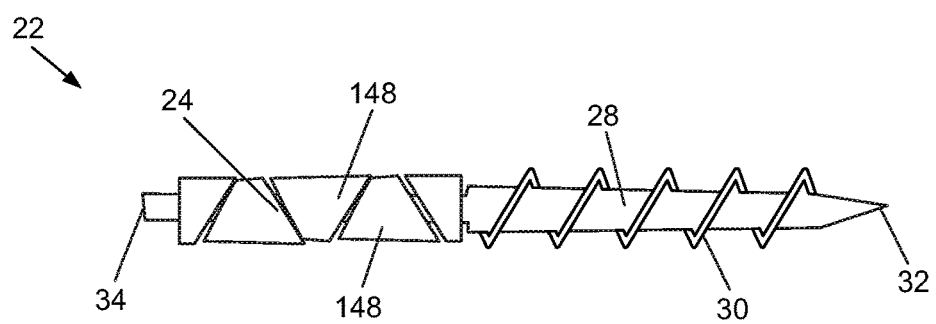
FIGS. 92 and 93 illustrate a variation of the expandable attachment device and a method for radially expanding the device.
Figure 93:
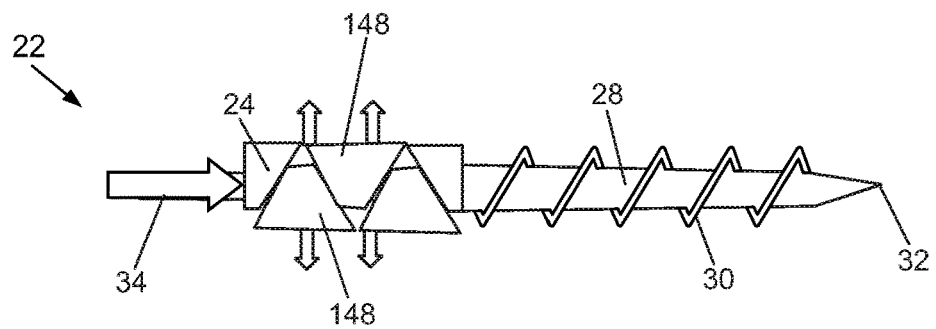

FIG. 88 illustrates that when the expandable attachment device is in a radially expanded configuration, the first expandable element can be separated from the second element.

As the central shaft is withdrawn from the expandable section, the peg of the first expandable element can be forced upward, forcing the first expandable element upward. As the central shaft is withdrawn from the expandable section, the peg of the first expandable element can be forced upward, as shown by arrow in FIG. 88, forcing the second expandable element downward.

As the central shaft is withdrawn from the expandable section, the peg of the second expandable element can be forced downward, forcing the second expandable element upward, as shown by arrow in FIG. 88.

Figure 94:
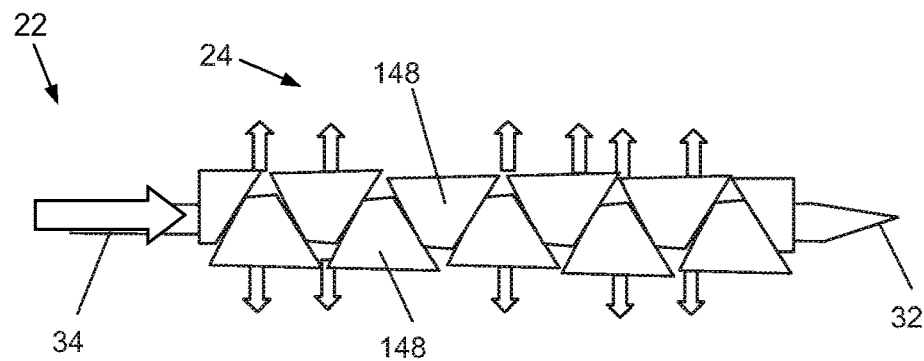
FIG. 94 illustrates a variation of the expandable attachment device and a method for radially expanding the device.

FIG. 94 illustrates that the expandable element devices can be substantially triangular from a lateral perspective. The expandable elements can be slidably attached to each other. The expandable attachment device can have multiple expandable elements. A compressive force, for example including a proximally directed force applied to the distal end (as shown by arrow) and/or the distal expandable element, can force the expandable elements to radially expand, as shown by arrows.

Figure 95:
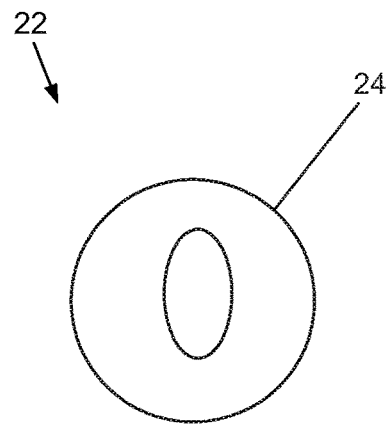
FIGS. 95 and 96 illustrate proximal end views of variations of the expandable attachment device.
Figure 96:
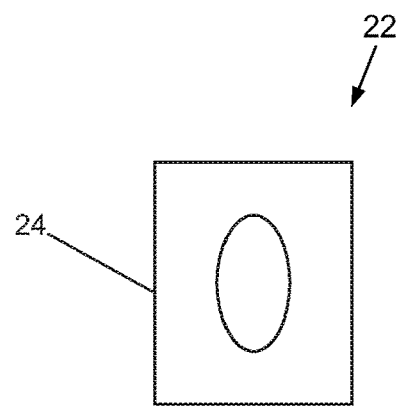

FIG. 95 illustrates that the distal end of the expandable attachment device, for example the tip, can have a transverse cross-section that can be round, circular, oval, square, rectangular, triangular, or combinations thereof. The expandable section can have a transverse cross-section that can be round, circular, oval, square, rectangular, triangular, or combinations thereof. FIG. 96 illustrates a variation of the expandable section.

Figure 97:
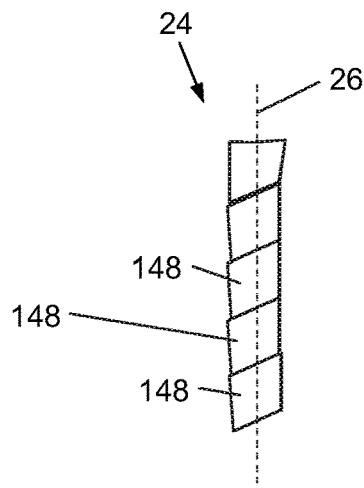
FIGS. 97 and 98 illustrate a variation of a the expandable section in radially contracted and expanded configurations, respectively.
Figure 98:
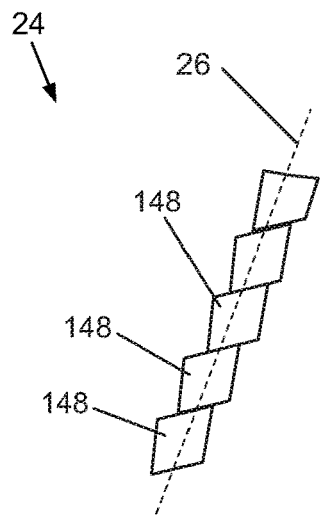

FIG. 97 illustrates that the expandable section in the radially contracted configuration can have a straight expandable section axes. FIG. 98 illustrates that the expandable section in a radially expanded configuration can have a straight or curved expandable section axis, and/or that the expandable section axis can be at an angle with respect to the expandable section axis in the radially contracted configuration.

FIGS. 99 and 100 illustrates that the expandable section can have a series of expandable elements having a slidably attached center shaft therethrough. The center shaft can have a center shaft anchor. The center shaft anchor can have a larger diameter than the diameter of the longitudinal channel. Teeth can radially extend from the expandable elements, for example from at least opposite sides of alternating expandable elements, as shown.

FIGS. 101 and 102 illustrate that the expandable elements can have guide rails. The guide rails can slidably attach to receiving elements on adjacent expandable elements. The longitudinal channel in at least every other expandable element can be elongated in the transverse direction.

Figure 103:
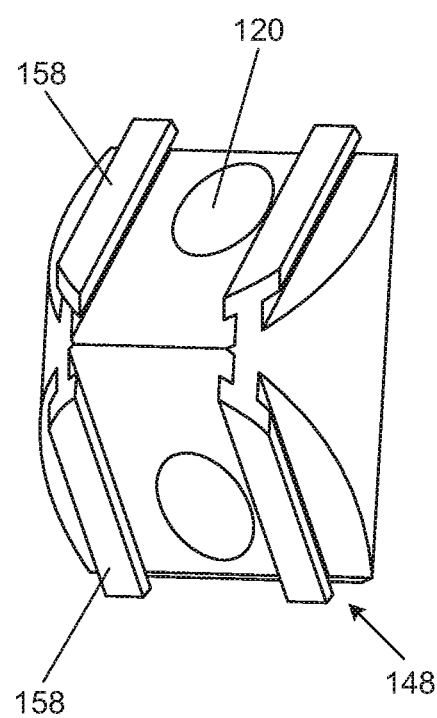
FIGS. 103 and 104 are front and side perspective views, respectively, of a variation of the expandable element.
Figure 104:
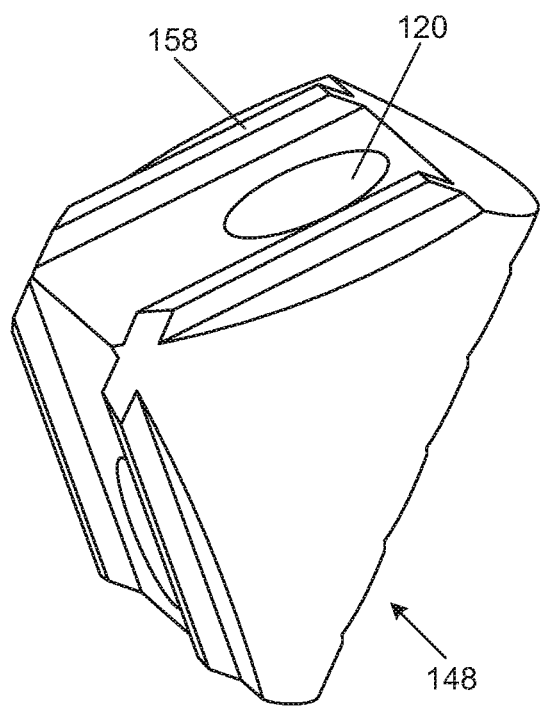

FIGS. 103 and 104 illustrate that the expanding element can have one or two guide rails on each surface adjacent to another expanding element when assembles. The cross-section of the longitudinal channel in an individual expanding element can be, for example, circular, oval, square, rectangular, or combinations thereof.

Figure 105:
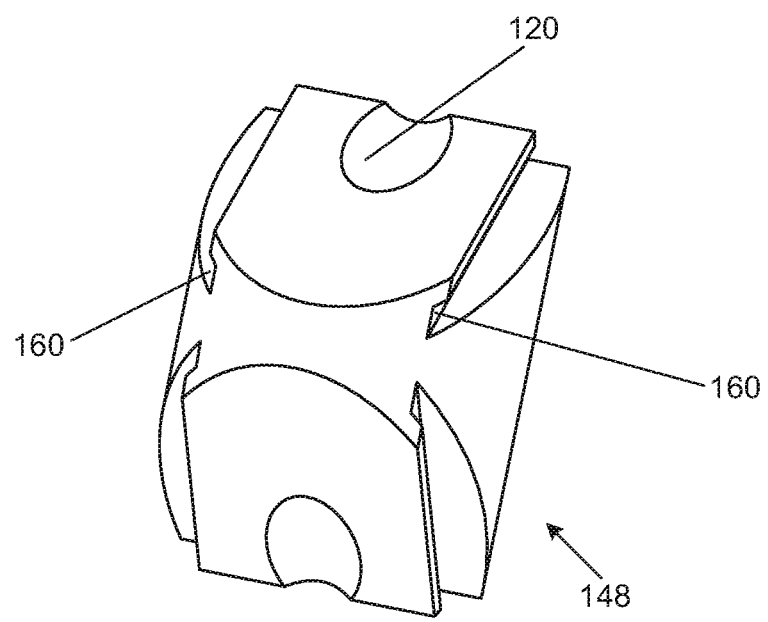
FIGS. 105 through 107 illustrate variations of the expandable element.

FIG. 105 illustrates that the expandable element can have one, two or more guide grooves on each surface adjacent to another expanding element when assembled. The guide grooves can be configured to slidably attach to the guide rails.

Figure 106:
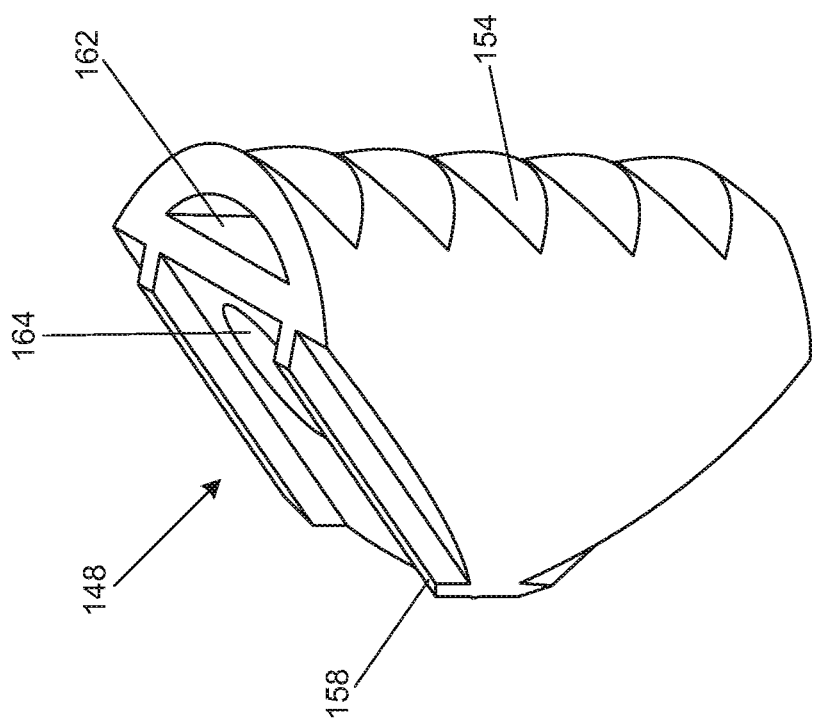

FIG. 106 illustrates that the expandable element can have one or more contouring channels. The contouring channels can be a defined, substantially closed volume within the expandable element. The contouring channels can deform, for example, due to force applied against the teeth during use. When deformed, the contouring channel can, for example, reduce the stress applied on the neighboring tissue when implanted compared to the expandable element in a non-deformed configuration.

Figure 107:
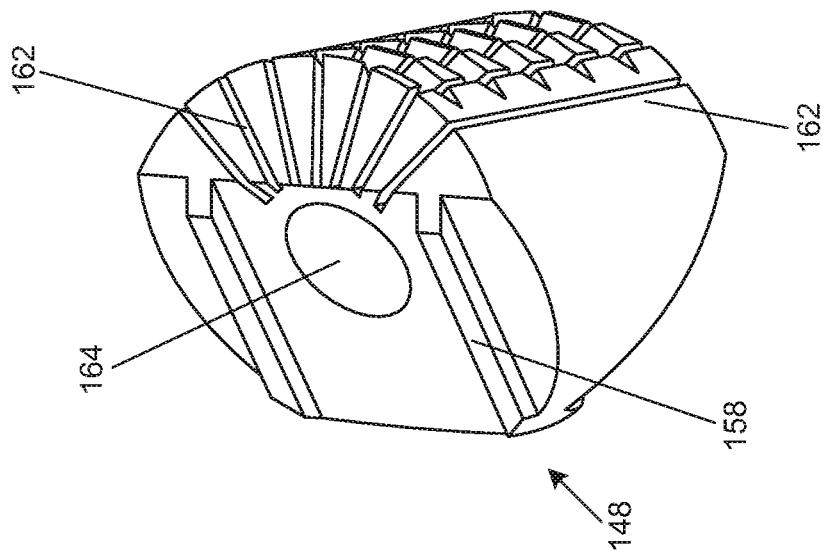

FIG. 107 illustrates an expandable element having a number of contouring channel extending radially away from the expandable element channel. The contouring channels can be configured as slots open to the outside of the expandable element.

Figure 108:
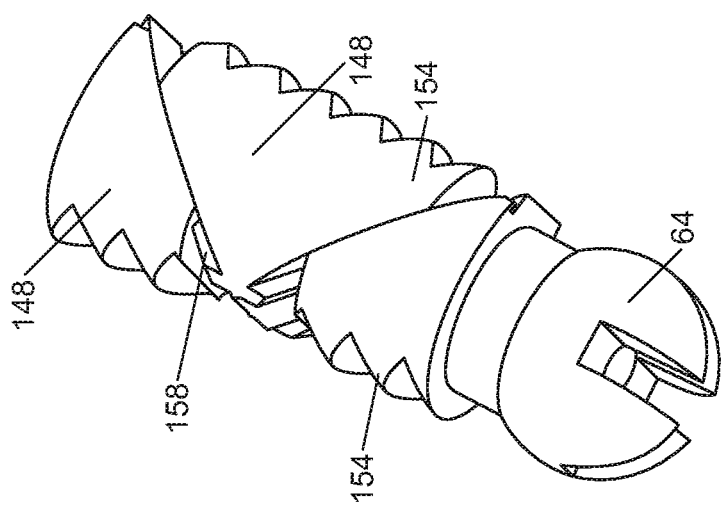

FIG. 108 illustrates that the distal end cap can be distal to the most distal expandable element. For example, the distal end cap can be, or be attached to, the center shaft anchor.

Figure 109:
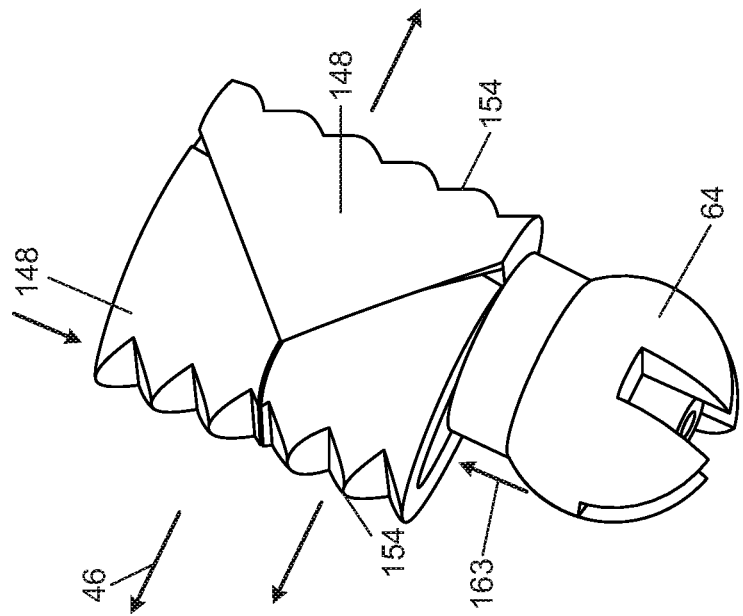
FIGS. 108 and 109 illustrate a variation of the expandable section and distal end and a method for radially expanding the device.

FIG. 109 illustrates that a longitudinally compressive force, as shown by arrow, can be delivered through the distal end cap. The expandable elements can then radially expand, as shown by arrows.

Figure 111:
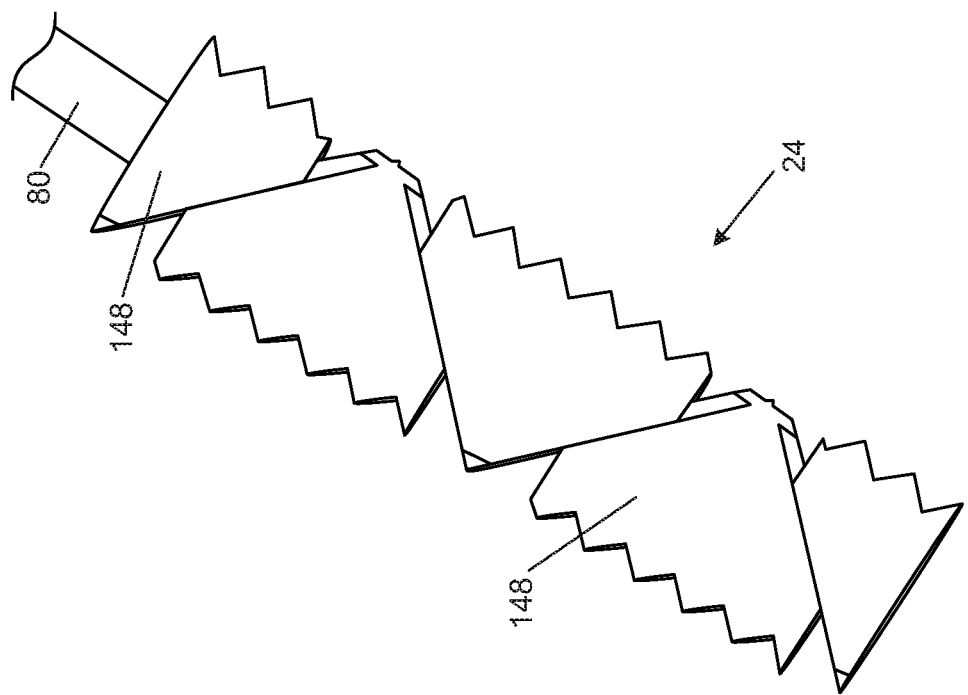
FIGS. 110 and 111 illustrate variations of the expandable section.
Figure 110:
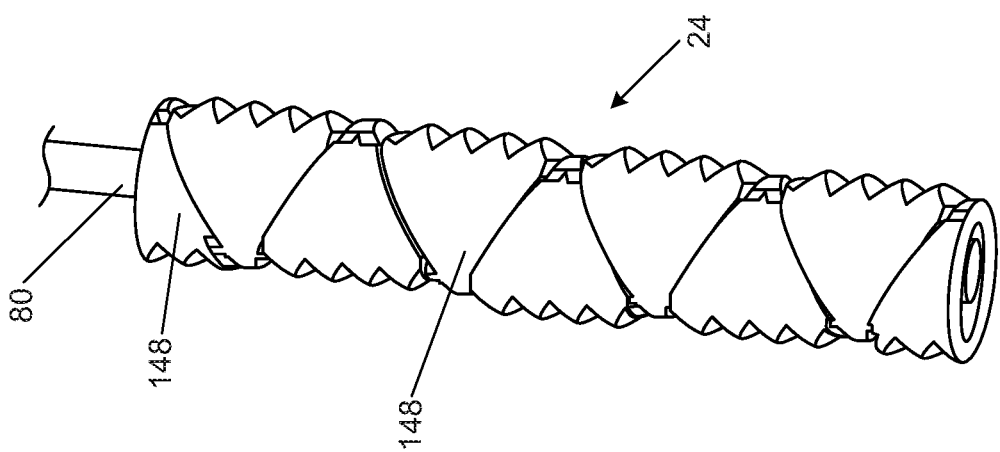

FIGS. 110 and 111 illustrate the expandable section having nine and five expandable elements, respectively.

Figure 112:
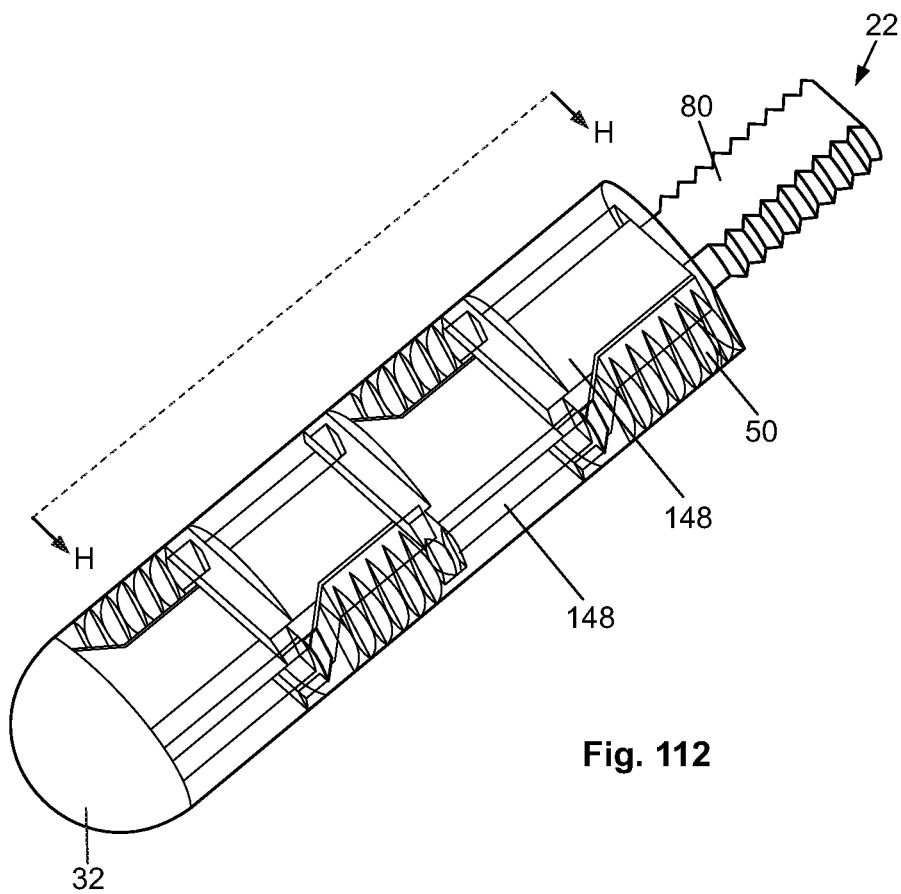
FIGS. 112 and 113 illustrate a variation of the expandable attachment device and a method for radially expanding the device.
Figure 113:
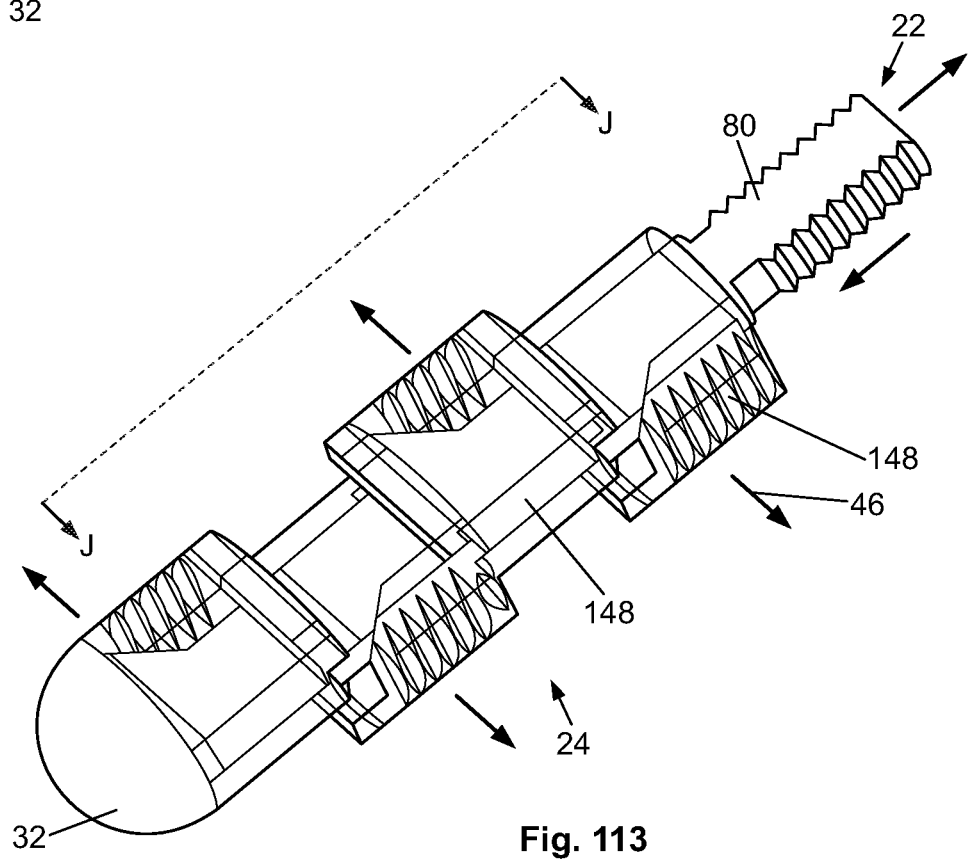

FIGS. 112 and 113 illustrates that the center shaft can be configured to have one or more alternately oppositely facing integral wedges. The expandable section can have one or more expandable elements. The expandable elements can have guide rails on the proximal ends and guide grooves on the distal ends. The guide grooves and guide rails can constrain relative motion between the expandable elements to a single degree of freedom (e.g., lateral motion). The internal surfaces of the expandable elements can have alternately oppositely facing internal ramps that can be configured to abut the integral wedges.

FIG. 113 illustrates that the center shaft can be translated relative to the expandable section, for example with the center shaft being translated out of the expandable section. The expandable elements can then radial expand in opposite directions as the adjacent expandable elements, as shown by arrows.

Figure 114:
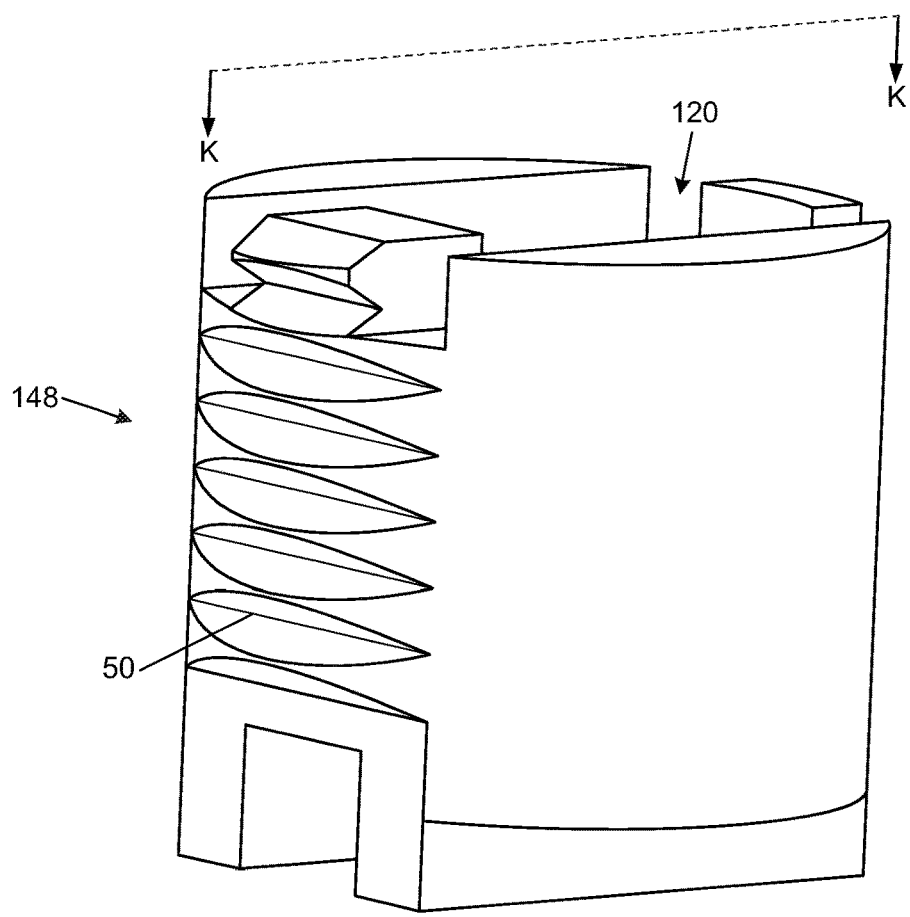
FIG. 114 illustrates a variation of the expandable element of FIGS. 112 and 113.

FIG. 114 illustrates that the expandable element can have one or two guide grooves in the distal end of the expandable element. The guide grooves can be notches in the wall around the longitudinal channel. The expandable element can have one or two guide rails at the proximal end of the expandable element. The guide rails can be configured to slidably attach to the guide grooves when one expandable element in stacked on another expandable element.

Figure 115:
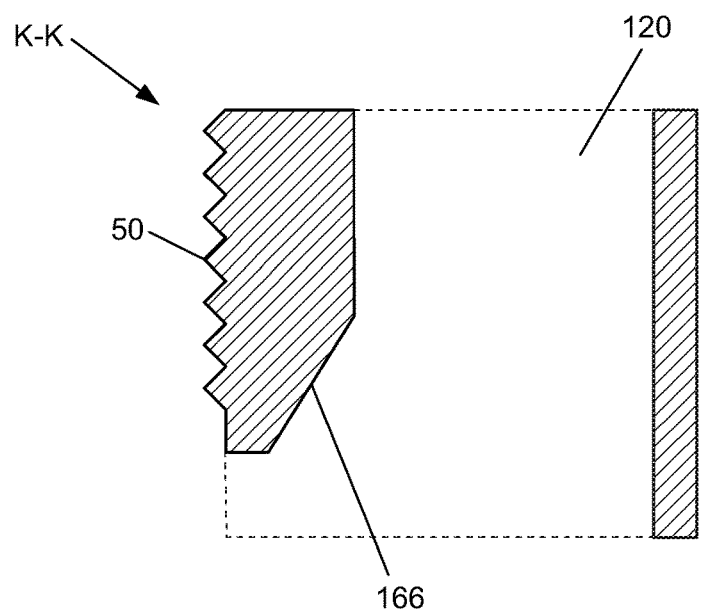
FIG. 115 illustrates a variation of cross-section K-K of FIG. 114.

FIG. 115 illustrates that the internal ramp can be a slope on the internal surface of the longitudinal channel. The thread can be on a single side of the expandable element.

Figure 117:
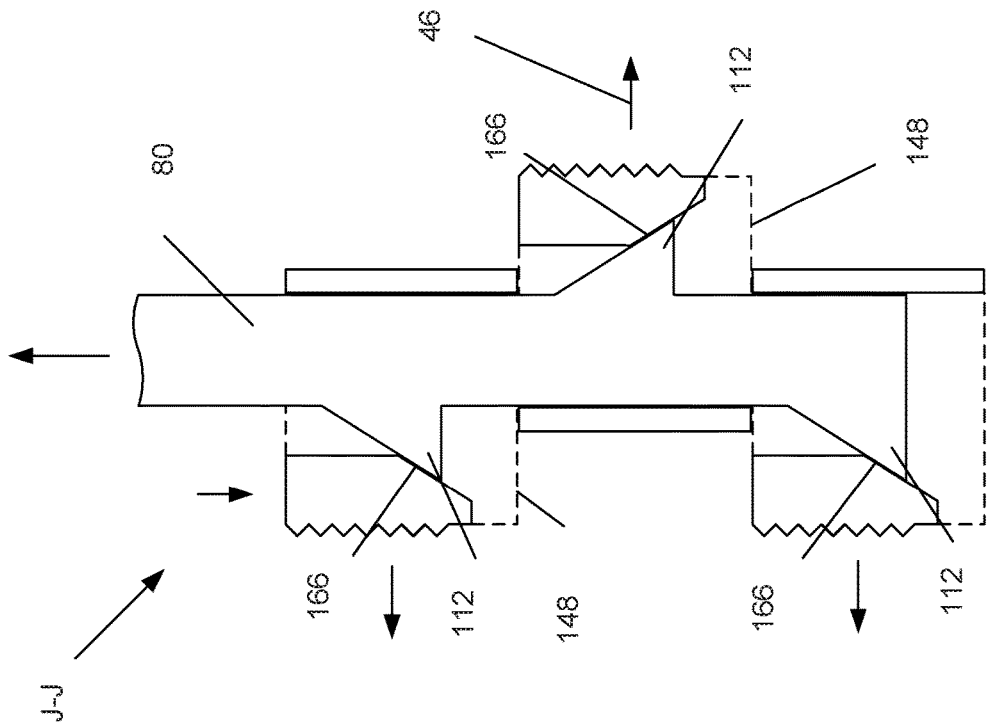
FIGS. 116 and 117 illustrate cross-sections H-H and J-J, respectively, of FIGS. 112 and 113, respectively.
Figure 116:
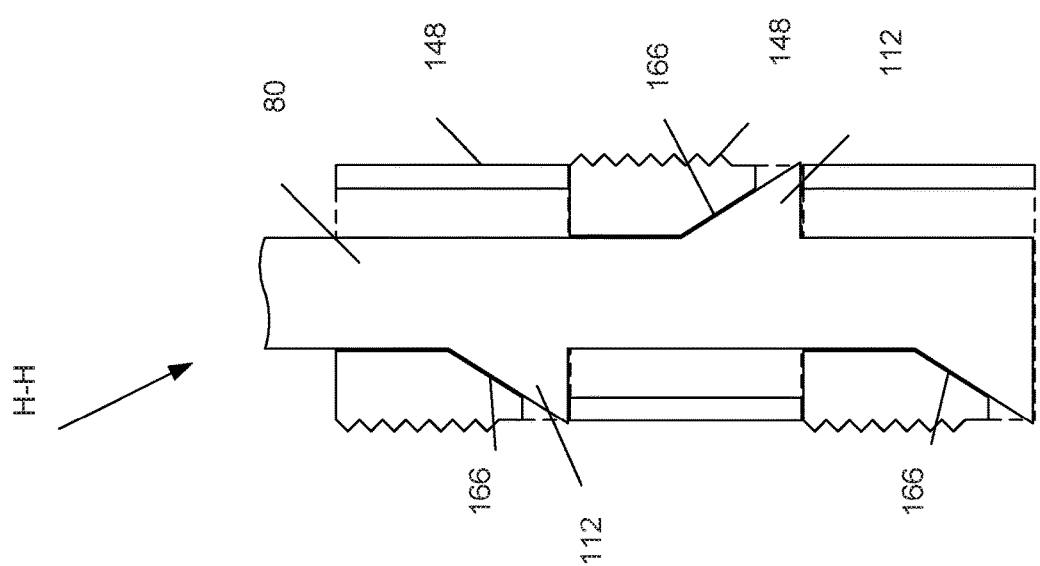

FIGS. 116 and 117 illustrate that when the integral wedges of the center shaft press into the internal ramps of the expandable elements, as shown by arrows in FIG. 117, the expandable elements can be pushed radially outward by the integral wedges, as shown by arrows.

Figure 118:
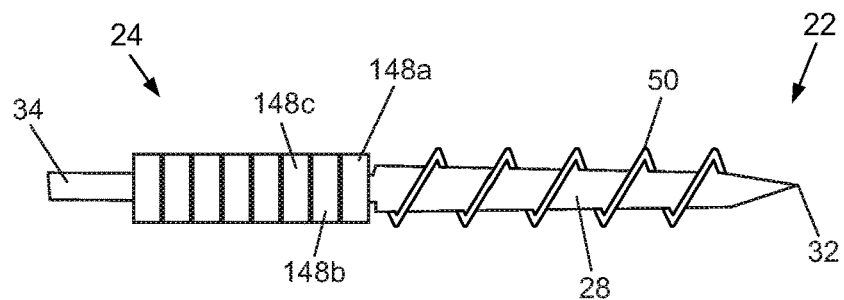
FIGS. 118 and 119 illustrate a variation of the expandable attachment device and a method for radially expanding the device.
Figure 119:
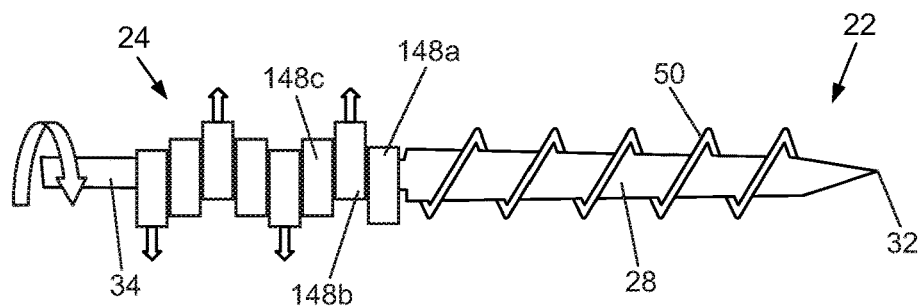
Figure 120A:
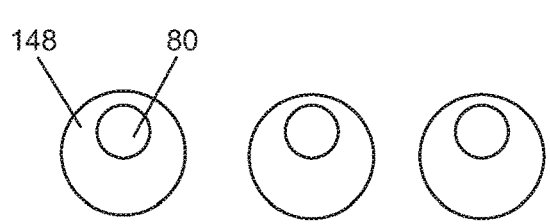
FIG. 120a illustrates a variation of multiple expandable elements.

FIG. 118 illustrates that the expandable section can have first, second, third and more expandable elements that can be cams or other offset-rotation elements. FIG. 119 illustrates that the distal end can be rotated, as shown by arrow. The expandable elements can then radially translate or expand, as shown by arrows. The expandable elements can translate at different timings, so that the FIG. 120a illustrates that the expandable elements can have a center shaft extending through the expandable elements. The center shaft can be offset from the center of area of the expandable element in the plane transverse to the expandable attachment device axis.

Figure 120B:
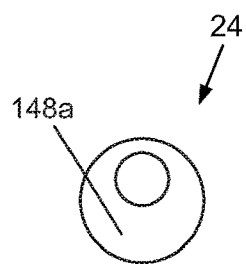
FIG. 120b is an end view of a variation of the expandable section in a contracted configuration.

FIG. 120b illustrates that the expandable section in a radially contracted configuration can have all of the expandable elements substantially aligned along the expandable attachment device axis.

Figure 120C:
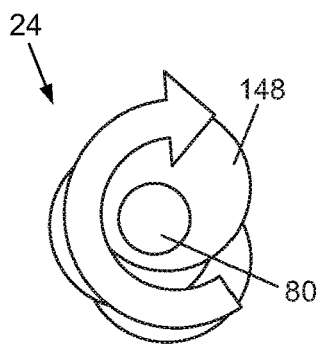
FIG. 120c is an end view of a variation of the expandable section in a radially expanded configuration and a method for radially expanding the expandable section.

FIG. 120c illustrates that the expandable section can be radially expanded by rotating the center shaft and/or rotating the expandable elements around the center shaft. The cam expandable elements can splay and radially expand.

Figure 121:
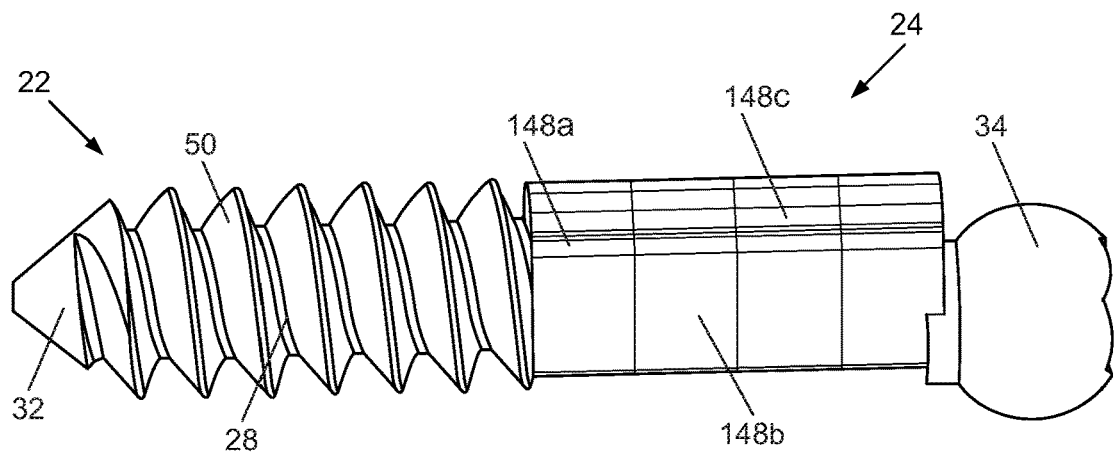
FIGS. 121, 122, 123 and 124 are side, perspective, distal end, and proximal end views, respectively, of a variation of the expandable attachment device in a radially contracted configuration.

FIG. 121 illustrates that the expandable attachment device can have multiple expandable elements eccentrically attached to a center shaft, and/or with lobed configurations.

Figure 122:
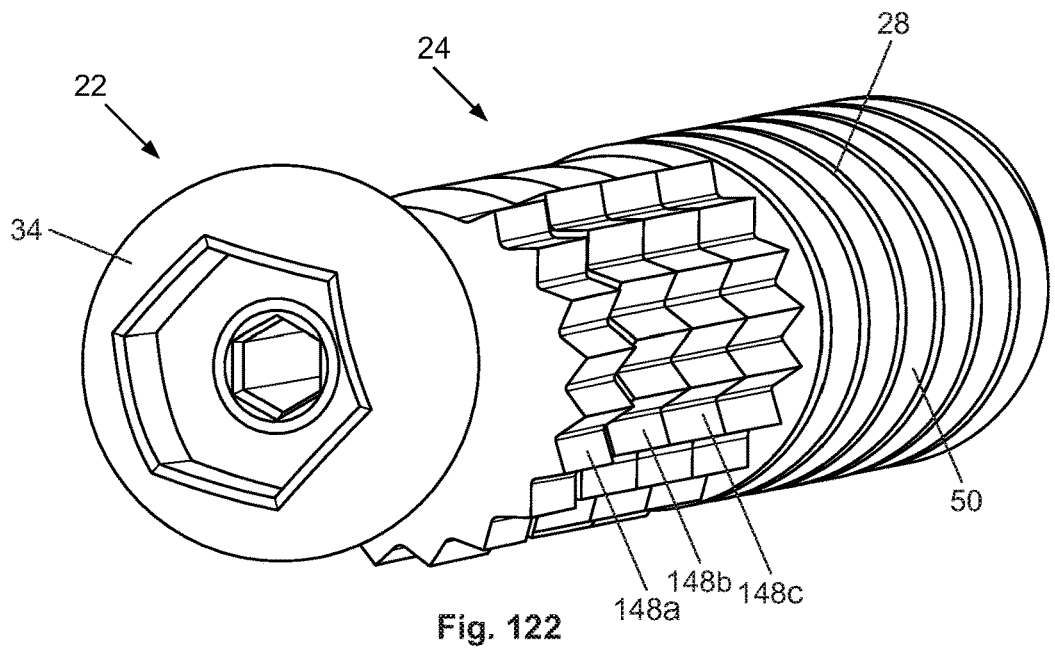
Figure 123:
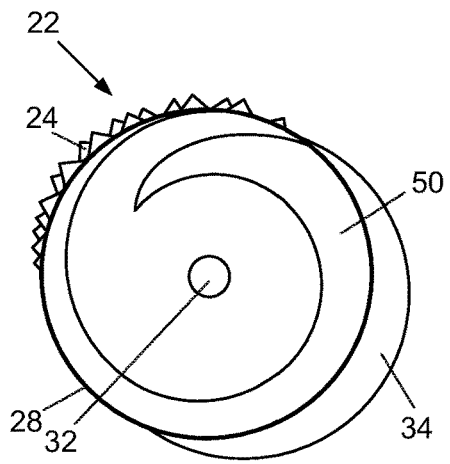
Figure 124:
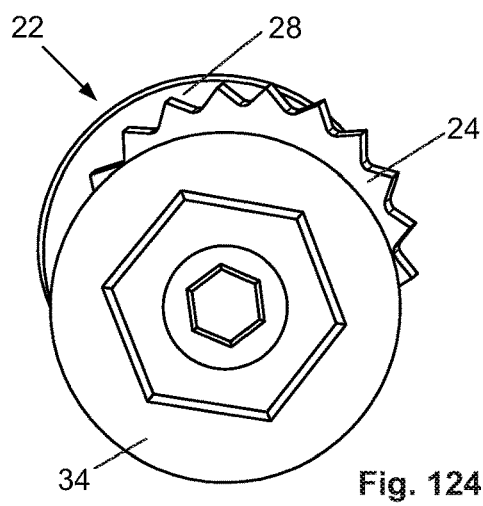

FIGS. 122 through 124 illustrate that the expandable attachment device can have one through four expandable elements eccentrically attached to a center shaft (not shown). The expandable elements can have teeth radially extending from the expandable elements.

Figure 125:
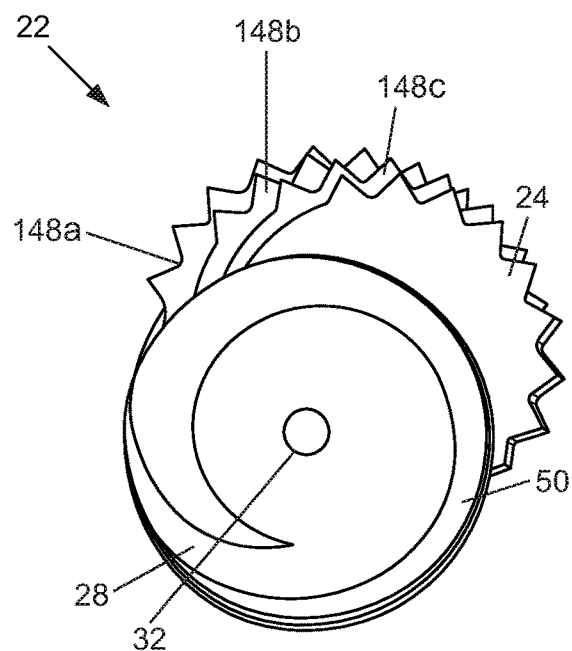
FIGS. 125, 126, and 127 are distal end, proximal end, and side views, respectively, of a variation of the expandable attachment device of FIGS. 121 through 124 in a radially expanded configuration.
Figure 126:
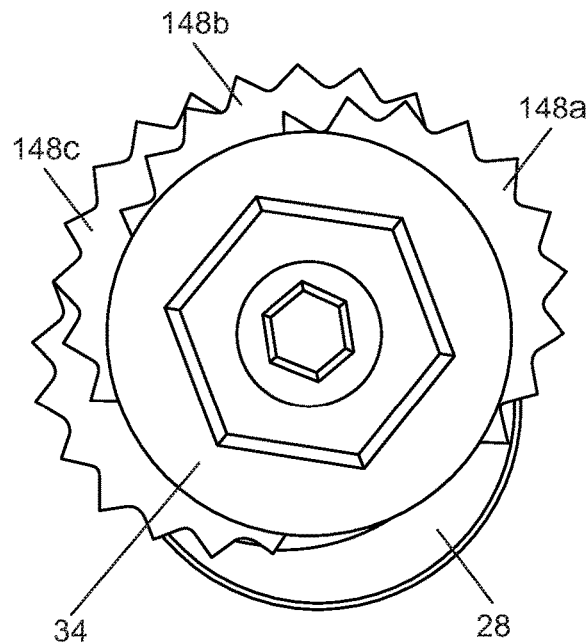
Figure 127:
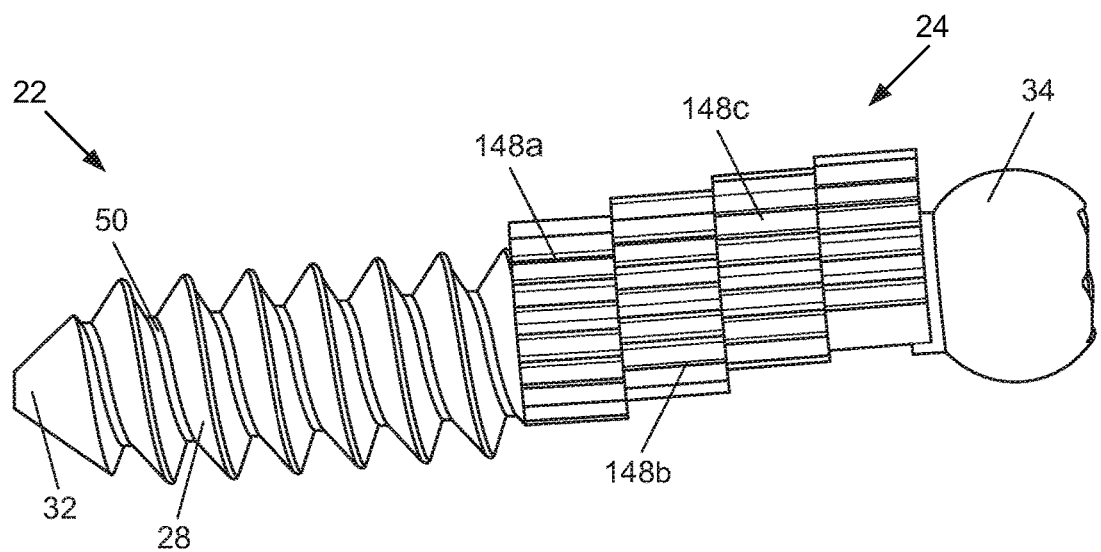

FIGS. 125 through 127 illustrate the expandable attachment device with eccentrically attached expandable elements in a radially expanded configuration.

Figure 128:
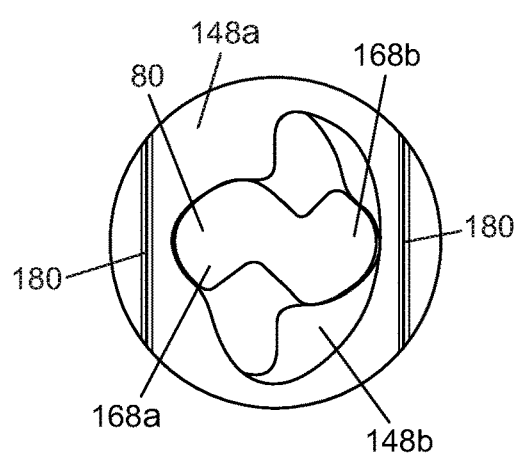
FIGS. 128 and 129 are front and perspective views, respectively, of a variation of the expandable section in a radially contracted configuration.
Figure 129:
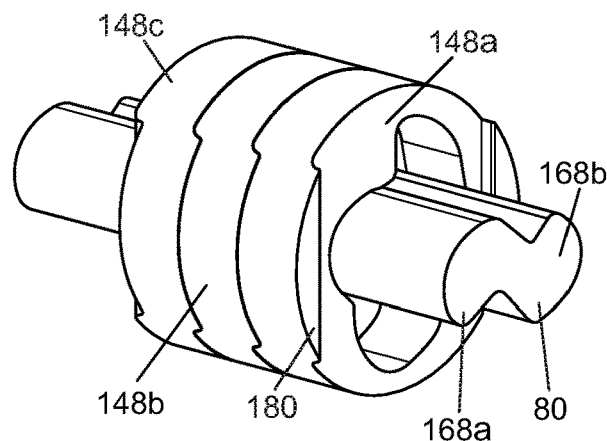

FIGS. 128 and 129 illustrate that the expandable section can have a first, second and third expandable element. The expandable elements can be slidably attached by interlocking rails and tracks. The rails and tracks can constrain relative motion between adjacent expandable elements to one degree of freedom (e.g., vertical relative motion).

The expandable elements can have longitudinal channels configured, for example as shown, to receive a multi-lobed center shaft and be controllable as shown in FIGS. 128 through 133. The configuration of the longitudinal channel in each expandable element can be the same or different as the other expandable elements. For example, the first expandable element and the third expandable element can have substantially identically configured longitudinal channels. The second expandable element can have a longitudinal channel configured to be a horizontally reversed configuration of the longitudinal channel of the first expandable element. The second expandable element can have a longitudinal channel configured to be-about a 180° rotation of the longitudinal channel of the first expandable element. The center shaft can have a first lobe and a second lobe.

Figure 130:
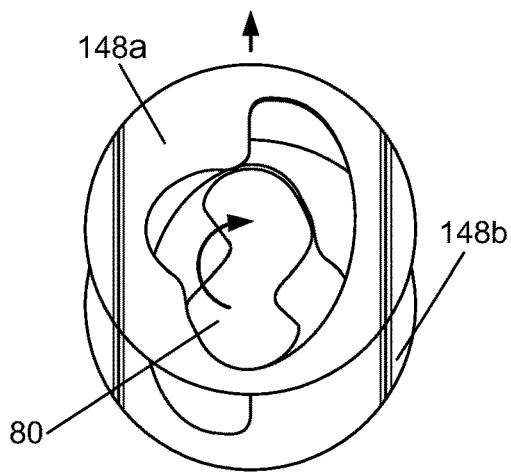
FIGS. 130 and 131 are front and perspective views, respectively, of the variation of the expandable section of FIGS. 128 and 129 in a radially expanded configuration.
Figure 131:
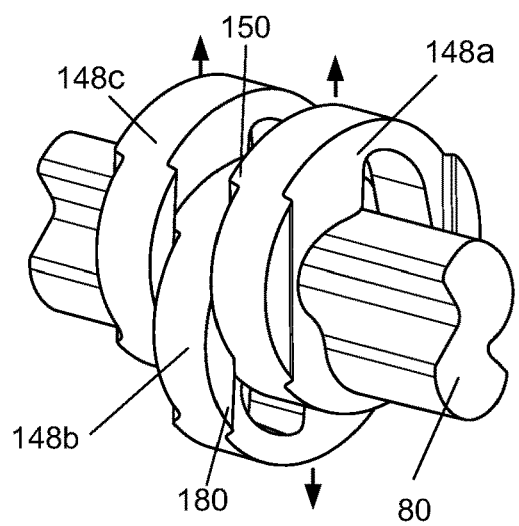

FIGS. 130 and 131 illustrate that the center shaft can be rotated, as shown by arrow. When the center shaft is rotated, the lobes can exert forces against the expandable elements. The expandable elements can be translated in a direction substantially perpendicular to the longitudinal axis of the center shaft. For example, the first and third expandable elements can translate toward the up, as shown by arrows. The second expandable element can translate down, as shown by arrows.

Figure 132:
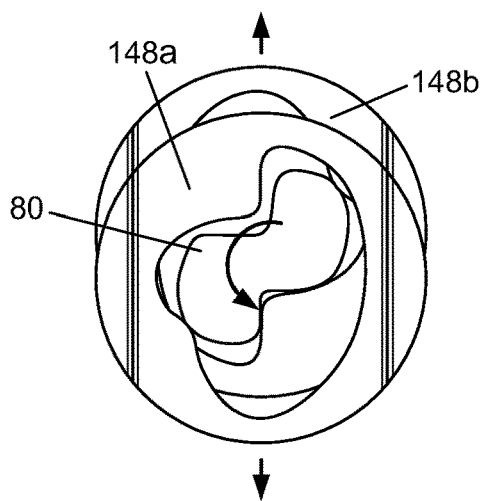
FIGS. 132 and 133 are front and perspective views, respectively, of the variation of the expandable section of FIGS. 128 and 129 in a radially expanded configuration.
Figure 133:
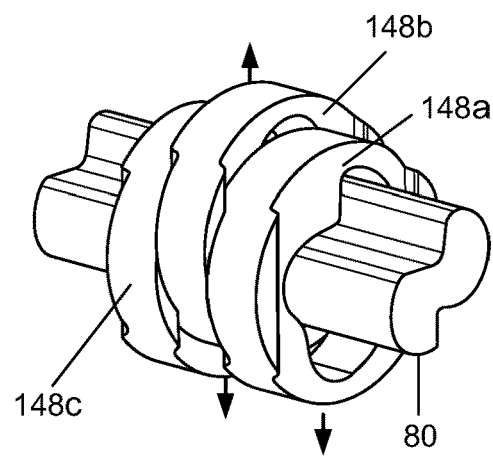

FIGS. 132 and 133 illustrates that the center shaft can be rotated in the opposite direction as shown in FIGS. 130 and 131. The expandable elements can translate in the opposite direction as shown from FIG. 131.

Figure 134:
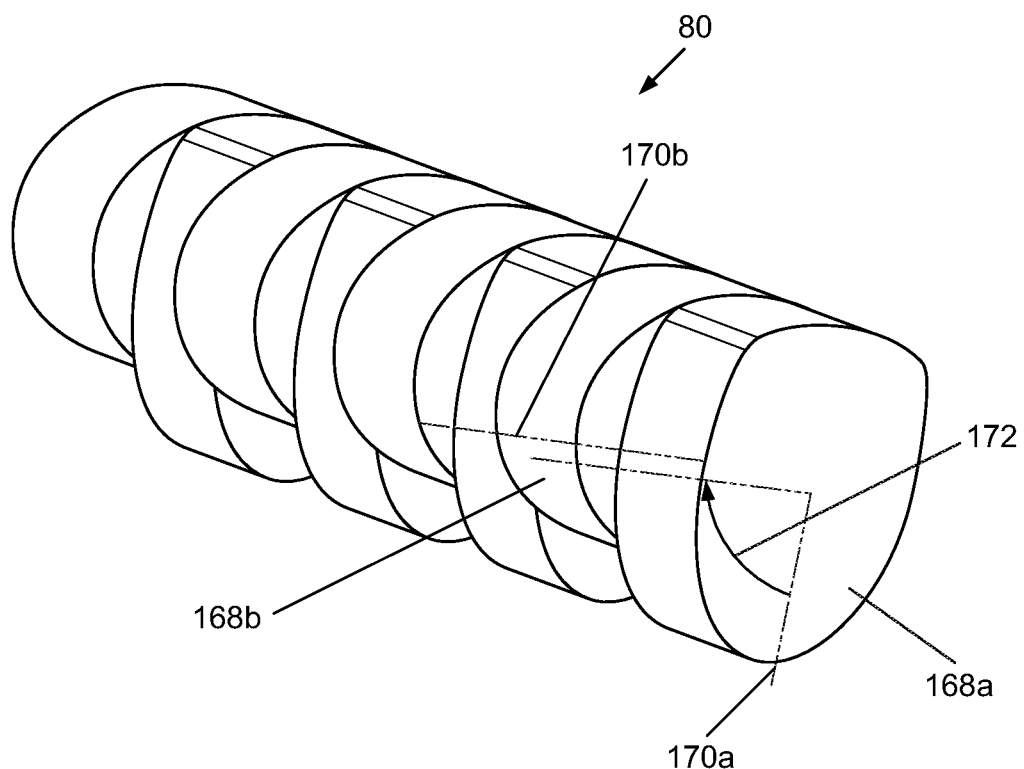
FIGS. 134 and 135 are perspective and side views, respectively, of a variation of the center shaft.
Figure 135:
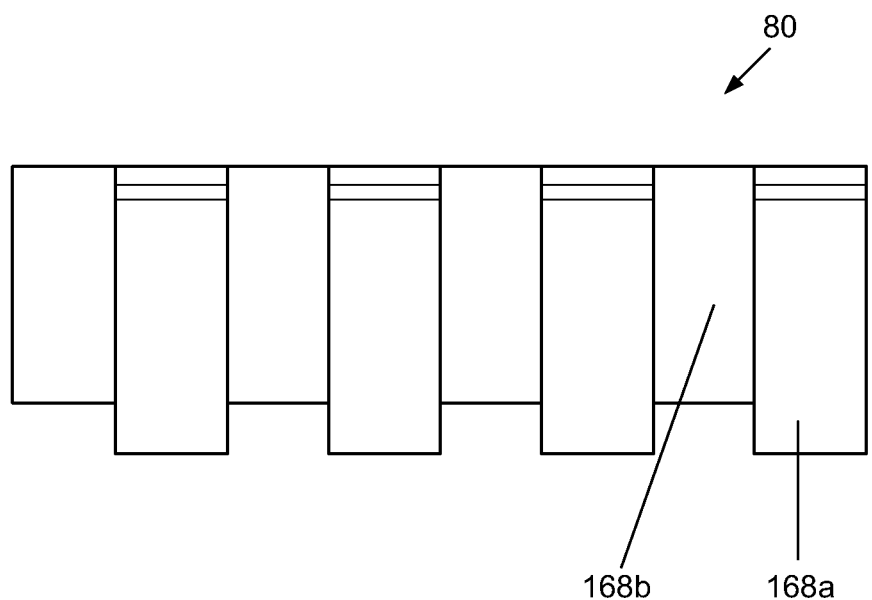

FIGS. 134 and 135 illustrate a center shaft that can have alternating first lobes and second lobes along the length of the center shaft. The first lobes can have a first lobe axis. The second lobes can have a second lobe axis. When viewed in the same plane, the angle between the first lobe axis and the second lobe axis can be a lobe angle. The lobe angle can be from about 90° to about 180°. The first lobes can be actuated in an opposite rotational direction than the second lobes.

Figure 136:
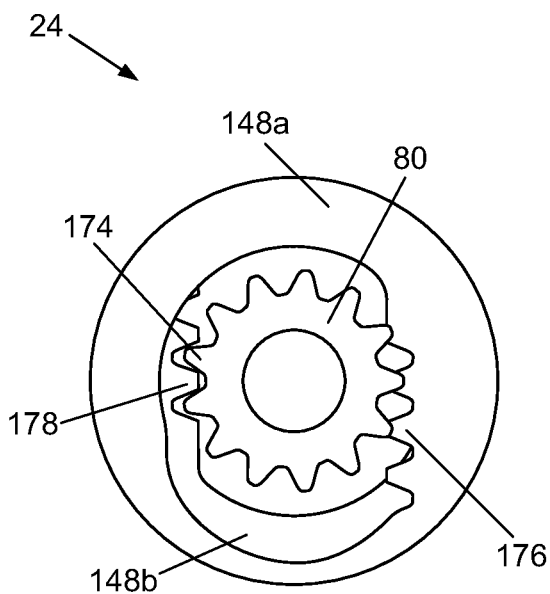
FIG. 136 is an end view of a variation of the expandable section in a radially contracted configuration.

FIG. 136 illustrates an expandable section that can have a first expandable element that can translate in the opposite direction of the second expandable element when the center shaft is rotated. The first expandable element can have first element teeth. The second expandable element can have second element teeth. The element teeth can extend radially inward in the longitudinal channel. The first element teeth can be on the opposite side of the longitudinal channel as the second element teeth. The center shaft can have gear teeth extending radially outward. The gear teeth can engage the first element teeth can the second element teeth.

Figure 137:
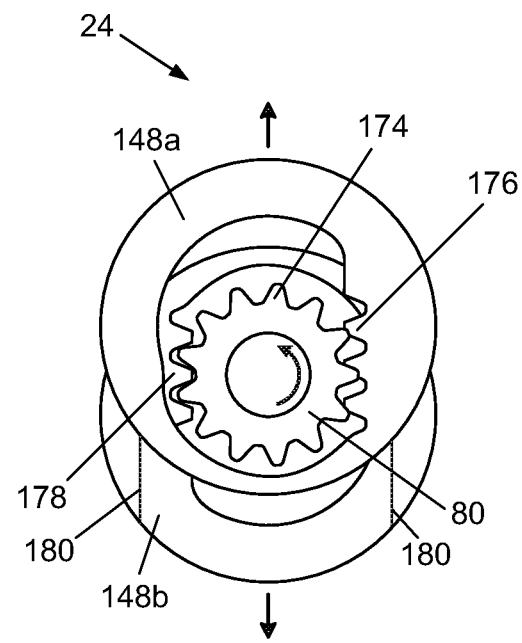
FIG. 137 is an end view of the expandable section of FIG. 136 in a radially expanded configuration.
Figure 138:
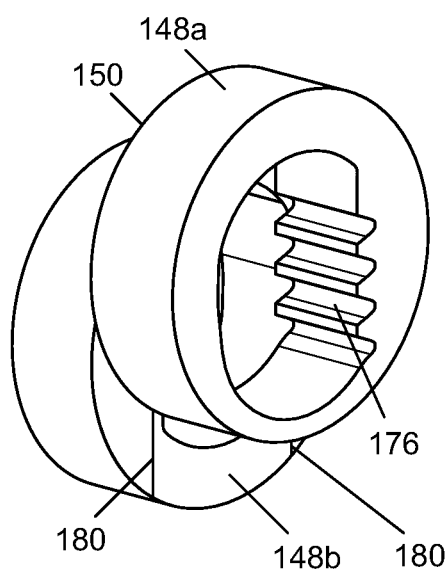
FIG. 138 is a perspective view of the first expandable element and the second expandable element of FIG. 137.
Figure 139:
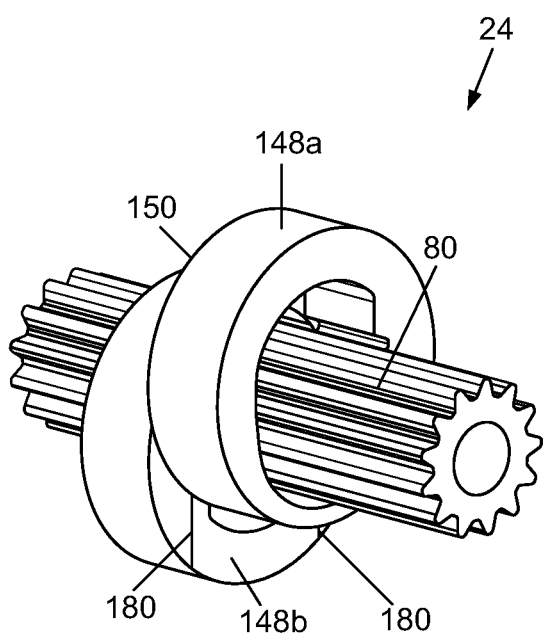
FIG. 139 is a perspective view of the expandable section of FIG. 137.

FIGS. 137 through 139 illustrate that when the center shaft is rotated, the first expandable element can translate up at the same rate that the second expandable element can translate down.

Figure 140:
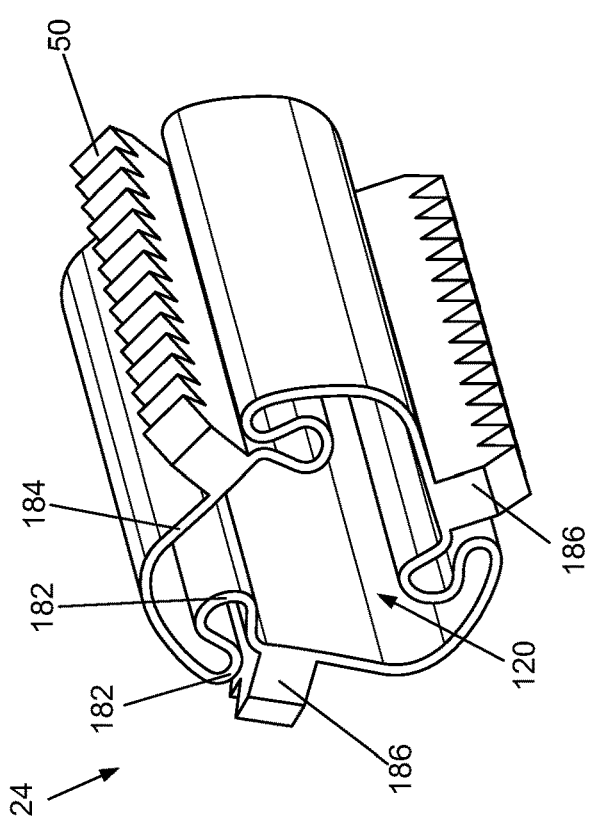

FIG. 140 illustrates an expandable section that can have thread or teeth on one, two, three or more spines extending radially from the wall of the expandable section. In a radially contracted configuration, the wall can have multiple folds, for example two folds between each two adjacent spines. The folds can be unevenly spaced between the adjacent spines.

Figure 141:
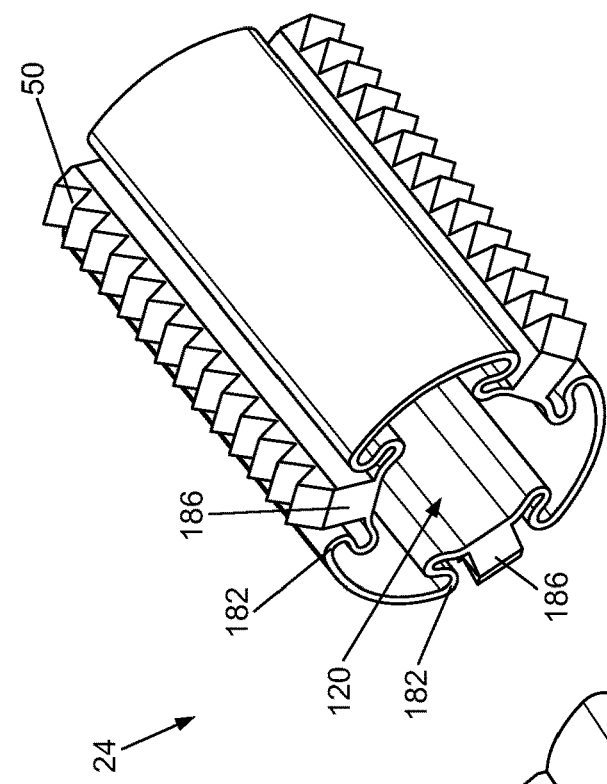
FIGS. 140 through 142 illustrate variations of the expandable section in radially contracted configurations.

FIG. 141 illustrates that the wall can have two folds between each two adjacent spines. The folds can be evenly spaced between the adjacent spines.

Figure 142:
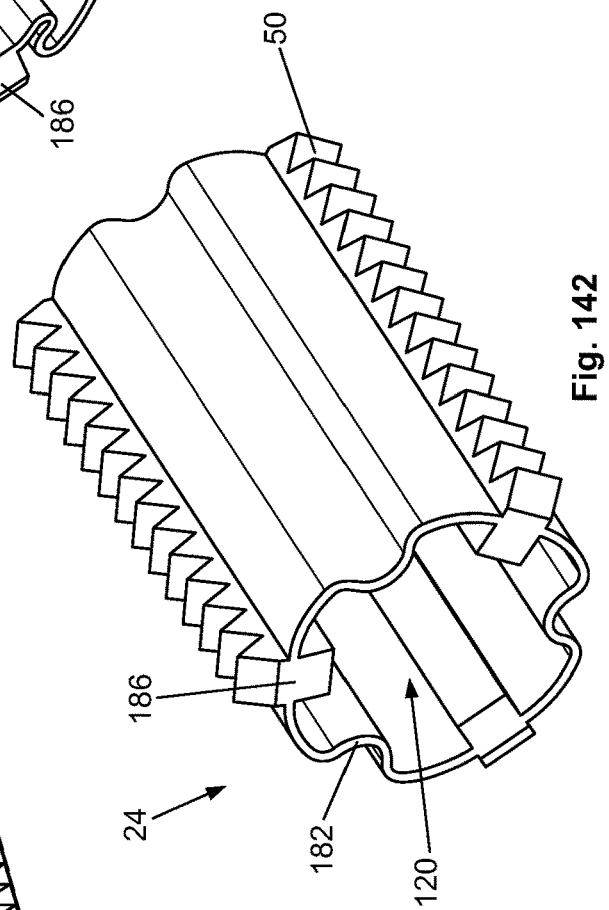

FIG. 142 illustrates that the walls can have one fold between adjacent spines. The spines can extend radially inward and/or outward from the wall.

Figure 143:
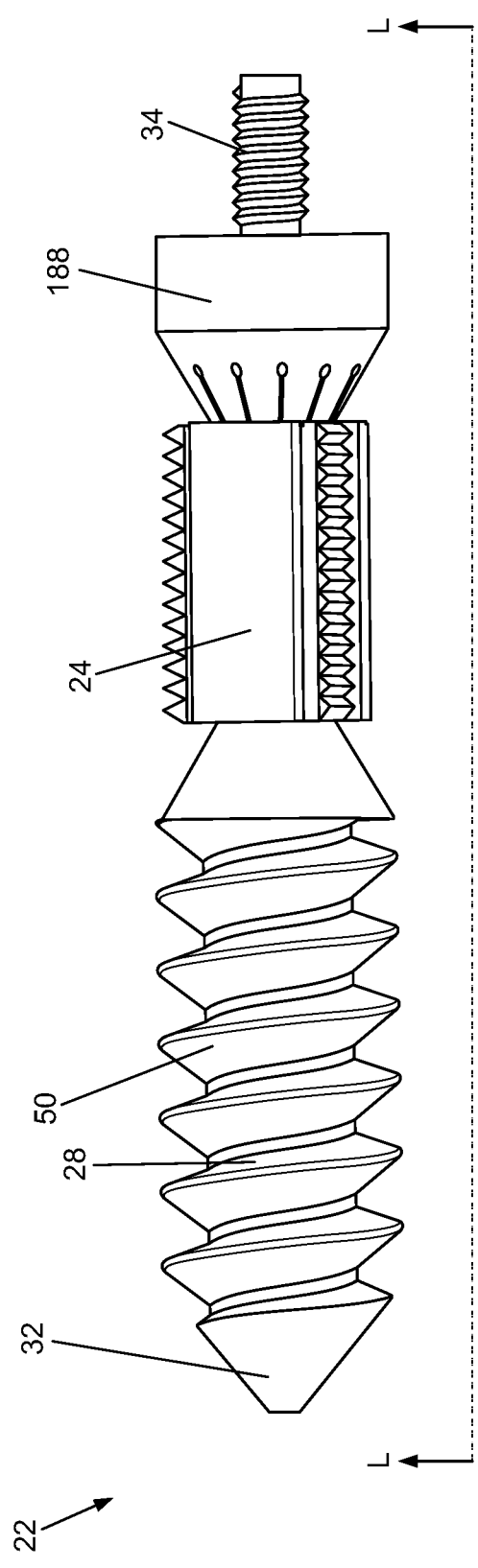
FIG. 143 illustrates a variation of the expandable attachment device with the expandable section of FIG. 141.
Figure 144:
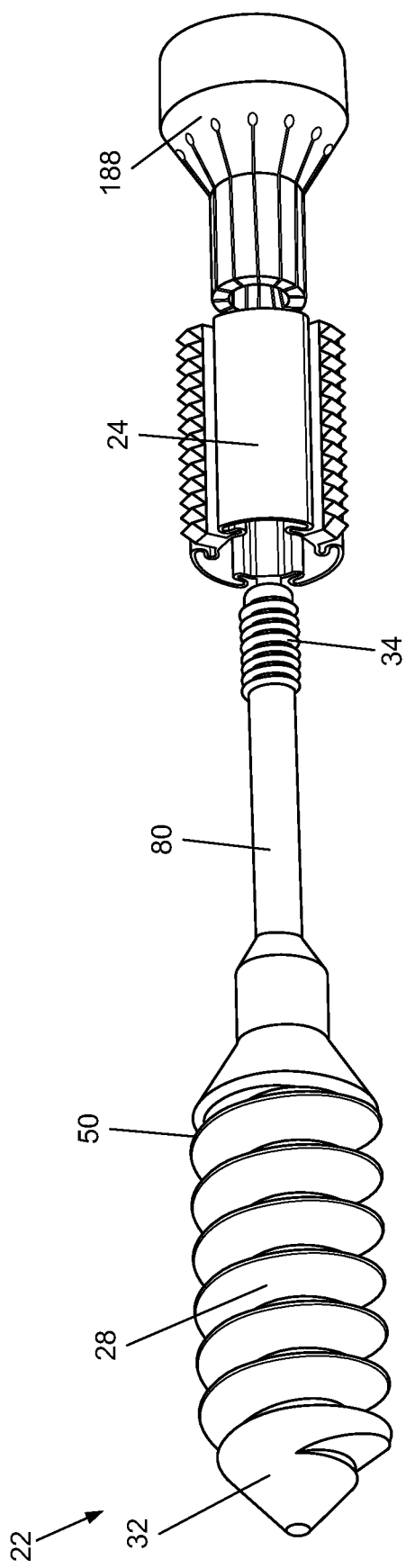
FIG. 144 illustrates an unassembled expandable attachment device of FIG. 143.

FIGS. 143 and 144 illustrate that the expandable section (shown for exemplary purposes as the expandable section of FIG. 141) can be loaded on the center shaft of an expandable attachment device. The expandable section can be placed between a first cone and a second cone on the expandable attachment device. The expandable attachment device can have a mandrel. The second cone can be part of the mandrel.

Figure 145:
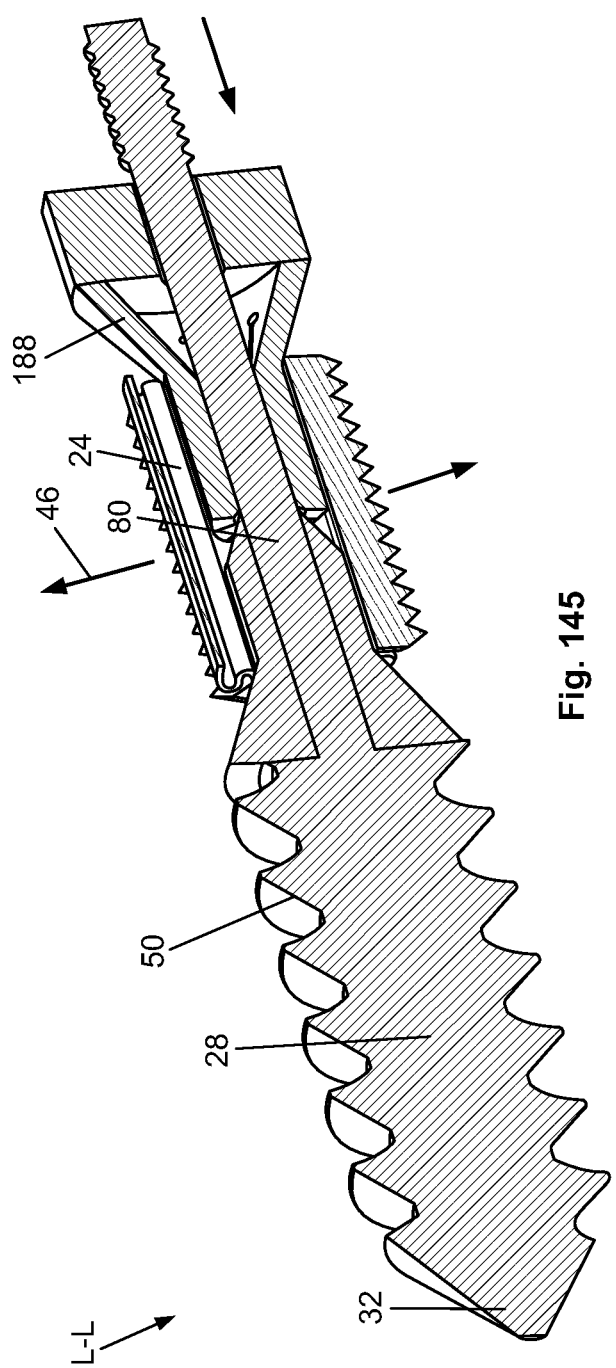
FIG. 145 illustrates a variation of cross-section L-L of FIG. 143 during use.

FIG. 145 illustrates that the mandrel can be pushed, as shown by arrow, toward the expandable section. The expandable section can radially expand as shown by arrow.

The distal end can be configured to attach to a separate device, such as a fixation rod or plate. The distal end can be threaded.

Figure 146:
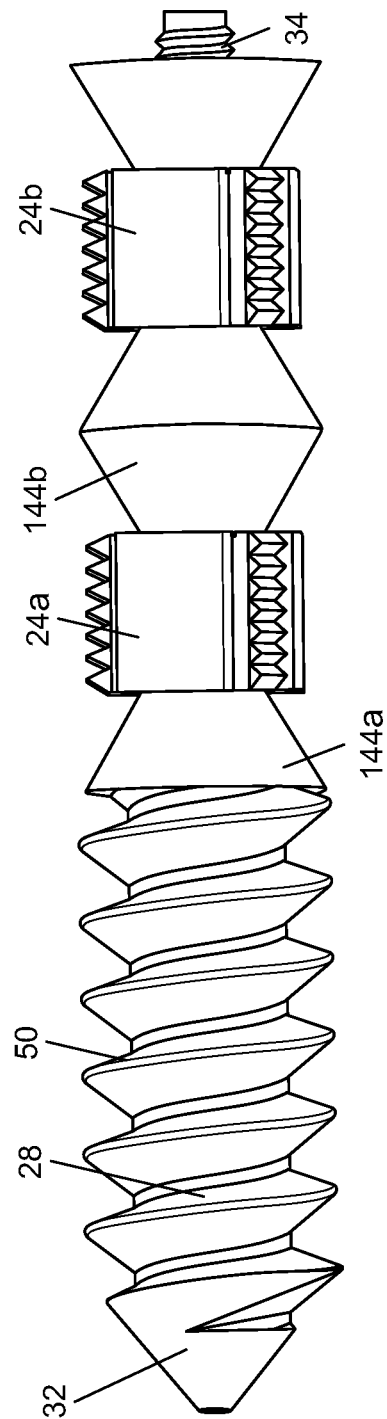
FIG. 146 illustrates a variation of the expandable attachment device.

FIG. 146 illustrates that the expandable attachment device can have a first expandable section and a second expandable section. Each expandable section can be between a first cone and a second cone, and can be radially expanded as described herein, including as shown in FIG. 145.

Figure 147:
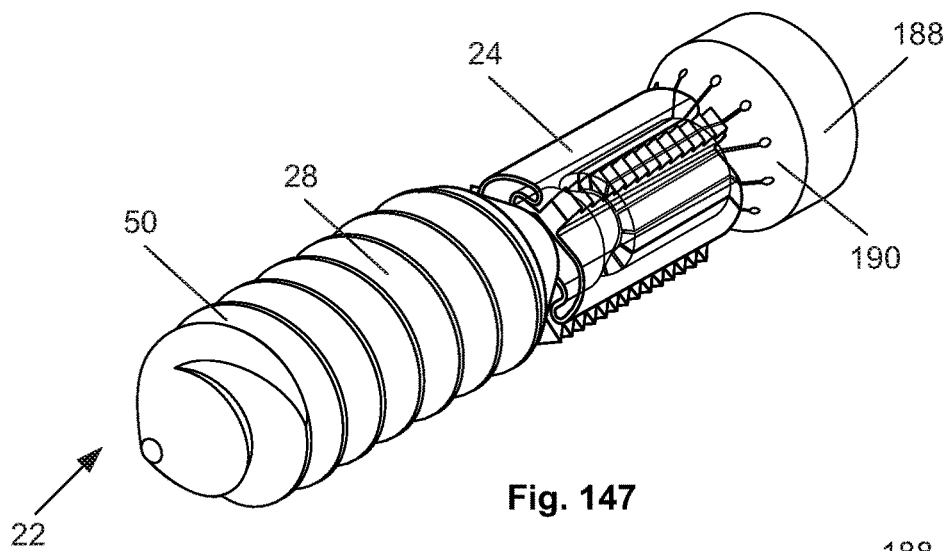
FIGS. 147, 148 and 149 illustrate variations of the expandable attachment device with the expandable section of FIGS. 140, 141 and 142, respectively.
Figure 148:
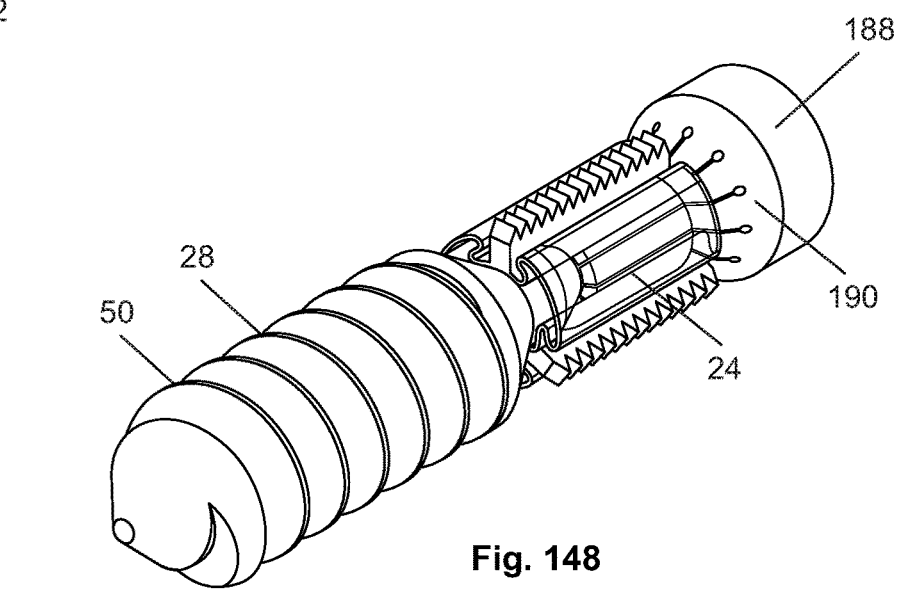
Figure 149:
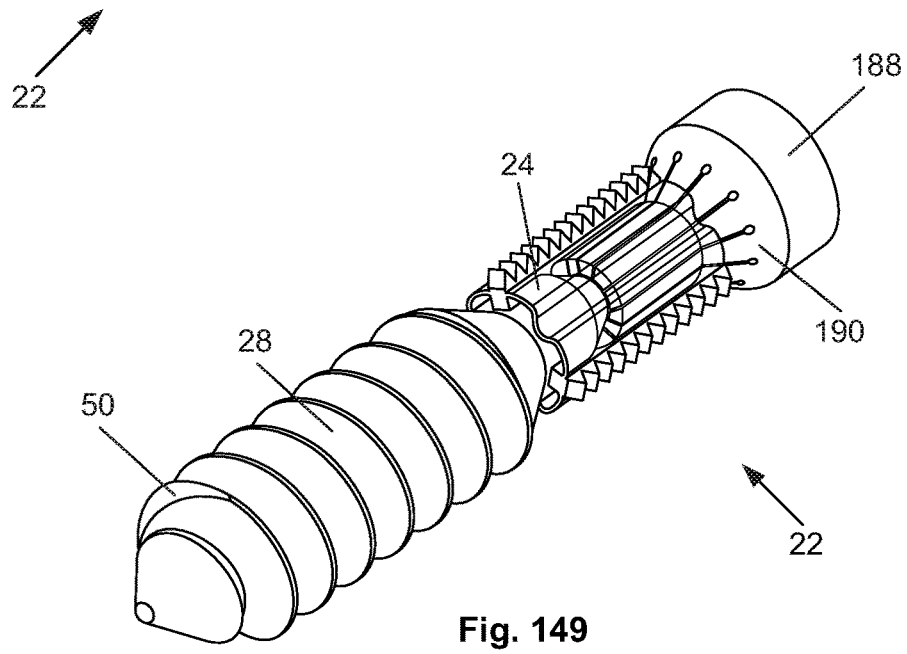
Figure 151:
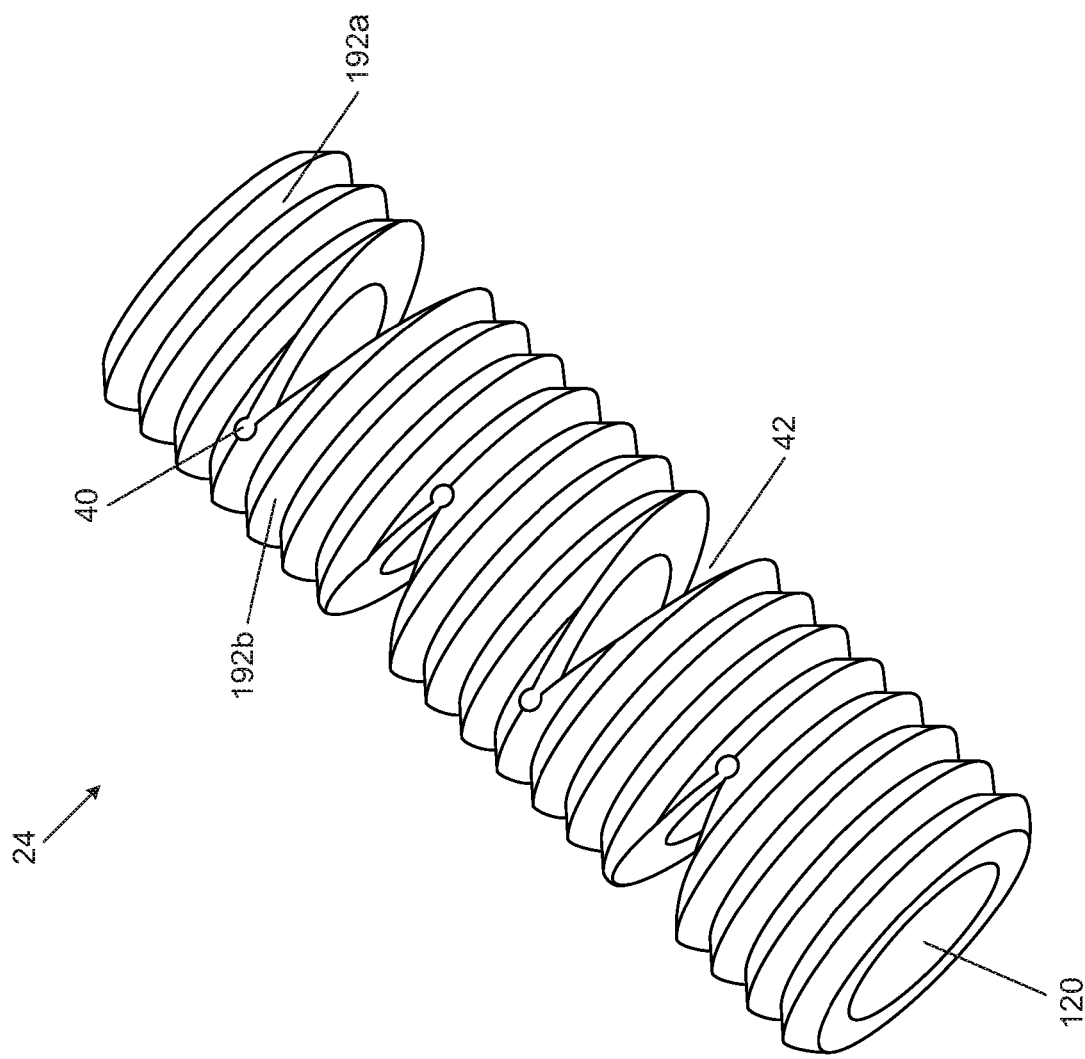
FIGS. 150 and 151 illustrate side and perspective views, respectively, of a variation of the expandable section in a radially contracted configuration.

FIGS. 147 through 149 illustrate the expandable sections of FIGS. 140 through 142, respectively, loaded on the center shaft of the expandable attachment device.

Figure 150:
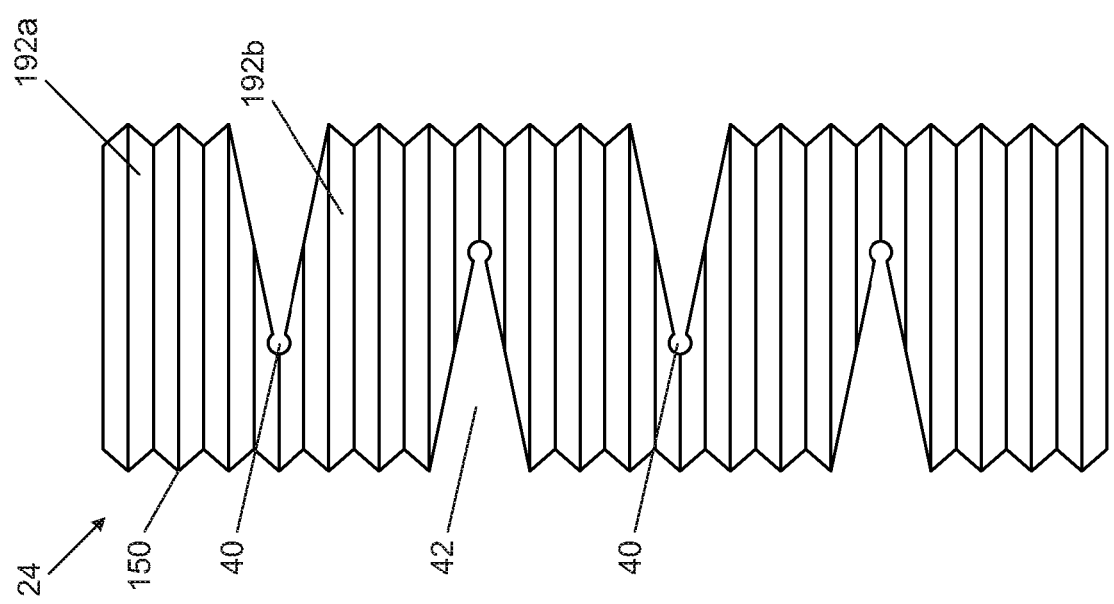
Figure 153:
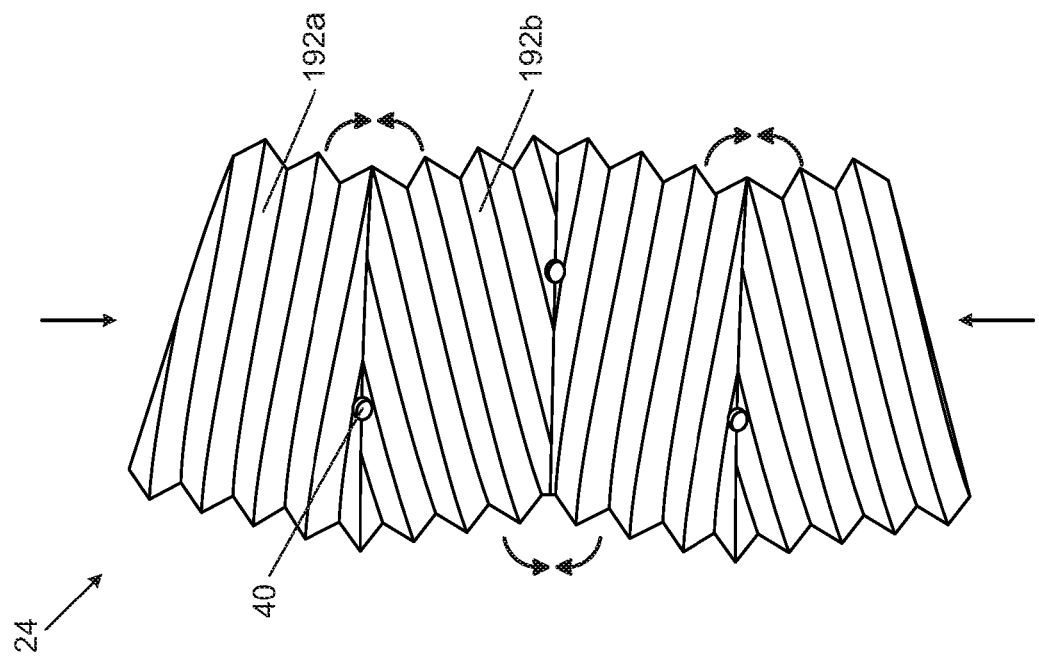
FIGS. 152 and 153 illustrate variations of the expandable section in radially expanded configurations.

FIGS. 150 and 153 illustrate that the expandable section can have about four angled ports. Each port can have a joint. Between two adjacent ports can be an individual expandable segment, for example the first expandable segment and the second expandable segment, as shown.

Figure 152:
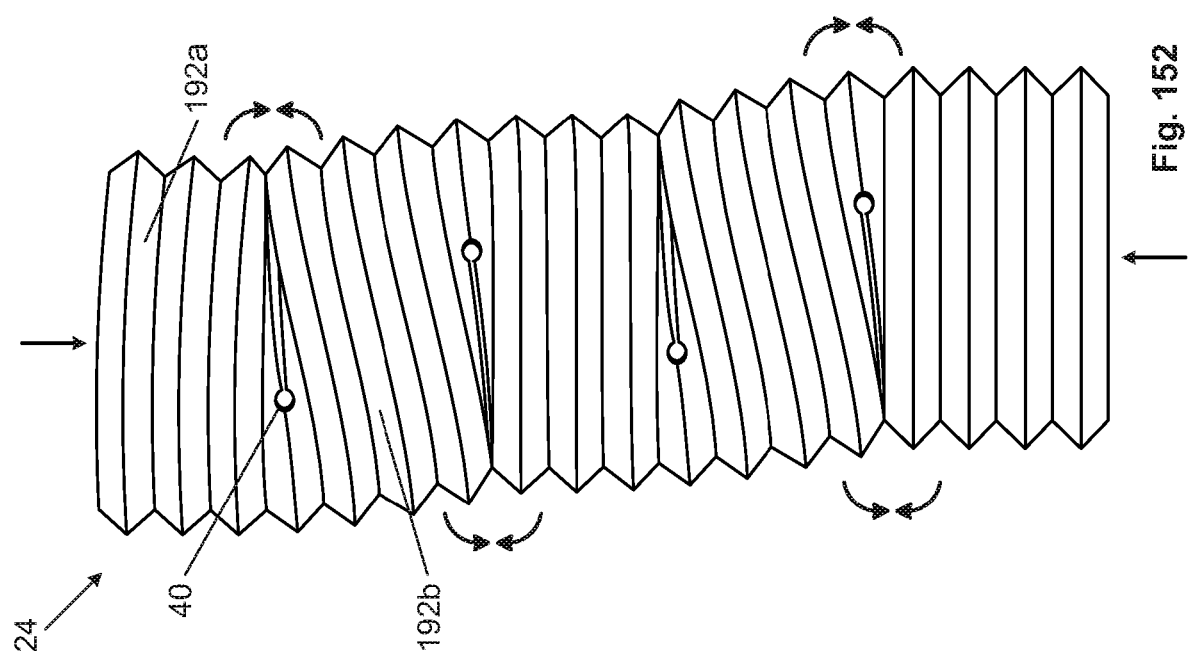

FIG. 152 illustrates that a longitudinally compressive force, as shown by arrows, can be applied to the expandable section. The expandable segments can rotate, as shown by arrows, around the adjacent joints. The ports can close. In the radially expanded configuration, the expandable section can have a distal end shifted laterally from the proximal end.

FIG. 153 illustrates that the expandable section can have larger ports and/or the expandable section can be over compressed, causing deformation after the ports have closed. The distal end and the proximal end of the expandable section can be laterally aligned.

Figure 154:
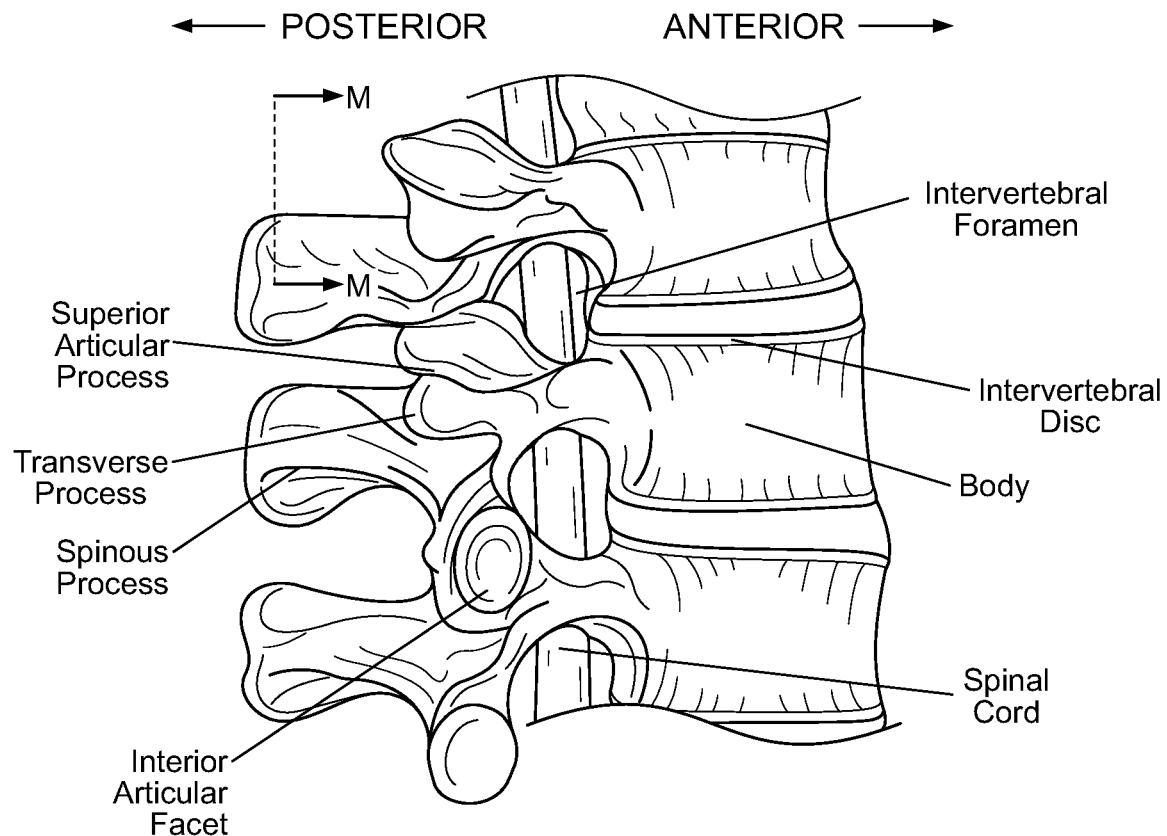
FIG. 154 is a lateral view of the spine.
Figure 155:
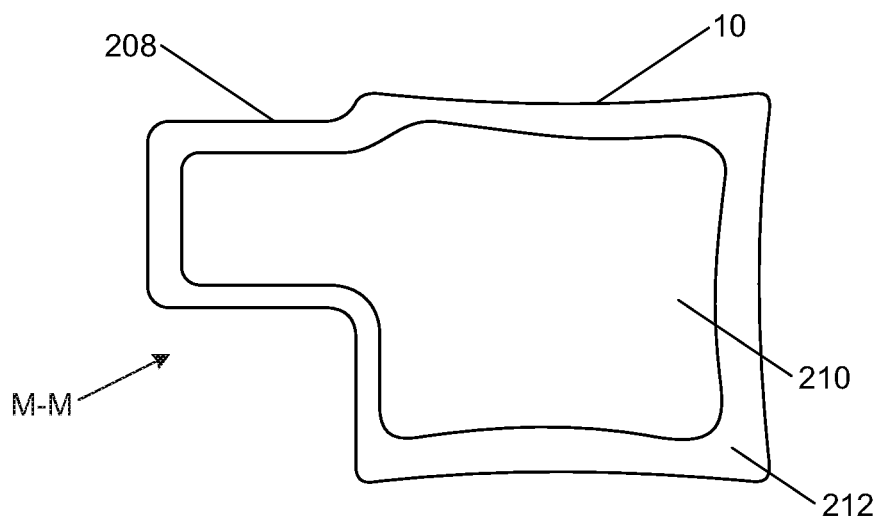
FIG. 155 illustrates cross-section M-M of FIG. 154.

FIG. 154 illustrates a side view of a spine. FIG. 155 illustrates that harder, cortical bone surrounds softer, cancellous bone in the vertebra.

Figure 156:
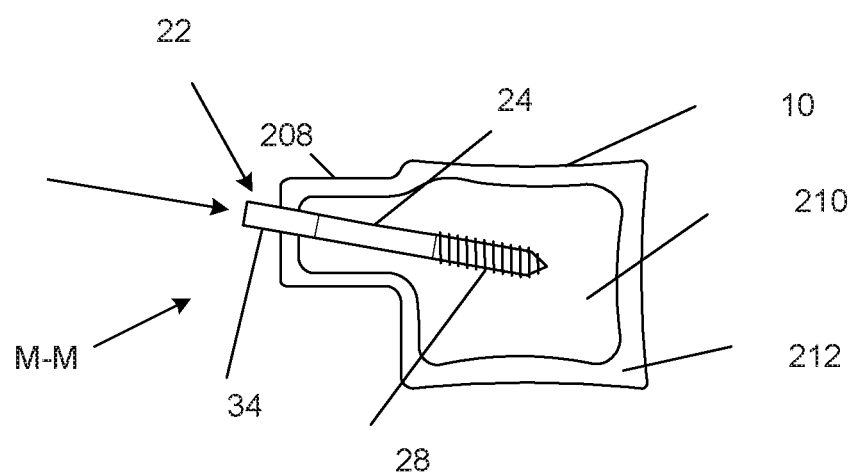
FIG. 156 illustrates cross-section M-M of FIG. 154 with an expandable attachment device delivered into the pedicle and/or vertebral body.

FIG. 156 illustrates that the expandable attachment device can be translated and/or rotated into the pedicle and/or into the vertebral body. The expanded section can be positioned in the cortical bone.

Figure 157:
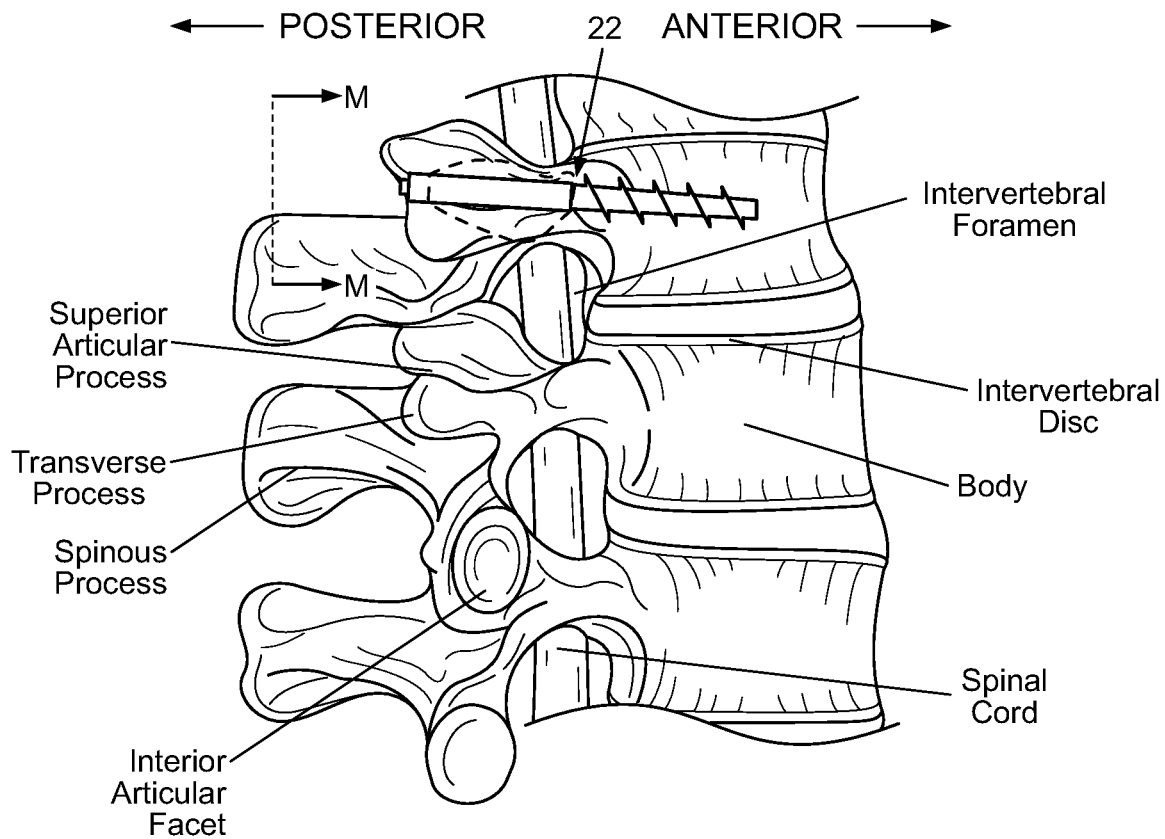
FIG. 157 is a partial see-through lateral view of the spine with a variation of the expandable attachment device delivered to, and radially expanded in, the pedicle and/or vertebral body.
Figure 158:
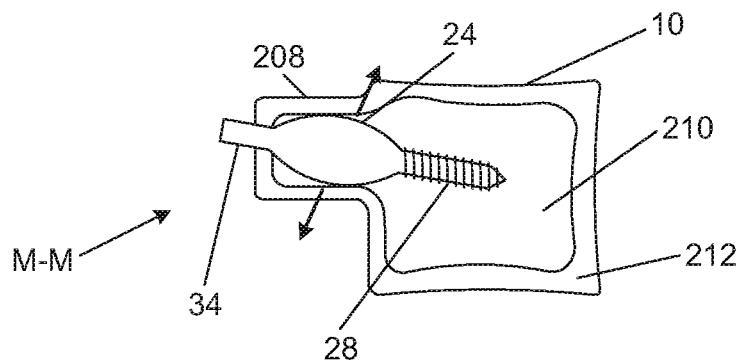
FIG. 158 illustrates cross-section M-M of FIG. 157.

FIGS. 157 and 158 illustrate that the expandable section can be radially expanded, for example in the cancellous bone of the pedicle and/or the vertebral body. The radius of the radially expanded section can be larger than the entry hole created to insert the attachment device into the vertebra.

The distal end can extend from the bone. A separate device, such as a fixation rod or plate, can be attached to the distal end.

Figure 159:
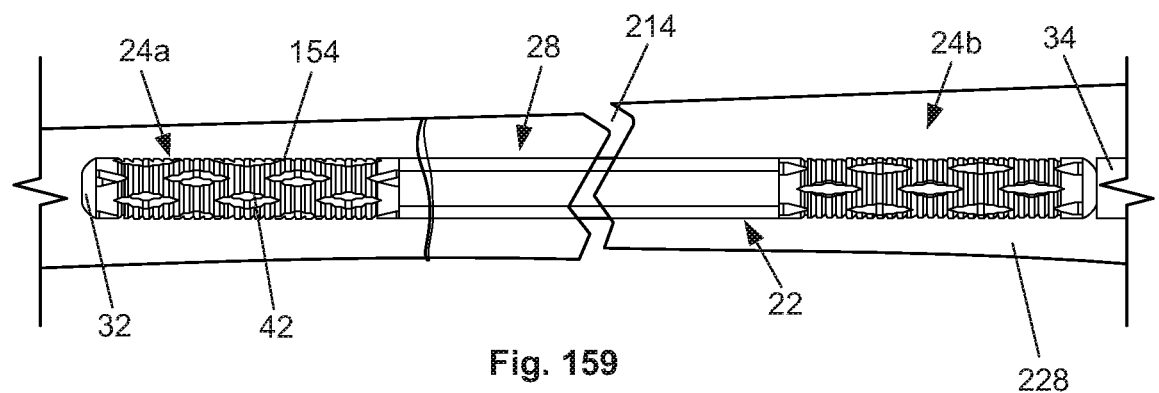
FIG. 159 illustrates a variation of a method for using a variation of the expandable attachment device to treat a broken bone.

FIG. 159 illustrates that an expandable attachment device can be used to treat a long bone break, such as in the femur or humerus. The expandable attaclunent device can be inserted into the cancellous and/or cortical part of the bone. The expandable attachment device can be positioned to have a first exp~ndable section on a first side of the bone fracture. The expandable attachment device can be positioned to have a second expandable section on a second side of the bone fracture. The expandable attachment device can have an unexpandable section between the first and second expandable sections. The unexpandable section can be positioned across the bone fracture.

Figure 160:
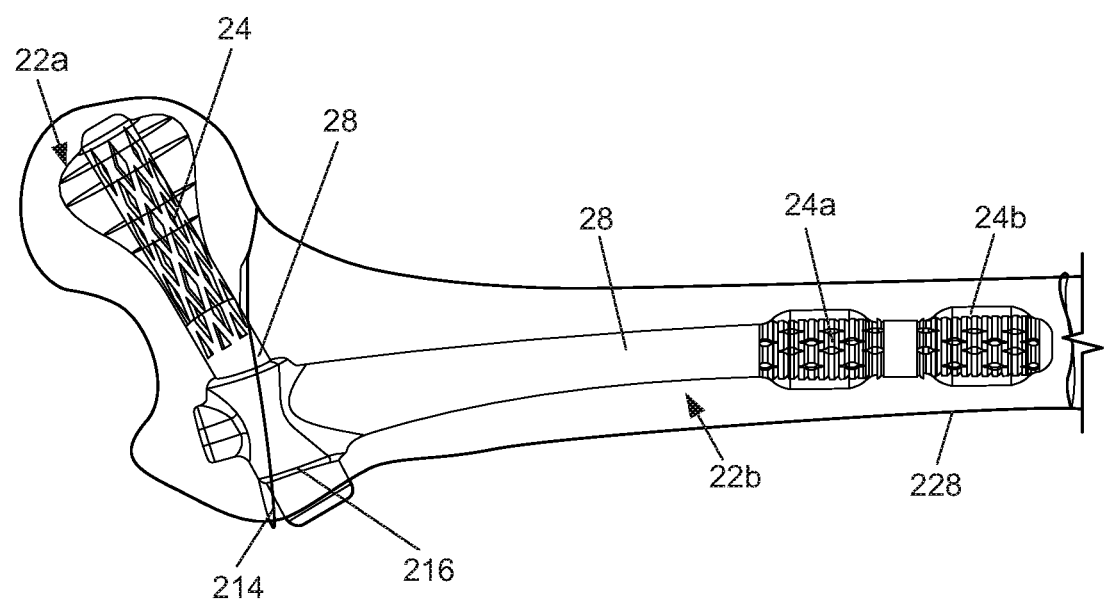
FIG. 160 illustrates a variation of a method for using two variations of the expandable attachment devices to treat a broken bone.

FIG. 160 illustrates that a first expandable attachment device 22*a* can be placed in a first section of the bone (e.g., the femur head). A second expandable attachment device 22*b* can be placed in a second section of the bone. The second expandable attachment device 22*b* can have a collar configured to fixedly receive the unexpandable section of the first expandable attachment device. The unexpandable section of the first expandable attachment device 22*a* can be fixedly attached to the collar.

Figure 161:
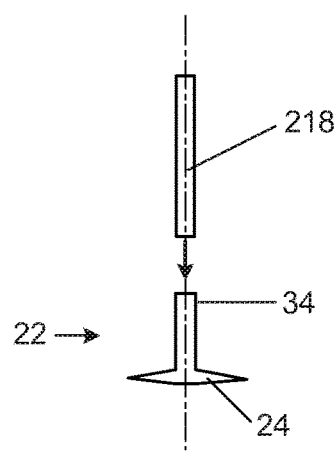
FIGS. 161 and 162 illustrate a variation of a method for attaching an end attachment to the remainder of a variation of the expandable attachment device.
Figure 162:
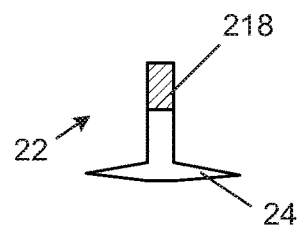
Figure 163:
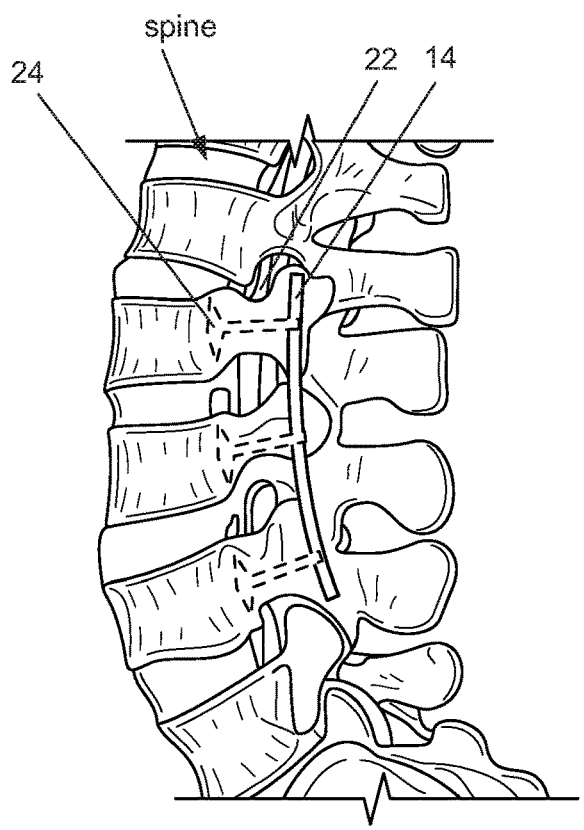
FIG. 163 illustrates a variation of method for using a variation of the expandable attachment devices with a fixation rod in the spine.
Figure 164:
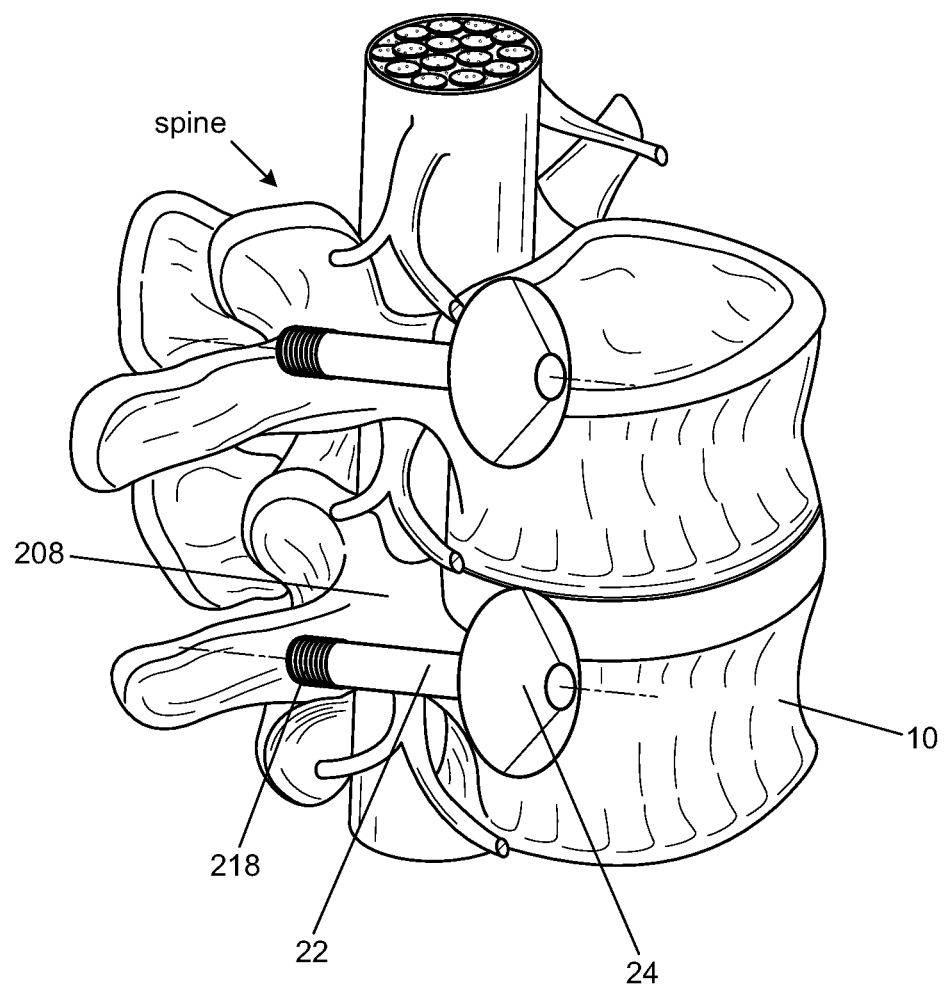
FIG. 164 illustrates a variation of a method for using a variation of the expandable attachment devices with end attachments in the spine.

FIGS. 161 and 162 illustrates that the expandable attachment device can have an end attachment configured to be attached, as shown by arrow, to the distal end. For example, the expandable attachment device can be positioned in a bone and radially expanded. The end attachment can be attached to the distal end, as shown in FIG. 164. The end attachment can be configured to attach to a separate device, such as a fixation rod or plate, as shown in FIG. 163.

Figure 165:
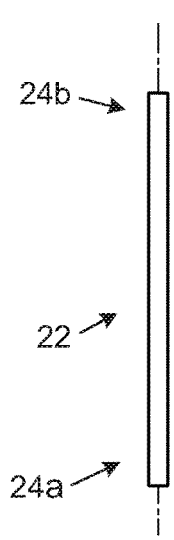
FIGS. 165 through 167 illustrate a variation of a method for expanding first and second expandable sections on a variation of the expandable attachment device.
Figure 166:
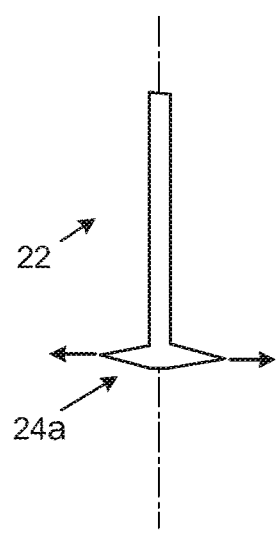
Figure 167:
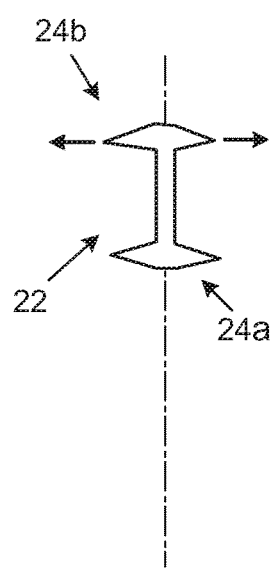

FIG. 165 through 166 illustrates that the expandable attachment device can be deployed by radially expanding the first expandable section at a first end, and concurrently or subsequently, radially expanding the second expandable section at a second end.

Figure 168:
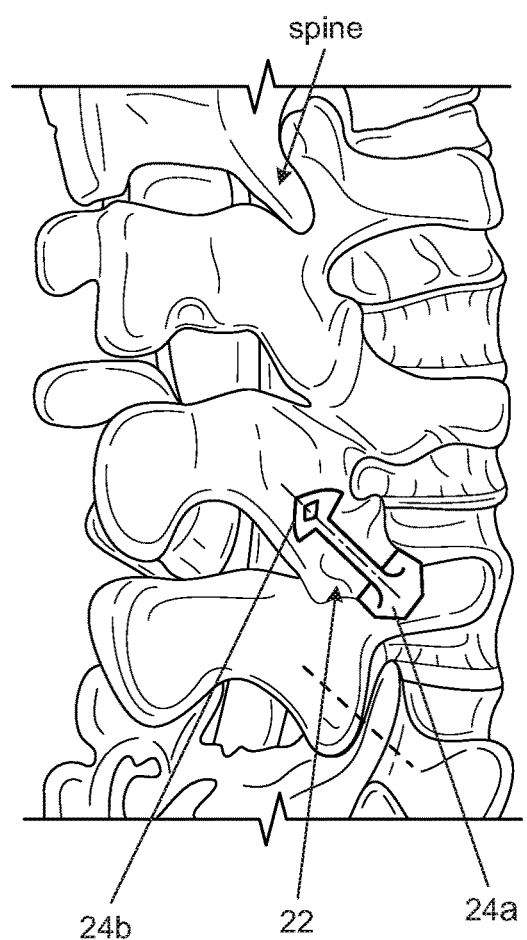
FIGS. 168 and 169 illustrate variations of methods for using a variation of the expandable support device in the spine.
Figure 169:
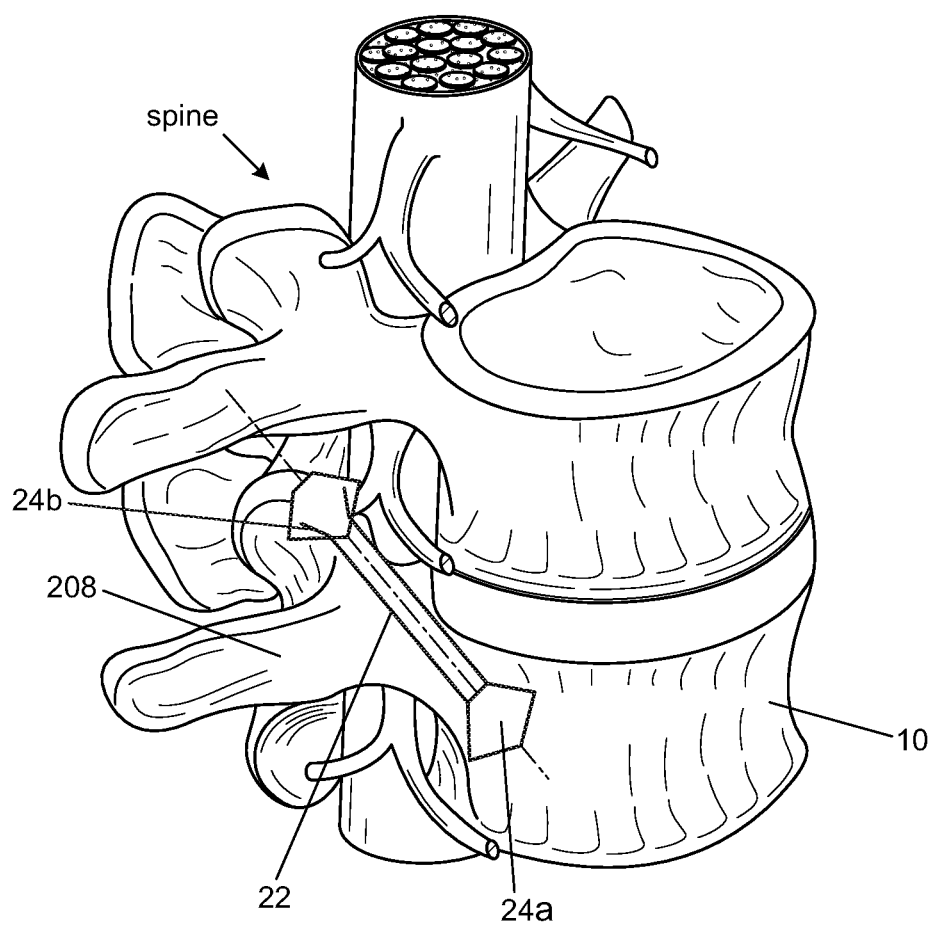

FIGS. 168 and 169 illustrate that the expandable attachment device can be positioned so the first expandable section can be radially expanded in the pedicle or vertebral body. The second expandable section can be radially expanded in the pedicle, vertebral body, or outside the bone, for example in the soft tissue or in a virtual space. A separate device, such as a fixation rod or plate can be attached to the second expandable section.

Figure 172:
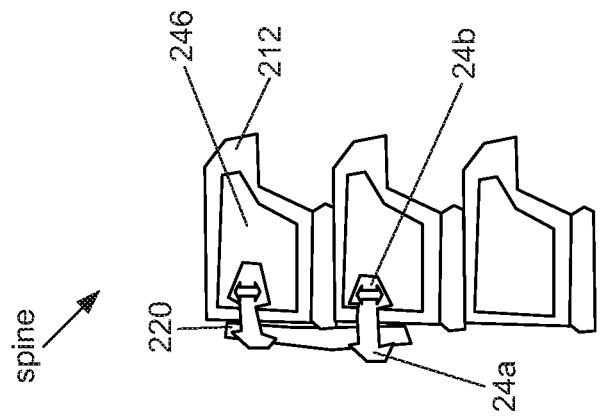
FIGS. 171 and 172 are sagittal cross-sections of a variation of a method for using the expandable attachment device in a spine with a fixation plate.
Figure 171:
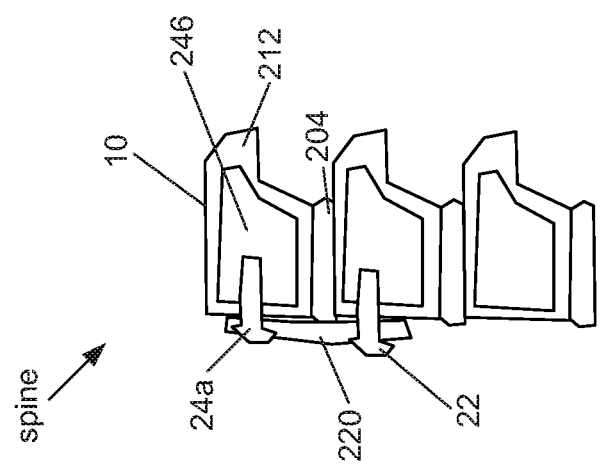
Figure 170:
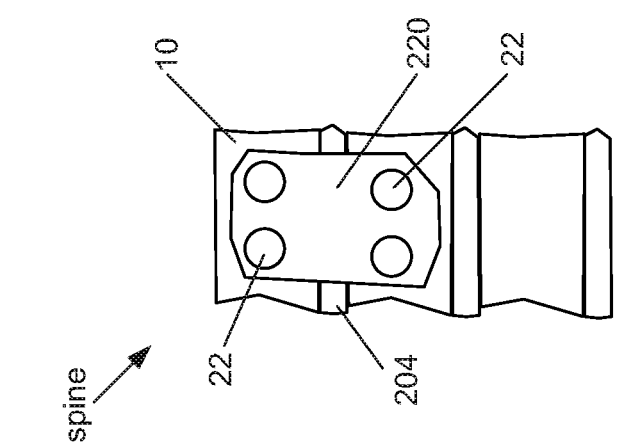
FIG. 170 is an anterior view of a variation of a method for using the expandable attachment device in a spine with a fixation plate.

FIGS. 170 through 172 illustrate that a fixation plate can be attached to the anterior side of the spine. FIG. 171 illustrates that the expandable attachment devices can be attached to the fixation plate and the first expandable section can be radially expanded. FIG. 172 illustrates that the second expandable sections of the expandable attachment devices can be positioned in the cancellous bone. The second expandable sections can be radially expanded, as shown by arrows, in the cancellous bone, for example in the vertebral body.

Figure 173:
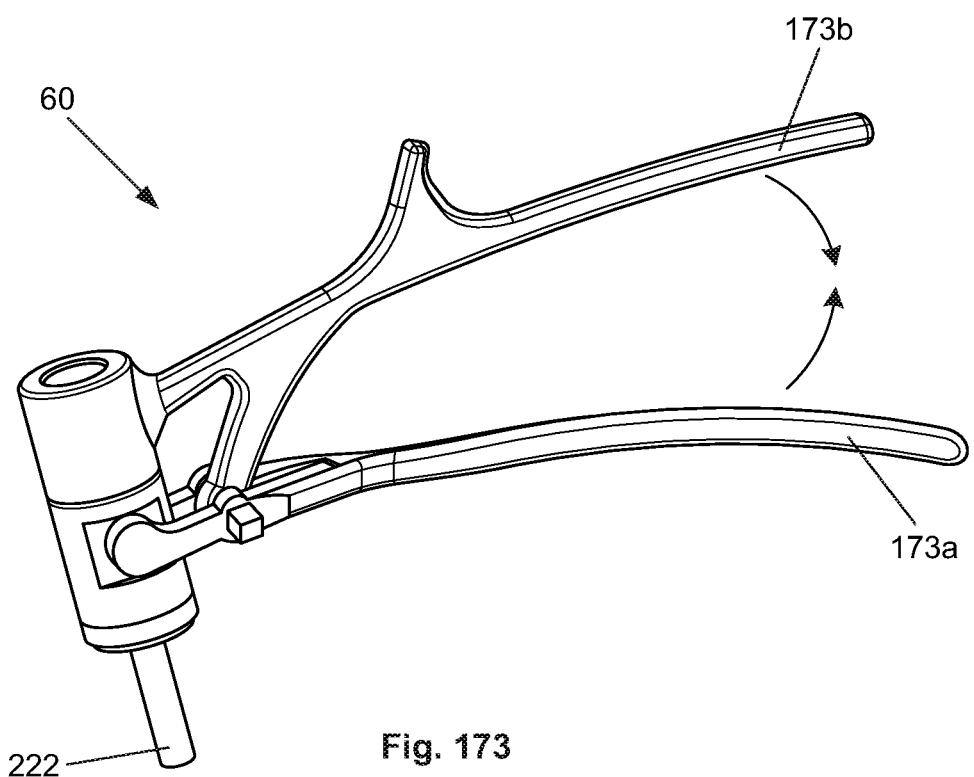
FIG. 173 illustrates a variation of the deployment tool.

FIG. 173 illustrates that the deployment tool can have a first handle rotatably attached to a second handle. Rotating the first handle and the second handle towards each other, as shown by arrows, can result in longitudinal compression of the expandable section of the expandable attachment device. See the incorporated applications for additional elements of the deployment tool. The expandable attachment device can be removably attached to the deployment head.

Figure 174:
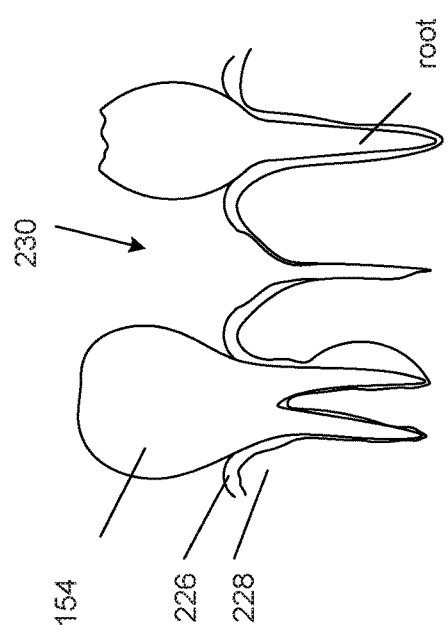
FIGS. 174 through 178 illustrate a variation of a method for implanting a variation of the expandable attachment device for use as a tooth anchor.

FIG. 174 illustrates that an oral space can have a missing tooth. The missing tooth can be surrounded on one side, both sides or neither side, by teeth. The gum, bone, and teeth roots are also shown.

Figure 175:
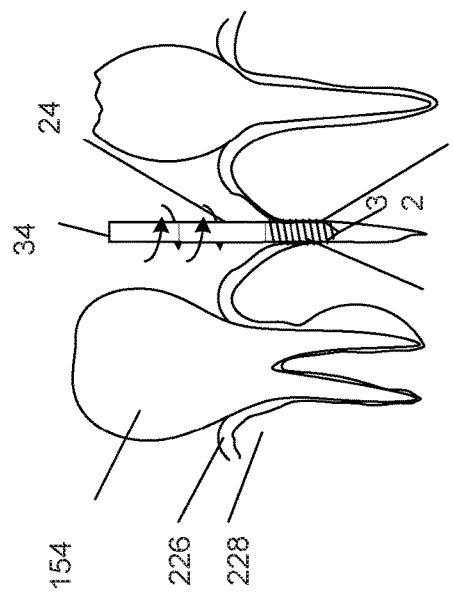
Figure 176:
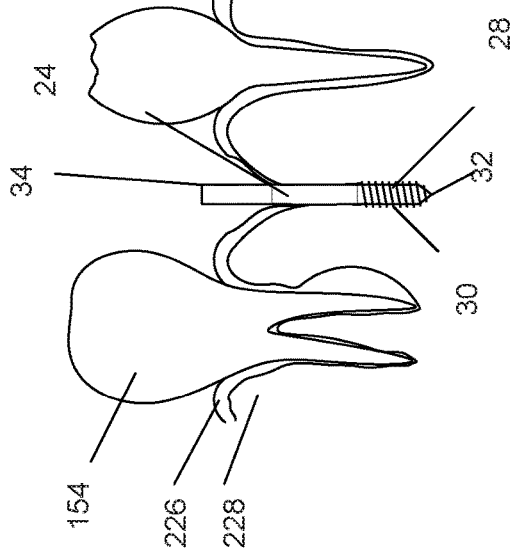

FIG. 175 illustrates that the expandable attachment device can be screwed (e.g., rotation and translation), as shown by arrows, into the missing tooth space in the bone. The unexpandable thread can compact or cut bone as the expandable attachment device is inserted into the missing tooth space in the bone. FIG. 176 illustrates that the expandable support device can be fully inserted into the bone. The distal end can extend above the gum.

Figure 177:
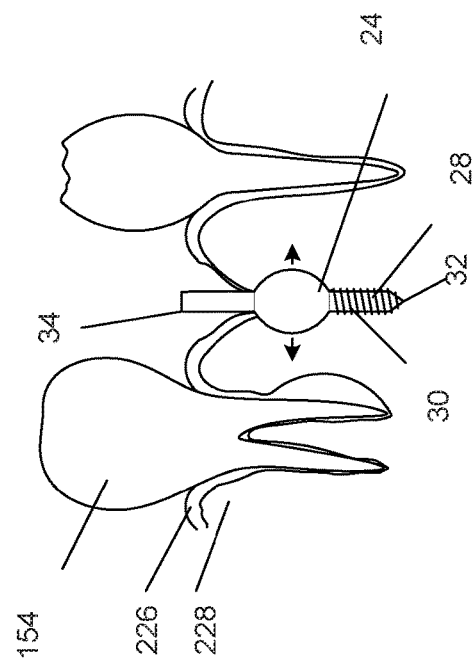

FIG. 177 illustrates that the expandable section can be radially expanded, as shown by arrows, for example with the expandable support device fully inserted into the bone.

Figure 178:
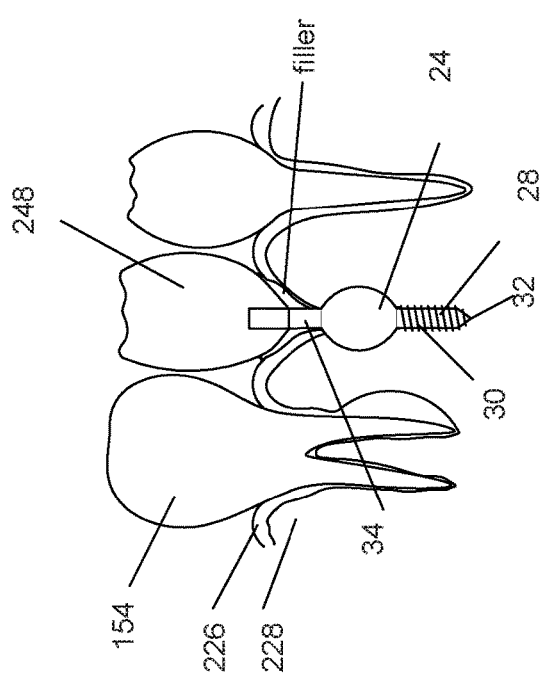

FIG. 178 illustrates that a replacement tooth can be fixedly or removably attached to the distal end. The distal end can be configured to attach to the replacement tooth (e.g., thread, one or more latches, clasps, locks). The replacement tooth can be positioned between the adjacent teeth. The space between the replacement tooth and the gum can be partially or completely filled by a filler, for example a biocompatible cement (e.g., a bone cement).

Figure 179:
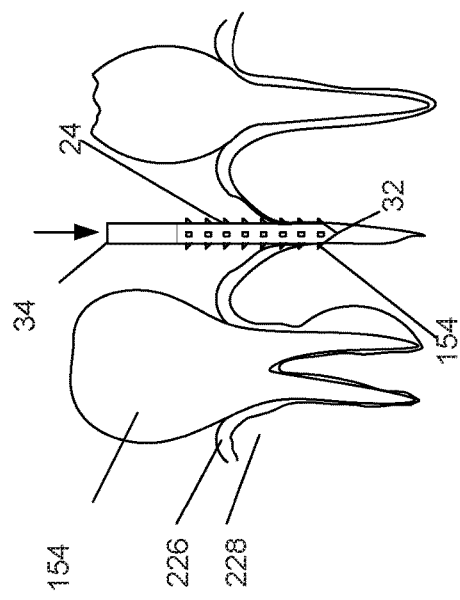
FIGS. 179 and 180 illustrate a variation of a method for implanting a variation of the expandable attachment device for use as a tooth anchor.

FIG. 179 illustrates that the expandable attachment device can have unidirectional and/or one-way teeth along all or part of the length of the expandable section. The expandable section can be along substantially the entire length of the expandable attachment device, for example, except for the distal end configured to attach to the replacement tooth.

Figure 180:
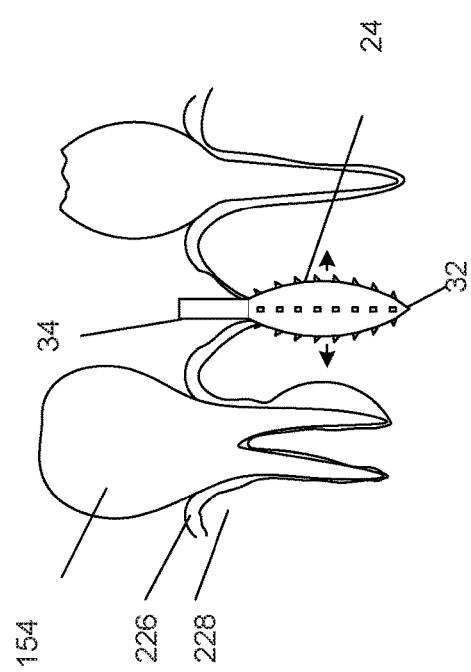

FIG. 180 illustrates that the expandable section can be radially expanded, as shown by arrows. The replacement tooth can then be attached as shown in FIG. 178.

Figure 181:
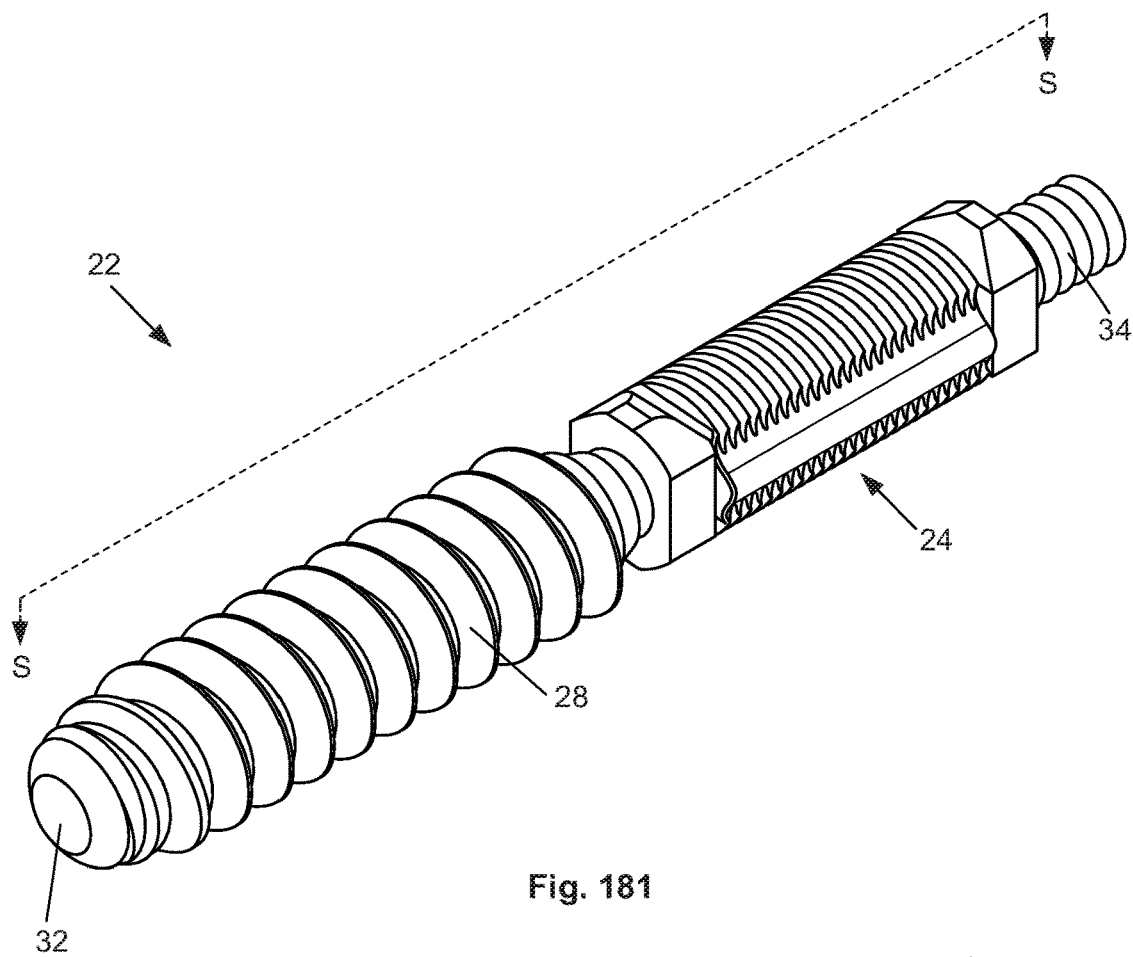
Figure 182:
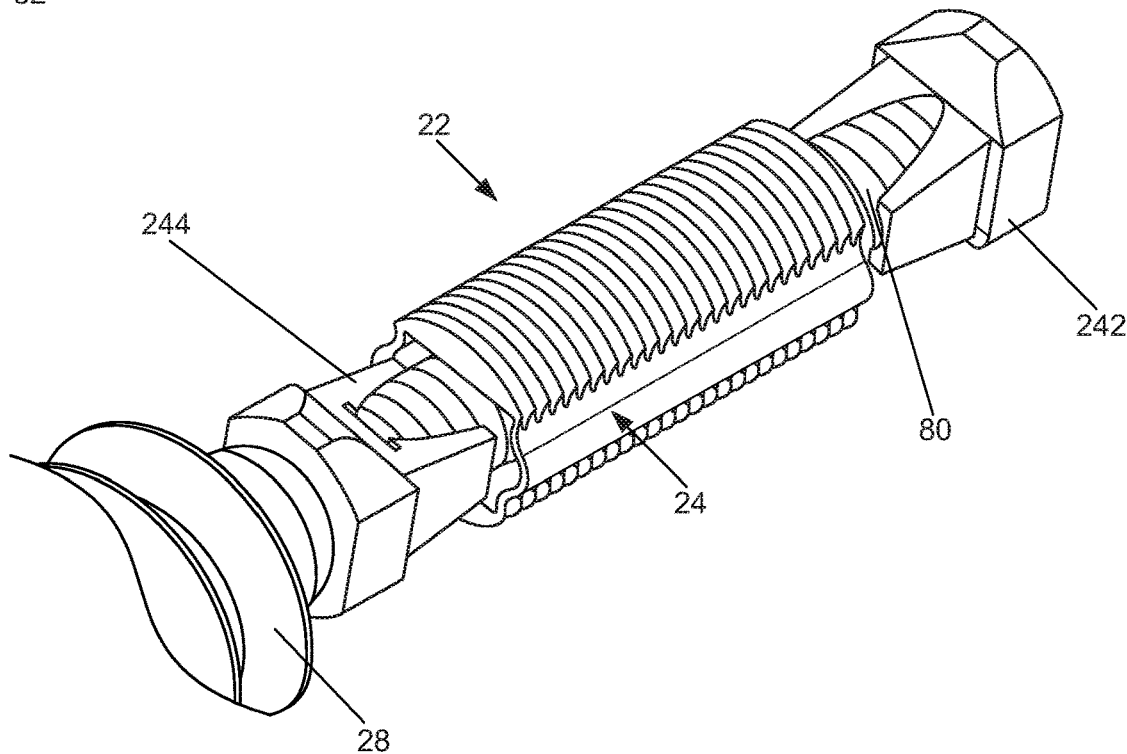

FIGS. 181 and 182 illustrate that the expandable section can have expandable threads around one or more sections of the expandable section (e.g., for example on opposite sides of the expandable section, as shown). The distal wedge and/or the proximal wedge can have threads on the internal diameter or be threadless on the internal diameter. The internal threads can engage the proximal length of the center shaft (e.g., the proximal length of the center shaft have a smaller, larger or the same diameter as compared to the diameter of the distal length of the center shaft). The proximal wedge can have an internal diameter that can be larger than the threads on the center shaft so the proximal wedge can slide freely over the distal length of the center shaft and/or the proximal length of the center shaft.

Figure 183:
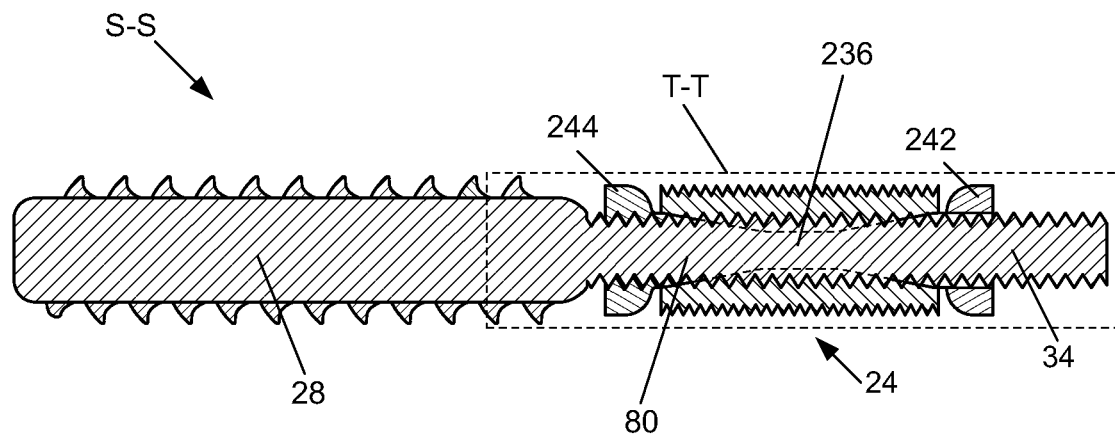
Figure 184:
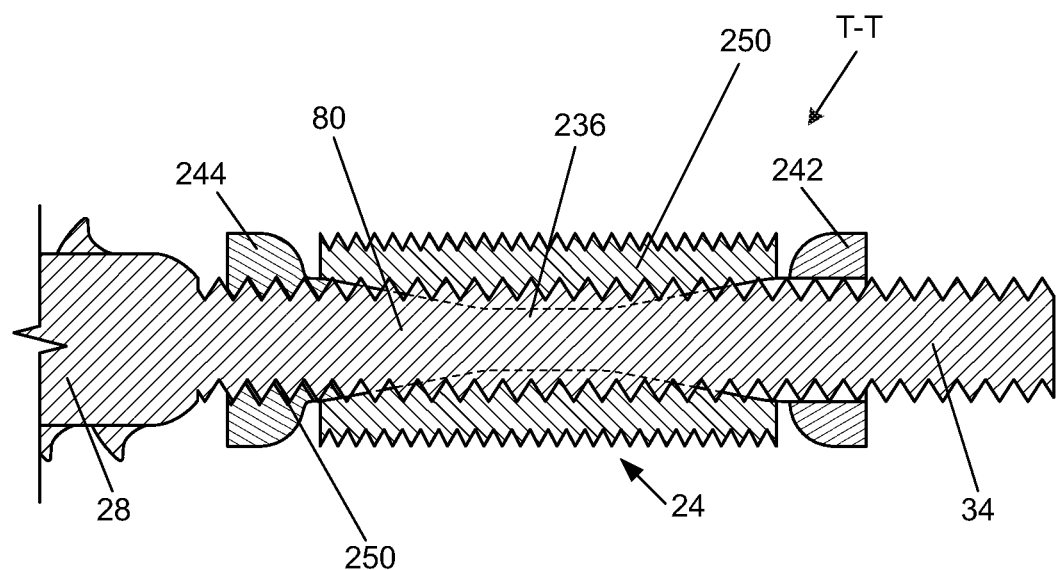

FIGS. 183 and 184 illustrate that the outer diameter of the unexpandable section can be substantially equivalent to the outer diameters of the expandable section (e.g., in a radially contracted configuration) and/or the wedges. The outer diameter of the expandable section (e.g., in a radially contracted configuration) can be slightly larger than, smaller than, or substantially equivalent to the outer diameter of the unexpandable section.

The internal diameter of the expandable section and the internal diameter of one or more of the wedges (e.g., shown as only the proximal wedge in FIGS. 183 and 184) can have internal threads and/or teeth, for example, configured to engage threads and/or teeth on the center shaft.

The center shaft can have a reduced diameter (as shown) at a length near the longitudinal middle of the center shaft. The internal threads or teeth (e.g., on the inner diameter of the expandable section) might no engage the center shaft along the length having the reduced diameter, for example because of no geometric overlap and/or the absence of teeth or threads along the outer diameter of the center shaft along the length having the reduced diameter.

Figure 185:
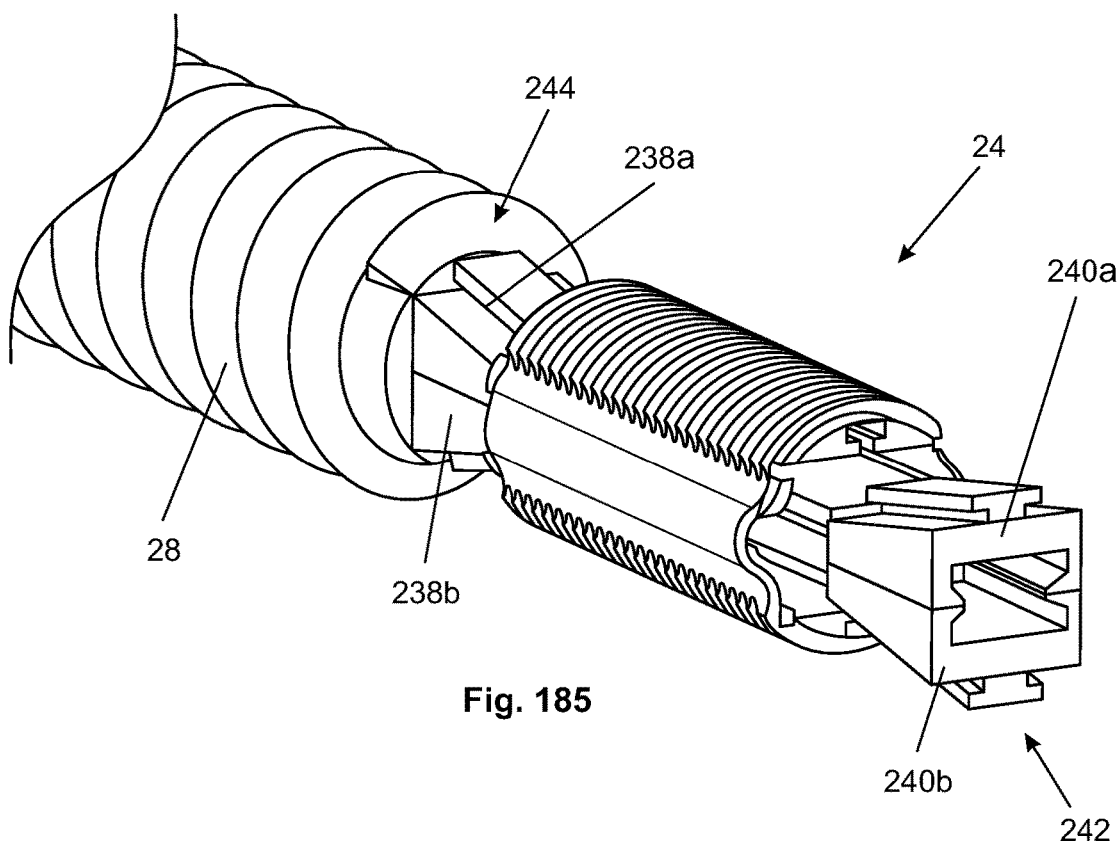
Figure 186:
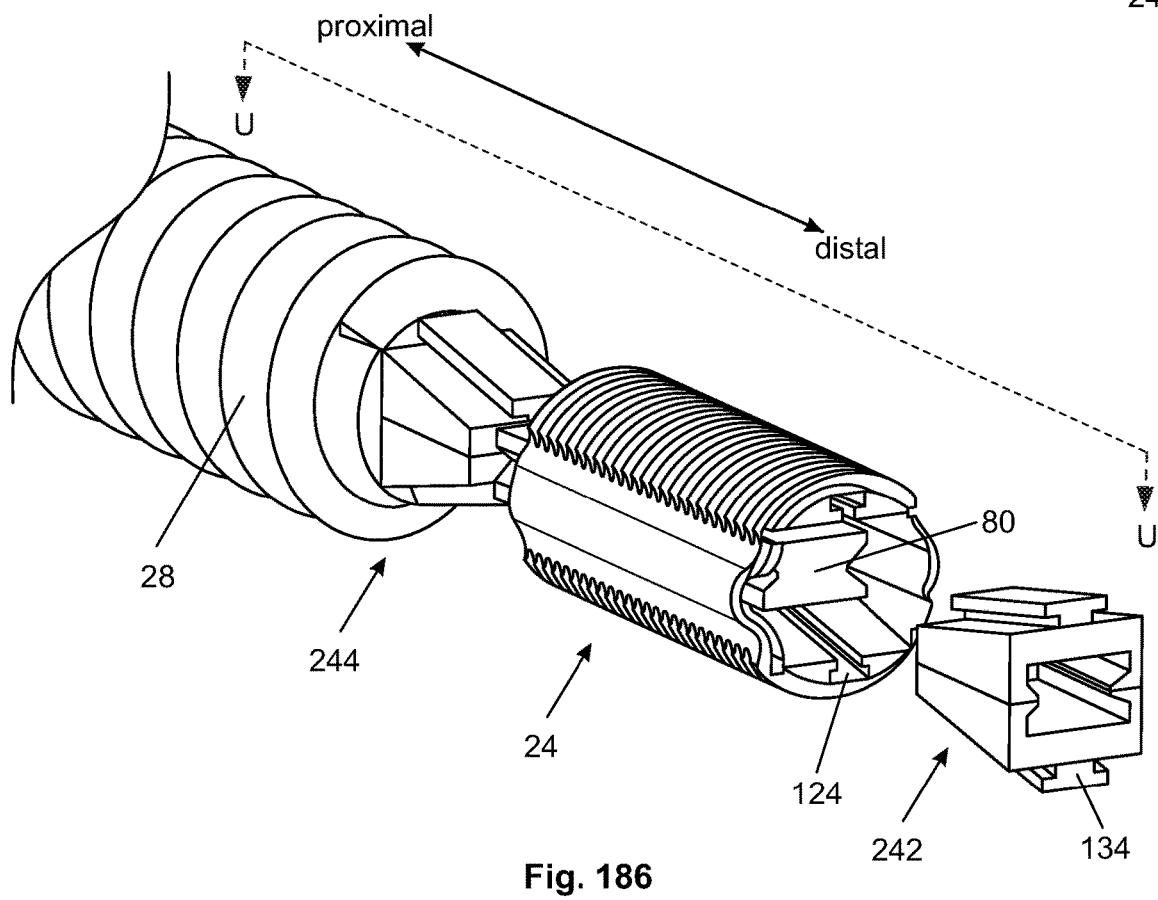
Figure 187:
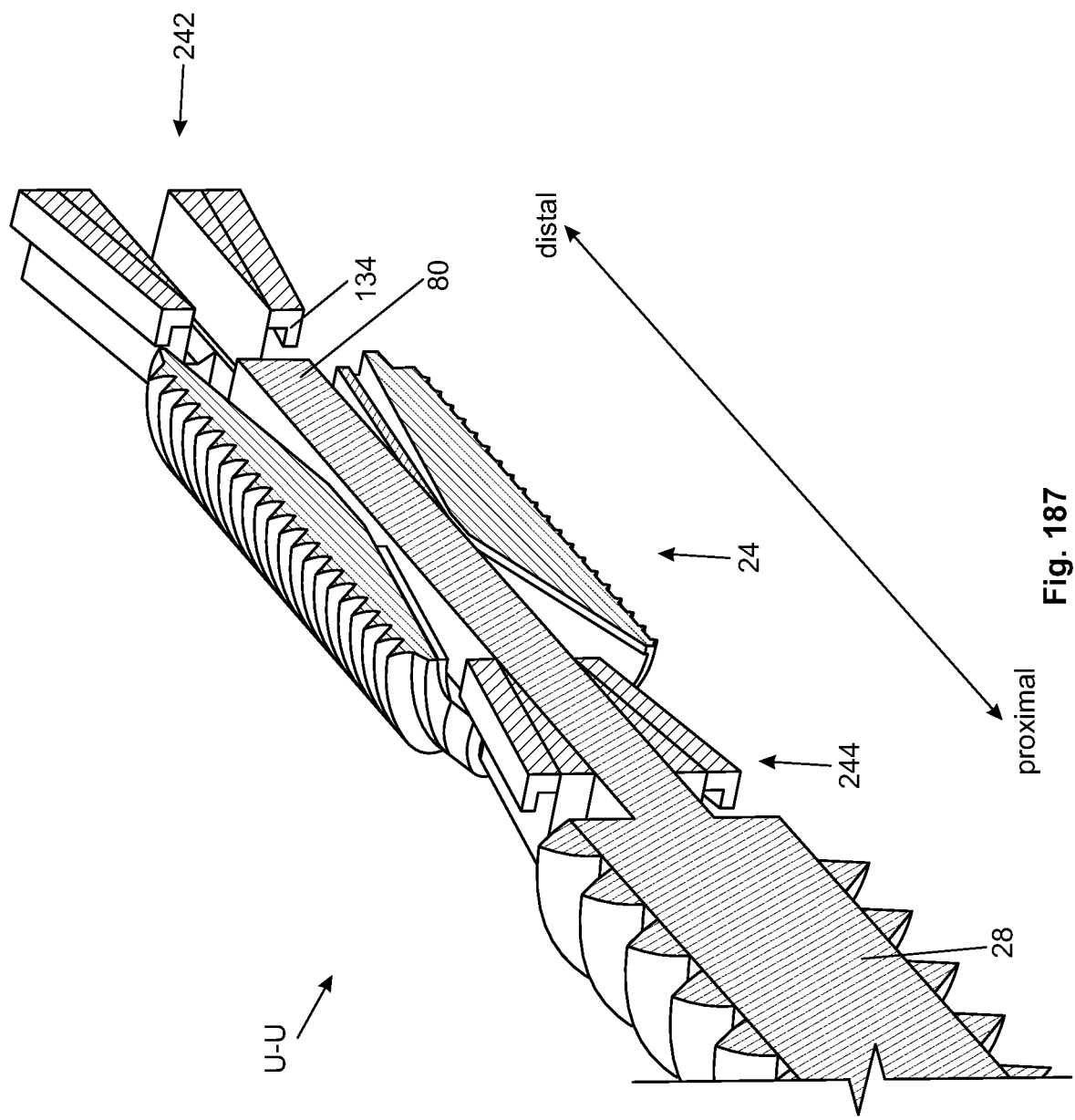

FIGS. 185, 186 and 187 illustrate that the wedges can be segmented. For example, the proximal wedge can have adjacent and/or attached proximal wedge first and second segments. The distal wedge can have adjacent and/or attached distal wedge first and second segments.

The wedge segments can be configured to individually or jointedly fixedly (e.g., via ratcheting on the center shaft and/or wedge) or releasably attach to the center shaft and/or expandable section. For example, the expandable section and/or center shaft can have one or more male or female configurations (e.g., guide slots 124, such as T-slots, as shown) and the wedge segment can have one or more corresponding female or male segments (e.g., wedge rails, such as T-extensions, as shown). When the proximal wedge is forced distally and/or the distal wedge is forced proximally, one or both wedges can force the expandable section to radially expand. When the proximal wedge is forced proximally and/or the distal wedge is forced distally, one or both wedges can force the expandable section to radially contract.

Any or all elements of the expandable attachment device and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, IL; CONICHROME® from Carpenter Metals Corp., Wyomissing, PA), nickel-cobalt alloys (e.g., MP35N® from Magellan Industrial Trading Company, Inc., Westport, CT), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, DE), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N. V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, MA), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable attachment device and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, DE), poly ester amide (PEA), polypropylene, PTFE, ePTFE, nylon, extruded collagen, silicone, any other material disclosed herein, or combinations thereof.

The expandable attachment device and/or elements of the expandable attachment device and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor choline; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, PA; indomethacin;

mefenamic acid), COX-2 inhibitors (e.g., VIOXX® from Merck & Co., Inc., Whitehouse Station, NJ; CELEBREX® from Pharmacia Corp., Peapack, NJ; COX-1 inhibitors); immunosuppressive agents, for example Sirolimus (RAPAMUNE®, from Wyeth, Collegeville, PA), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and *Chlamydia Pneumoniae, Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Other examples of fractures types that can be treated with the disclosed device and method include Greenstick fractures, transverse fractures, fractures across growth plates, simple fractures, wedge fractures, complex fractures, compound fractures, complete fractures, incomplete fractures, linear fractures, spiral fractures, transverse fractures, oblique fractures, comminuted fractures, impacted fractures, and soft tissue tears, separations (e.g., avulsion fracture), sprains, and combinations thereof. Plastic deformations of bones can also be treated with the disclosed device and method.

Other examples of bones that can be treated with the disclosed device and method include the fingers (e.g., phalanges), hands (e.g., metacarpals, carpus), toes (e.g., tarsals), feet (metatarsals, tarsus), legs (e.g., femur, tibia, fibula), arms (e.g., humerus, radius, ulna), scapula, coccyx, pelvis, clavicle, scapula, patella, sternum, ribs, or combinations thereof.

Devices, elements and configurations disclosed as expandable support devices in the following applications can be used for the expandable section in the present application, and the following applications are incorporated by reference herein in their entireties: PCT Application No. 2005/034115 filed 21 Sep. 2005, PCT Application No. 2006/016553 filed 27 Apr. 2006, PCT Application No. 2005/034742 filed 26 Sep. 2005, PCT Application No. 2005/034728 filed 26 Sep. 2005, PCT Application 2005/037126 filed 12 Oct. 2005, PCT Application No. 2006/62333 filed 19 Dec. 2006, PCT Application No. 2006/038920 filed 4 Oct. 2006, PCT Application No. 06/027601 filed 14 Jul. 2006, PCT Application No. 2006/62201 filed 15 Dec. 2006, PCT Application No. 2006/62339 filed 19 Dec. 2006, PCT Application No. 2006/48667 filed 19 Dec. 2006, and U.S. patent application Ser. No. 11/457,772 filed 14 Jul. 2006.

All dimensions shown herein are exemplary. The dimensions shown herein can at least be expanded to ranges from about 50% to about 150% of the exemplary dimension shown herein, more narrowly from about 75% to about 125% of the exemplary dimension shown herein.

The use of the term "radial expansion" herein refers to both a volumetric increase of an element, or an increase in the radial dimension of the element itself, or the increase in the maximum radius of the element as measured from the expandable attachment device axis.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. An orthopedic attachment device comprising:
a tip, an expandable section, and an unexpandable section, wherein the expandable section comprises an expandable thread, wherein the expandable section comprises slots arranged helically along the expandable section, wherein the slots as a group extend fully around a circumference of the expandable section, wherein each slot of the slots intersects the expandable thread at multiple locations along the expandable thread, wherein the slots comprise a first slot, a second slot, a third slot, a fourth slot, a fifth slot, a sixth slot, a seventh slot, an eighth slot, a ninth slot, and a tenth slot,
wherein a distal end of the expandable section comprises the first slot, the second slot, the third slot, and the fourth slot, wherein the first slot, the second slot, the third slot, and the fourth slot are between a first turn of the expandable thread and a second turn of the expandable thread, wherein the distal end of the expandable section comprises the first turn of the expandable thread and the second turn of the expandable thread, wherein the first turn of the expandable thread is adjacent to the second turn of the expandable thread, wherein the first turn of the expandable thread is distal the second turn of the expandable thread, wherein the first slot, the second slot, the third slot, and the fourth slot are between the first turn of the expandable thread and a distal terminal end of the orthopedic attachment device,
wherein a proximal end of the expandable section comprises the fifth slot, the sixth slot, the seventh slot, and the eighth slot, wherein the fifth slot, the sixth slot, the seventh slot, and the eighth slot are between a third turn of the expandable thread and a fourth turn of the expandable thread, wherein the proximal end of the expandable section comprises the third turn of the expandable thread and the fourth turn of the expandable thread, wherein the third turn of the expandable thread is adjacent to the fourth turn of the expandable thread, wherein the third turn of the expandable thread is proximal the fourth turn of the expandable thread, wherein an unexpandable thread is between the third turn of the expandable thread and a proximal terminal end of the orthopedic attachment device, wherein the fifth slot, the sixth slot, the seventh slot, and the eighth slot are between the third turn of the expandable thread and a proximal terminal end of the orthopedic attachment device, wherein the fifth slot, the sixth slot, the seventh slot, and the eighth slot are between the third turn of the expandable thread and the unexpandable thread,
wherein the proximal end of the expandable section and the distal end of the expandable section comprises the ninth slot and the tenth slot, wherein the ninth slot and the tenth slot are on a first side of a fifth turn of the expandable thread and on a second side of the fifth turn of the expandable thread, wherein the first slot, the second slot, the third slot, and the fourth slot are between the second turn and the fifth turn, wherein the fifth slot, the sixth slot, the seventh slot, and the eighth slot are between the fourth turn and the fifth turn, wherein the first slot, the second slot, the third slot, and the fourth slot extend radially through the expandable section and across the first turn of the expandable thread and the second turn of the expandable thread, wherein the fifth slot, the sixth slot, the seventh slot, and the eighth slot extend radially through the expandable section and across the third turn of the expandable thread and the fourth turn of the expandable thread, wherein the ninth slot and the tenth slot extend radially through the expandable section and across the fifth turn of the expandable thread, wherein the first slot has a first slot first longitudinal end and a first slot second longitudinal end, wherein the first slot first longitudinal end is farther from the tip than the first slot second longitudinal end, wherein the first slot second longitudinal end is closer to a distal end of the unexpandable section than to the distal terminal end of the orthopedic attachment device, wherein a length of the first slot is greater than a width of the first slot, wherein the width of the first slot is less than a width of the expandable thread, wherein the second slot has a second slot first longitudinal end and a second slot second longitudinal end, wherein the second slot first longitudinal end is farther from the tip than the second slot second longitudinal end, wherein the second slot second longitudinal end is closer to the distal end of the unexpandable section than to the distal terminal end of the orthopedic attachment device, wherein a length of the second slot is greater than a width of the second slot, wherein the width of the second slot is less than the width of the expandable thread, wherein the third slot has a third slot first longitudinal end and a third slot second longitudinal end, wherein the third slot first longitudinal end is farther from the tip than the third slot second longitudinal end, wherein the third slot second longitudinal end is closer to the distal end of the unexpandable section than to the distal terminal end of the orthopedic attachment device, wherein a length of the third slot is greater than a width of the third slot, wherein the width of the third slot is less than the width of the expandable thread, wherein the fourth slot has a fourth slot first longitudinal end and a fourth slot second longitudinal end, wherein the fourth slot first longitudinal end is farther from the tip than the fourth slot second longitudinal end, wherein the fourth slot second longitudinal end is closer to the distal end of the unexpandable section than to the distal terminal end of the orthopedic attachment device, wherein a length of the fourth slot is greater than a width of the fourth slot, wherein the width of the fourth slot is less than the width of the expandable thread, wherein the fifth slot has a fifth slot first longitudinal end and a fifth slot second longitudinal end, wherein the fifth slot first longitudinal end is farther from the tip than the fifth slot second longitudinal end, wherein the fifth slot second longitudinal end is closer to the distal end of the unexpandable section than to the distal terminal end of the orthopedic attachment device, wherein a length of the fifth slot is greater than a width of the fifth slot, wherein the width of the fifth slot is less than a width of the expandable thread, wherein the sixth slot has a sixth slot first longitudinal end and a sixth slot second longitudinal end, wherein the sixth slot first longitudinal end is farther from the tip than the sixth slot second longitudinal end, wherein the sixth slot second longitudinal end is closer to the distal end of the unexpandable section than to the distal terminal end of the orthopedic attachment device, wherein a length of the sixth slot is greater than a width of the sixth slot, wherein the width of the sixth slot is less than the width of the expandable thread, wherein the seventh slot has a seventh slot first longitudinal end and a seventh slot second longitudinal end, wherein the seventh slot first longitudinal end is farther from the tip than the seventh slot second longitudinal end, wherein the seventh slot second longitudinal end is closer to the distal end of the unexpandable section than to the distal terminal end of the orthopedic attachment device, wherein a length of the seventh slot is greater than a width of the seventh slot, wherein the width of the seventh slot is less than the width of the expandable thread, wherein the eighth slot has a eighth slot first longitudinal end and a eighth slot second longitudinal end, wherein the eighth slot first longitudinal end is farther from the tip than the eighth slot second longitudinal end, wherein the eighth slot second longitudinal end is closer to the distal end of the unexpandable section than to the distal terminal end of the orthopedic attachment device, wherein a length of the eighth slot is greater than a width of the eighth slot, wherein the width of the eighth slot is less than the width of the expandable thread, wherein the ninth slot has a ninth slot first longitudinal end and a ninth slot second longitudinal end, wherein the ninth slot first longitudinal end is farther from the tip than the ninth slot second longitudinal end, wherein the ninth slot second longitudinal end is closer to the distal end of the unexpandable section than to the distal terminal end of the orthopedic attachment device, wherein a length of the ninth slot is greater than a width of the ninth slot, wherein the width of the ninth slot is less than the width of the expandable thread, wherein the tenth slot has a tenth slot first longitudinal end and a tenth slot second longitudinal end, wherein the tenth slot first longitudinal end is farther from the tip than the tenth slot second longitudinal end, wherein the tenth slot second longitudinal end is closer to the distal end of the unexpandable section than to the distal terminal end of the orthopedic attachment device, wherein a length of the tenth slot is greater than a width of the tenth slot, wherein the width of the tenth slot is less than the width of the expandable thread, wherein the unexpandable section comprises the tip and an unexpandable thread, wherein the unexpandable thread is closer to the tip than the expandable thread, wherein the first slot, the second slot, the third slot, the fourth slot, the fifth slot, the sixth slot, the seventh slot, the eight slot, the ninth slot, and the tenth slot are farther from the tip than the unexpandable thread, wherein the tip comprises the proximal terminal end of the orthopedic attachment device when the expandable section is in an unexpanded configuration and when the expandable section is in an expanded configuration, wherein the tip is configured to be in a bone when the expandable section is in the unexpanded configuration and when the expandable section is in the expanded configuration, and wherein the expandable thread is configured to expand radially outward when in the bone.

2. The orthopedic attachment device of claim 1, wherein the expandable thread is at a different angle than the first slot.

3. The orthopedic attachment device of claim 1, further comprising a distal non-expandable length, wherein the expandable section is between the unexpandable section and the distal non-expandable length, and wherein the expandable thread protrudes to substantially a same radius as the unexpandable thread.

4. The orthopedic attachment device of claim 1, wherein when the expandable section is in the unexpanded configuration, the expandable thread has generally a same radius as the unexpandable thread.

5. The orthopedic attachment device of claim 1, wherein a length of the expandable thread between the first slot and the second slot is less than a quarter turn of the expandable thread around the orthopedic attachment device, wherein a length of the expandable thread between the second slot and the third slot is less than a quarter turn of the expandable thread around the orthopedic attachment device, wherein a length of the expandable thread between the third slot and the fourth slot is less than a quarter turn of the expandable thread around the orthopedic attachment device, wherein a length of the expandable thread between the fifth slot and the sixth slot is less than a quarter turn of the expandable thread around the orthopedic attachment device, wherein a length of the expandable thread between the sixth slot and the seventh slot is less than a quarter turn of the expandable thread around the orthopedic attachment device, wherein a length of the expandable thread between the seventh slot and the eighth slot is less than a quarter turn of the expandable thread around the orthopedic attachment device, wherein a length of the expandable thread between the ninth slot and the tenth slot is less than a quarter turn of the expandable thread around the orthopedic attachment device.

6. The orthopedic attachment device of claim 5, further comprising a shaft comprising the expandable section and the unexpandable section, wherein the shaft comprises a shaft deployment tool attachment.

7. The orthopedic attachment device of claim 5, further comprising a distal cap, wherein the distal cap comprises a spherical configuration, and wherein the distal cap comprises a cap deployment tool attachment.

8. The orthopedic attachment device of claim 1, wherein at least three slots of the first slot, the second slot, the third slot, the fourth slot, the fifth slot, the sixth slot, the seventh slot, the eighth slot, the ninth slot, and the tenth slot are arranged in a helical configuration along the expandable section.

9. The orthopedic attachment device of claim 1, wherein the first slot, the fifth slot, and the ninth slot are arranged in a helical configuration along the expandable section.

10. The orthopedic attachment device of claim 1, wherein the width of the expandable thread comprises a width of a base of the expandable thread, wherein the tip is configured to cut bone, wherein the ninth slot and the tenth slot are between the first slot first longitudinal end and the fifth slot second longitudinal end, wherein the ninth slot and the tenth slot are between the second slot first longitudinal end and the sixth slot second longitudinal end, wherein the ninth slot and the tenth slot are between the third slot first longitudinal end and the seventh slot second longitudinal end, and wherein the ninth slot and the tenth slot are between the fourth slot first longitudinal end and the eighth slot second longitudinal end.

11. The orthopedic attachment device of claim 1, wherein the first slot first longitudinal end comprises a first slot first longitudinal terminal end, wherein the second slot first longitudinal end comprises a second slot first longitudinal terminal end, wherein the third slot first longitudinal end comprises a third slot first longitudinal terminal end, wherein the fourth slot first longitudinal end comprises a fourth slot first longitudinal terminal end, wherein the first slot second longitudinal end comprises a first slot second longitudinal terminal end, wherein the second slot second longitudinal end comprises a second slot second longitudinal terminal end, wherein the third slot second longitudinal end comprises a third slot second longitudinal terminal end, wherein the fourth slot second longitudinal end comprises a fourth slot second longitudinal terminal end, wherein the fifth slot first longitudinal end comprises a fifth slot first longitudinal terminal end, wherein the sixth slot first longitudinal end comprises a sixth slot first longitudinal terminal end, wherein the seventh slot first longitudinal end comprises a seventh slot first longitudinal terminal end, wherein the eighth slot first longitudinal end comprises a eighth slot first longitudinal terminal end, wherein the fifth slot second longitudinal end comprises a fifth slot second longitudinal terminal end, wherein the sixth slot second longitudinal end comprises a sixth slot second longitudinal terminal end, wherein the seventh slot second longitudinal end comprises a seventh slot second longitudinal terminal end, wherein the eighth slot second longitudinal end comprises a eighth slot second longitudinal terminal end, wherein the ninth slot first longitudinal end comprises a ninth slot first longitudinal terminal end, wherein the tenth slot first longitudinal end comprises a tenth slot first longitudinal terminal end, and wherein the ninth slot second longitudinal end comprises a ninth slot second longitudinal terminal end, wherein the tenth slot second longitudinal end comprises a tenth slot second longitudinal terminal end.

12. The orthopedic attachment device of claim 1, wherein the ninth slot and the tenth slot are between the fifth turn of the expandable thread and a sixth turn of the expandable thread, wherein the fifth turn of the expandable thread is adjacent to the sixth turn of the expandable thread, wherein the fifth turn of the expandable thread is proximal the sixth turn of the expandable thread, wherein the first slot, the second slot, the third slot, and the fourth slot are between the second turn and the sixth turn, wherein the fifth slot, the sixth slot, the seventh slot, and the eighth slot are between the fourth turn and the sixth turn, wherein the ninth slot and the tenth slot extend radially through the expandable section and across the sixth turn of the expandable thread, wherein the width of the first slot is less than a width of the first turn of the expandable thread, wherein the width of the first slot is less than a width of the second turn of the expandable thread, wherein the width of the second slot is less than the width of the first turn of the expandable thread, wherein the width of the second slot is less than the width of the second turn of the expandable thread, wherein the width of the third slot is less than the width of the first turn of the expandable thread, wherein the width of the third slot is less than the width of the second turn of the expandable thread, wherein the width of the fourth slot is less than the width of the first turn of the expandable thread, wherein the width of the fourth slot is less than the width of the second turn of the expandable thread, wherein the width of the fifth slot is less than a width of the third turn of the expandable thread, wherein the width of the fifth slot is less than a width of the fourth turn of the expandable thread, wherein the width of the sixth slot is less than the width of the third turn of the expandable thread, wherein the width of the sixth slot is less than the width of the fourth turn of the expandable thread, wherein the width of the seventh slot is less than the width of the third turn of the expandable thread, wherein the width of the seventh slot is less than the width of the fourth turn of the expandable thread, wherein the width of the eighth slot is less than the width of the third turn of the expandable thread, wherein the width of the eighth slot is less than the width of the fourth turn of the expandable thread, wherein the width of the ninth slot is less than a width of the fifth turn of the expandable thread, wherein the width of the ninth slot is less than a width of the sixth turn of the expandable thread, and wherein the width of the tenth slot is less than the width of the fifth turn of the expandable thread, wherein the width of the tenth slot is less than the width of the sixth turn of the expandable thread.

13. The orthopedic attachment device of claim 1, wherein a helical angle of the expandable thread and a helical angle of the slots arranged helically along the expandable section are different from each other such that each slot of the slots intersects the expandable thread at multiple locations along the expandable thread.

14. An orthopedic attachment device comprising:
a tip, an expandable section, and an unexpandable section,
wherein the expandable section comprises an expandable thread and slots, wherein a group of the slots is in a helical arrangement along the expandable section, wherein the slots jointly extend fully around a circumference of the expandable section, wherein each of the slots intersects the expandable thread at multiple locations along the expandable thread, wherein the slots comprise a first slot, a second slot, a third slot, a fourth slot, a fifth slot, and a sixth slot, wherein a first circumferential half of the expandable section comprises the first slot, the second slot, the third slot, the fourth slot, the fifth slot, and the sixth slot, wherein the first slot, the second slot, the third slot, the fourth slot, the fifth slot, and the sixth slot each extend radially through the expandable thread, wherein the first slot extends through at least 3 turns of the expandable thread, wherein the second slot extends through at least 3 turns of the expandable thread, wherein the third slot extends through at least 2 turns of the expandable thread, wherein the fourth slot extends through at least 2 turns of the expandable thread, wherein the fifth slot extends through at least 3 turns of the expandable thread, wherein the sixth slot extends through at least 3 turns of the expandable thread, wherein the first slot has a first slot first longitudinal terminal end and a first slot second longitudinal terminal end, wherein the first slot first longitudinal terminal end is farther from the tip than the first slot second longitudinal terminal end, wherein the first slot second longitudinal terminal end is closer to a distal end of the unexpandable section than to a distal terminal end of the orthopedic attachment device, wherein a length of the first slot is greater than a width of the first slot, wherein the width of the first slot is less than a distance between two adjacent flanks of the expandable thread, wherein the second slot has a second slot first longitudinal terminal end and a second slot second longitudinal terminal end, wherein the second slot first longitudinal terminal end is farther from the tip than the second slot second longitudinal terminal end, wherein the second slot second longitudinal terminal end is closer to the distal end of the unexpandable section than to the distal terminal end of the orthopedic attachment device, wherein a length of the second slot is greater than a width of the second slot, wherein the width of the second slot is less than the distance between the two adjacent flanks of the expandable thread, wherein the third slot has a third slot first longitudinal terminal end and a third slot second longitudinal terminal end, wherein the third slot first longitudinal terminal end is farther from the tip than the third slot second longitudinal terminal end, wherein the third slot second longitudinal terminal end is closer to the distal end of the unexpandable section than to the distal terminal end of the orthopedic attachment device, wherein a length of the third slot is greater than a width of the third slot, wherein the width of the third slot is less than the distance between the two adjacent flanks of the expandable thread, wherein the fourth slot has a fourth slot first longitudinal terminal end and a fourth slot second longitudinal terminal end, wherein the fourth slot first longitudinal terminal end is farther from the tip than the fourth slot second longitudinal terminal end, wherein the fourth slot second longitudinal terminal end is closer to the distal end of the unexpandable section than to the distal terminal end of the orthopedic attachment device, wherein a length of the fourth slot is greater than a width of the fourth slot, wherein the width of the fourth slot is less than the distance between the two adjacent flanks of the expandable thread, wherein the fifth slot has a fifth slot first longitudinal terminal end and a fifth slot second longitudinal terminal end, wherein the fifth slot first longitudinal terminal end is farther from the tip than the fifth slot second longitudinal terminal end, wherein the fifth slot second longitudinal terminal end is closer to the distal end of the unexpandable section than to the distal terminal end of the orthopedic attachment device, wherein a length of the fifth slot is greater than a width of the fifth slot, wherein the width of the fifth slot is less than the distance between the two adjacent flanks of the expandable thread, wherein the sixth slot has a sixth slot first longitudinal terminal end and a sixth slot second longitudinal terminal end, wherein the sixth slot first longitudinal terminal end is farther from the tip than the sixth slot second longitudinal terminal end, wherein the sixth slot second longitudinal terminal end is closer to the distal end of the unexpandable section than to the distal terminal end of the orthopedic attachment device, wherein a length of the sixth slot is greater than a width of the sixth slot, wherein the width of the sixth slot is less than the distance between the two adjacent flanks of the expandable thread, wherein the unexpandable section comprises an unexpandable thread, wherein the unexpandable thread is closer to the tip than the expandable thread, wherein the first slot, the second slot, the third slot, the fourth slot, the fifth slot, and the sixth slot are farther from the tip than the unexpandable thread, wherein the tip comprises a proximal terminal end of the orthopedic attachment device when the expandable section is in an unexpanded configuration and when the expandable section is in an expanded configuration, wherein the tip is configured to be in a bone when the expandable section is in the unexpanded configuration and when the expandable section is in the expanded configuration, wherein the expandable thread is configured to expand radially outward when in the bone, wherein a distal end of the expandable section comprises the first slot and the second slot, wherein the distal end of the expandable section and a proximal end of the expandable section comprises the third slot and the fourth slot, wherein the proximal end of the expandable section comprises the fifth slot and the sixth slot, wherein when the expandable section is in the unexpanded configuration, the third slot is circumferentially between the first slot and the sixth slot, wherein when the expandable section is in the unexpanded configuration, the third slot is circumferentially between the second slot and the fifth slot, wherein when the expandable section is in the unexpanded configuration, a middle of the third slot and a middle of the fourth slot are between a middle of the first slot and a middle of the sixth slot, wherein when the expandable section is in the unexpanded configuration, the middle of the third slot and the middle of the fourth slot are between a middle of the second slot and a middle of the fifth slot, wherein when the expandable section is in the unexpanded configuration, the middle of the third slot is between the first slot first longitudinal terminal end and the sixth slot second longitudinal terminal end, wherein when the expandable section is in the unexpanded configuration, the middle of the fourth slot is between the first slot first longitudinal terminal end and the sixth slot second longitudinal terminal end, wherein a length of the expandable thread between the first slot and the second slot is less than a quarter turn of the expandable thread around the orthopedic attachment device, wherein a length of the expandable thread between the third slot and the fourth slot is less than a quarter turn of the expandable thread around the orthopedic attachment device, wherein a length of the expandable thread between the fifth slot and the sixth slot is less than a quarter turn of the expandable thread around the orthopedic attachment device.

15. The orthopedic attachment device of claim 14, wherein when the expandable section is in the unexpanded configuration, a longitudinal axis of the first slot, a longitudinal axis of the second slot, a longitudinal axis of the third slot, a longitudinal axis of the fourth slot, a longitudinal axis of the fifth slot, and a longitudinal axis of the sixth slot each has a curved shape that extends at least partially around a center longitudinal axis of the expandable section, wherein the expandable section comprises a seventh slot, an eighth slot, and a ninth slot, wherein a second circumferential half of the expandable section comprises the seventh slot, the eighth slot, and the ninth slot, wherein the second circumferential half of the expandable section is opposite the first circumferential half of the expandable section, wherein the seventh slot, the eighth slot, and the ninth slot each extends radially through the expandable thread, wherein the seventh slot, the eighth slot, and the ninth slot each extends through at least 3 turns of the expandable thread, wherein the first slot, the third slot, and the fifth slot are arranged helically around the center longitudinal axis of the expandable section, and wherein the seventh slot, the eighth slot, and the ninth slot are arranged helically around the center longitudinal axis of the expandable section.

16. The orthopedic attachment device of claim 14, wherein at least three slots of the first slot, the second slot, the third slot, the fourth slot, the fifth slot, and the sixth slot are arranged in a helical configuration along the expandable section.

17. The orthopedic attachment device of claim 14, further comprising a distal non-expandable length, wherein the expandable section is between the unexpandable section and the distal non-expandable length.

18. The orthopedic attachment device of claim 14, wherein a helical angle of the expandable thread and a helical angle of the group of the slots in the helical arrangement are different from each other such that each of the slots intersects the expandable thread at multiple locations along the expandable thread.

19. An orthopedic attachment device comprising:

a tip, an expandable section, and an unexpandable section, wherein the expandable section comprises an expandable thread, wherein the expandable section comprises a first set of slots, a second set of slots, and a third set of slots, wherein the first set of slots comprises a first slot, a second slot, and a third slot arranged helically along the expandable section, wherein the second set of slots comprises a fourth slot, a fifth slot, and a sixth slot arranged helically along the expandable section, wherein the third set of slots comprises a seventh slot, an eighth slot, and a ninth slot arranged helically along the expandable section, wherein the first slot, the second slot, the third slot, the fourth slot, the fifth slot, the sixth slot, the seventh slot, the eighth slot, and the ninth slot each extend through at least 2 turns of the expandable thread such that the first slot, the second slot, the third slot, the fourth slot, the fifth slot, the sixth slot, the seventh slot, the eighth slot, and the ninth slot each intersect the expandable thread at a first location and a second location along the expandable thread, wherein the first location that the first slot intersects the expandable thread is closer to the tip than the second location that the first slot intersects the expandable thread, wherein the first location that the second slot intersects the expandable thread is closer to the tip than the second location that the second slot intersects the expandable thread, wherein the first location that the third slot intersects the expandable thread is closer to the tip than the second location that the third slot intersects the expandable thread, wherein the first location that the fourth slot intersects the expandable thread is closer to the tip than the second location that the fourth slot intersects the expandable thread, wherein the first location that the fifth slot intersects the expandable thread is closer to the tip than the second location that the fifth slot intersects the expandable thread, wherein the first location that the sixth slot intersects the expandable thread is closer to the tip than the second location that the sixth slot intersects the expandable thread, wherein the first location that the seventh slot intersects the expandable thread is closer to the tip than the second location that the seventh slot intersects the expandable thread, wherein the first location that the eighth slot intersects the expandable thread is closer to the tip than the second location that the eighth slot intersects the expandable thread, wherein the first location that the ninth slot intersects the expandable thread is closer to the tip than the second location that the ninth slot intersects the expandable thread, wherein a distal end of the expandable section comprises the first slot, the fourth slot, and the seventh slot, wherein the distal end of the expandable section and a proximal end of the expandable section comprises the second slot, the fifth slot, and the eighth slot, wherein the proximal end of the expandable section comprises the third slot, the sixth slot, and the ninth slot, wherein the first slot, the second slot, the third slot, the fourth slot, the fifth slot, the sixth slot, the seventh slot, the eighth slot, and the ninth slot each extend through an entire thickness of the expandable thread, wherein the first slot has a first slot first longitudinal terminal end and a first slot second longitudinal terminal end, wherein the first slot first longitudinal terminal end is farther from the tip than the first slot second longitudinal terminal end, wherein the first slot second longitudinal end is closer to a distal end of the unexpandable section than to a distal terminal end of the orthopedic attachment device, wherein a length of the first slot is greater than a width of the first slot, wherein the width of the first slot is less than a distance between two adjacent roots of the expandable thread, wherein the second slot has a second slot first longitudinal terminal end and a second slot second longitudinal terminal end, wherein the second slot first longitudinal terminal end is farther from the tip than the second slot second longitudinal terminal end, wherein the second slot second longitudinal end is closer to the distal end of the unexpandable section than to the distal terminal end of the orthopedic attachment device, wherein a length of the second slot is greater than a width of the second slot, wherein the width of the second slot is less than the distance between the two adjacent roots of the expandable thread, wherein the third slot has a third slot first longitudinal terminal end and a third slot second longitudinal terminal end, wherein the third slot first longitudinal terminal end is farther from the tip than the third slot second longitudinal terminal end, wherein the third slot second longitudinal end is closer to the distal end of the unexpandable section than to the distal terminal end of the orthopedic attachment device, wherein a length of the third slot is greater than a width of the third slot, wherein the width of the third slot is less than the distance between the two adjacent roots of the expandable thread, wherein the fourth slot has a fourth slot first longitudinal terminal end and a fourth slot second longitudinal terminal end, wherein the fourth slot first longitudinal terminal end is farther from the tip than the fourth slot second longitudinal terminal end, wherein the fourth slot second longitudinal end is closer to the distal end of the unexpandable section than to the distal terminal end of the orthopedic attachment device, wherein a length of the fourth slot is greater than a width of the fourth slot, wherein the width of the fourth slot is less than the distance between the two adjacent roots of the expandable thread, wherein the fifth slot has a fifth slot first longitudinal terminal end and a fifth slot second longitudinal terminal end, wherein the fifth slot first longitudinal terminal end is farther from the tip than the fifth slot second longitudinal terminal end, wherein the fifth slot second longitudinal end is closer to the distal end of the unexpandable section than to the distal terminal end of the orthopedic attachment device, wherein a length of the fifth slot is greater than a width of the fifth slot, wherein the width of the fifth slot is less than the distance between the two adjacent roots of the expandable thread, wherein the sixth slot has a sixth slot first longitudinal terminal end and a sixth slot second longitudinal terminal end, wherein the sixth slot first longitudinal terminal end is farther from the tip than the sixth slot second longitudinal terminal end, wherein the sixth slot second longitudinal end is closer to the distal end of the unexpandable section than to the distal terminal end of the orthopedic attachment device, wherein a length of the sixth slot is greater than a width of the sixth slot, wherein the width of the sixth slot is less than the distance between the two adjacent roots of the expandable thread, wherein the unexpandable section comprises an unexpandable thread, wherein the unexpandable thread is closer to the tip than the expandable thread, wherein the first slot, the second slot, the third slot, the fourth slot, the fifth slot, the sixth slot, the seventh slot, the eighth slot, and the ninth slot are farther from the tip than the unexpandable thread, wherein the tip comprises a proximal terminal end of the orthopedic attachment device when the expandable section is in an unexpanded configuration and when the expandable section is in an expanded configuration, wherein the tip is configured to be in a bone when the expandable section is in the unexpanded configuration and when the expandable section is in the expanded configuration, wherein the expandable thread is configured to expand radially outward when in the bone, wherein a first circumferential half of the expandable section comprises the first slot, the second slot, and the third slot, wherein a second circumferential half of the expandable section comprises the seventh slot, the eighth slot, and the ninth slot, and wherein the second circumferential half of the expandable section is opposite the first circumferential half of the expandable section.

20. The orthopedic attachment device of claim 19, further comprising a distal non-expandable length, wherein the expandable section is between the unexpandable section and the distal non-expandable length.

* * * * *